US007981598B2

(12) United States Patent
Ichinose et al.

(10) Patent No.: US 7,981,598 B2
(45) Date of Patent: Jul. 19, 2011

(54) PREVENTIVE/REMEDY FOR RESPIRATORY DISEASES

(75) Inventors: Masakazu Ichinose, Wakayama (JP); Hiromasa Ogawa, Miyagi (JP); Masafumi Tomaki, Miyagi (JP); Yumiko Uno, Ibaraki (JP); Makoto Furusawa, Ibaraki (JP); Tatsumi Matsumoto, Osaka (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 831 days.

(21) Appl. No.: 10/594,266

(22) PCT Filed: Mar. 25, 2005

(86) PCT No.: PCT/JP2005/006444

§ 371 (c)(1),
(2), (4) Date: Mar. 21, 2007

(87) PCT Pub. No.: WO2005/092383

PCT Pub. Date: Oct. 6, 2005

(65) Prior Publication Data

US 2007/0207462 A1 Sep. 6, 2007

(30) Foreign Application Priority Data

Mar. 26, 2004 (JP) ................................ 2004-092064

(51) Int. Cl.
*C12Q 1/00* (2006.01)
*G01N 33/53* (2006.01)
*G01N 33/00* (2006.01)
*C12Q 1/60* (2006.01)
*C12Q 1/48* (2006.01)

(52) U.S. Cl. ............ 435/4; 435/7.71; 435/7.93; 435/11; 435/15

(58) Field of Classification Search ........................ None
See application file for complete search history.

(56) References Cited

U.S. PATENT DOCUMENTS

2004/0253599 A1 12/2004 Nakanishi et al.

FOREIGN PATENT DOCUMENTS

EP 1 394 274 A2 3/2004
JP 2003-274982 A 9/2003
JP 2003-325187 A 11/2003
WO WO-00/23596 4/2000
WO WO-02/099134 A1 12/2002
WO WO-03/073990 A2 9/2003

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Andreas Pappassotiropoulos et al., "Cholesterol 25-Hydroxylase on Chromosine 10q is a Susceptibility Gene for Sporadic Alzheimer's Disease," Neurodegenerative Diseases; 2005; 2: pp. 233-241.
T. Rosklint, G.G. et al., "Oxysterols induce interleukin-1β production in human macrophages," European Journal of Clinical Investigation, 2002, vol. 32, pp. 35-42.
Erik G. Lund et al., "cDNA Cloning of Mouse and Human Cholesterol 25-Hydroxylases, Polytopic Membrane Proteins that Synthesize a Potent Oxysterol Regulator of Lipid Metabolism," The Journal of Biological Chemistry, 1998, vol. 273, No. 51, Dec. 18, pp. 34316-34327.
Lemaire-Ewing S. et al.; "Comparison of the cytotoxic, pro-oxidant and pro-inflammatory characteristics of different oxysterols;" Cell Biology and Toxicology; Mar. 2005; vol. 21; pp. 97-114.
Rydberg E.K. et al.; "Hypoxia increases 25-hydroxycholesterol-induced interleukin-8 protein secretion in human macrophages" Atherosclerosis; Oct. 2003; vol. 170; pp. 245-252.
Chang J.Y. et al.; "Peroxisome proliferator-activated receptor agonists prevent 25-OH-cholesterol induced c-jun activation and cell death"; BMC Pharmacology; Nov. 2001; 1:10.
O'Callaghan Y.C. et al.; "Oxysterol-induced cell death in U937 and HepG2 cells at reduced and normal serum concentrations"; Eur. J. Nutr.; Dec. 1999; vol. 38; pp. 255-262.
Yin J. et al.; "Apoptosis of vascular smooth muscle cells induced by cholesterol and its oxides in vitro and in vivo"; Atherosclerosis. Feb. 2000; vol. 148; pp. 365-374.
Chang J.Y. et al.; "Cholesterol oxides induce programmed cell death in microglial cells"; Biochemical and Biophysical Research Communications; Aug. 1998; vol. 249; pp. 817-821.
Chang J.Y. et al.; "Neurotoxicity of 25-CH-cholesterol on NGF-differentiated PC12 cells"; Neurochemical Research; Jan. 1998; vol. 23; pp. 7-16.

* cited by examiner

*Primary Examiner* — Suzanne M Noakes
*Assistant Examiner* — Jae W Lee
(74) *Attorney, Agent, or Firm* — Edwards Angell Palmer & Dodge LLP; David G. Conlin; Kathryn A. Piffat, Esq.

(57) ABSTRACT

It is intended to provide a compound inhibiting the activity of a protein having an amino acid sequence which is the same or substantially the same as one of the amino acid sequences represented by SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62 and so on, or its salt; a compound inhibiting the expression of a gene of the above protein; an antisense nucleotide containing a base sequence which is complementary or substantially complementary to the base sequence of a DNA encoding the above protein or its partial peptide or a part of the base sequence; an antibody against the above protein or its partial peptide; and so on. The above compound, antisense nucleotide, antibody and so on are usable as a prophylactic/therapeutic agent for respiratory diseases, etc.

3 Claims, 8 Drawing Sheets

EXPRESSION VALUE
3.5
3.0
2.5
2.0
1.5
1.0
0.5
0.0
NN
NE
NS
CE1
CE2A (A)

CH25H

CYP27A1

(B)

CH25H

CYP27A1

SEQUENCE LISTING

<160> NUMBER OF SEQ ID NOS: 74

<210> SEQ ID NO 1
<211> LENGTH: 816
<212> TYPE: DNA
<213> ORGANISM: Homo sapiens

<400> SEQUENCE: 1
atgagctgcc acaactgctc cgaccccag gtcctttgca gctccgggca gctgttcctg 60
cagcccctct gggaccacct gaggagctgg gaggccctcc tacagtcgcc cttcttcccg 120
gtcatcttct ccatcaccac atacgtgggc ttttgcctgc ccttcgtggt cctggatatc 180
ctgtgctcct gggtgcccgc cctgcggcgc tacaagatcc accctgactt ctcgccatcc 240
gcgcagcagc tgctaccttg cctggggcag accctctacc agcatgtgat gtttgtgttc 300
cccgtgacgc tgctgcattg ggcccgcagc ccggccctcc tgccccacga agctcccgag 360
ctgctcctgc tgctgcacca catcctgttc tgcctgctac tcttcgacat ggagttcttc 420
gtgtggcacc tgctgcacca caaggtgccc tggctgtacc gcaccttcca caaggtgcac 480
caccagaact cgtcctcgtt cgcgctggca acgcagtata tgagcgtctg ggaactgttt 540
tctttgggct tcttcgacat gatgaacgtc acactgctcg ggtgccaccc gctcaccacc 600
ctgaccttcc acgtggtcaa catctggctt tccgtggagg accactccgg ctacaacttc 660
ccttggtcca ctcacagact ggtgcccttc gggtggtacg ggggtgtggt gcaccacgac 720
ctgcatcact ctcactttaa ctgcaacttc gctccgtact ttacacactg ggacaaaata 780
ctgggaacgc tgcggactgc atctgtccca gcgcgg 816

<210> SEQ ID NO 2
<211> LENGTH: 272
<212> TYPE: PRT

<213> ORGANISM: Homo sapiens

<400> SEQUENCE: 2

```
Met Ser Cys His Asn Cys Ser Asp Pro Gln Val Leu Cys Ser Ser Gly
1               5                   10                  15

Gln Leu Phe Leu Gln Pro Leu Trp Asp His Leu Arg Ser Trp Glu Ala
            20                  25                  30

Leu Leu Gln Ser Pro Phe Phe Pro Val Ile Phe Ser Ile Thr Thr Tyr
        35                  40                  45

Val Gly Phe Cys Leu Pro Phe Val Val Leu Asp Ile Leu Cys Ser Trp
    50                  55                  60

Val Pro Ala Leu Arg Arg Tyr Lys Ile His Pro Asp Phe Ser Pro Ser
65                  70                  75                  80

Ala Gln Gln Leu Leu Pro Cys Leu Gly Gln Thr Leu Tyr Gln His Val
                85                  90                  95

Met Phe Val Phe Pro Val Thr Leu Leu His Trp Ala Arg Ser Pro Ala
            100                 105                 110

Leu Leu Pro His Glu Ala Pro Glu Leu Leu Leu Leu His His Ile
        115                 120                 125

Leu Phe Cys Leu Leu Leu Phe Asp Met Glu Phe Phe Val Trp His Leu
    130                 135                 140

Leu His His Lys Val Pro Trp Leu Tyr Arg Thr Phe His Lys Val His
145                 150                 155                 160

His Gln Asn Ser Ser Ser Phe Ala Leu Ala Thr Gln Tyr Met Ser Val
                165                 170                 175

Trp Glu Leu Phe Ser Leu Gly Phe Phe Asp Met Met Asn Val Thr Leu
            180                 185                 190

Leu Gly Cys His Pro Leu Thr Thr Leu Thr Phe His Val Val Asn Ile
        195                 200                 205

Trp Leu Ser Val Glu Asp His Ser Gly Tyr Asn Phe Pro Trp Ser Thr
    210                 215                 220

His Arg Leu Val Pro Phe Gly Trp Tyr Gly Gly Val Val His His Asp
225                 230                 235                 240

Leu His His Ser His Phe Asn Cys Asn Phe Ala Pro Tyr Phe Thr His
                245                 250                 255

Trp Asp Lys Ile Leu Gly Thr Leu Arg Thr Ala Ser Val Pro Ala Arg
            260                 265                 270
```

<210> SEQ ID NO 3
<211> LENGTH: 924
<212> TYPE: DNA
<213> ORGANISM: Homo sapiens

<400> SEQUENCE: 3

```
atgcccgggc aagaactcag gacgctgaat ggctctcaga tgctcctggt gttgctggtg      60

ctctcgtggc tgccgcatgg gggcgccctg tctctggccg aggcgagccg cgcaagtttc     120

ccgggaccct cagagttgca ctccgaagac tccagattcc gagagttgcg gaaacgctac     180

gaggacctgc taaccaggct gcgggccaac cagagctggg aagattcgaa caccgacctc     240

gtcccggccc ctgcagtccg gatactcacg ccagaagtgc ggctgggatc cggcggccac     300

ctgcacctgc gtatctctcg ggccgccctt cctgaggggc tccccgaggc ctcccgcctt     360

caccgggctc tgttccggct gtccccgacg gcgtcaaggt cgtgggacgt gacacgaccg     420

ctgcggcgtc agctcagcct tgcaagaccc caggcgcccg cgctgcacct gcgactgtcg     480

ccgccgccgt cgcagtcgga ccaactgctg gcagaatctt cgtccgcacg gccccagctg     540
```

```
gagttgcact tgcggccgca agccgccagg gggcgccgca gagcgcgtgc gcgcaacggg    600

gaccactgtc cgctcgggcc cgggcgttgc tgccgtctgc acacggtccg cgcgtcgctg    660

gaagacctgg gctgggccga ttgggtgctg tcgccacggg aggtgcaagt gaccatgtgc    720

atcggcgcgt gcccgagcca gttccgggcg gcaaacatgc acgcgcagat caagacgagc    780

ctgcaccgcc tgaagcccga cacggtgcca gcgccctgct gcgtgcccgc cagctacaat    840

cccatggtgc tcattcaaaa gaccgacacc ggggtgtcgc tccagaccta tgatgacttg    900

ttagccaaag actgccactg cata                                           924


<210> SEQ ID NO 4
<211> LENGTH: 308
<212> TYPE: PRT
<213> ORGANISM: Homo sapiens

<400> SEQUENCE: 4

Met Pro Gly Gln Glu Leu Arg Thr Leu Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300
```

```
Cys His Cys Ile
305


<210> SEQ ID NO 5
<211> LENGTH: 621
<212> TYPE: DNA
<213> ORGANISM: Homo sapiens

<400> SEQUENCE: 5

atggctggac ctgccaccca gagccccatg aagctgatgg ccctgcagct gctgctgtgg     60

cacagtgcac tctggacagt gcaggaagcc acccccctgg gccctgccag ctccctgccc    120

cagagcttcc tgctcaagtg cttagagcaa gtgaggaaga tccagggcga tggcgcagcg    180

ctccaggaga agctggtgag tgagtgtgcc acctacaagc tgtgccaccc cgaggagctg    240

gtgctgctcg gacactctct gggcatcccc tgggctcccc tgagcagctg ccccagccag    300

gccctgcagc tggcaggctg cttgagccaa ctccatagcg gccttttcct ctaccagggg    360

ctcctgcagg ccctggaagg gatctccccc gagttgggtc ccaccttgga cacactgcag    420

ctggacgtcg ccgactttgc caccaccatc tggcagcaga tggaagaact gggaatggcc    480

cctgccctgc agcccaccca gggtgccatg ccggccttcg cctctgcttt ccagcgccgg    540

gcaggagggg tcctggttgc ctcccatctg cagagcttcc tggaggtgtc gtaccgcgtt    600

ctacgccacc ttgcccagcc c                                              621


<210> SEQ ID NO 6
<211> LENGTH: 207
<212> TYPE: PRT
<213> ORGANISM: Homo sapiens

<400> SEQUENCE: 6

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205
```

<210> SEQ ID NO 7
<211> LENGTH: 696
<212> TYPE: DNA
<213> ORGANISM: Homo sapiens

<400> SEQUENCE: 7

```
atgaaggaga gacgggcccc ccagccagtc gtggccagat gtaagctcgt tctggtcggg     60

gacgtgcagt gtgggaagac cgcgatgttg caagtgttag cgaaggattg ctatccagag    120

acctatgtgc ccaccgtgtt cgaaaattac acagcctgtt tggagacaga ggaacagagg    180

gtggagctta gtctctggga tacctcagga tctccctact acgataatgt ccgtccactc    240

tgctacagcg actcggatgc agtattacta tgttttgaca tcagccgtcc agagacagtg    300

gacagcgcac tcaagaagtg gaggacagaa atcctagatt attgtcccag cacccgcgtt    360

ttgctcattg gctgcaagac agacctgcga acagacctga gtactctgat ggagctgtcc    420

caccagaagc aggcgcccat ctcctatgag cagggttgtg caatagcaaa gcagctgggt    480

gcagaaatct acctggaagg ctcagctttc acctcagaaa agagcatcca cagcatcttt    540

cggacggcat ccatgctgtg tctgaacaag cctagcccac tgccccagaa gagccctgtc    600

cgaagcctct ccaaacgact gctccacctc cccagtcgct ctgaactcat ctcttctacc    660

ttcaagaagg aaaaggccaa aagctgttcc attatg                              696
```

<210> SEQ ID NO 8
<211> LENGTH: 232
<212> TYPE: PRT
<213> ORGANISM: Homo sapiens

<400> SEQUENCE: 8

```
Met Lys Glu Arg Arg Ala Pro Gln Pro Val Val Ala Arg Cys Lys Leu
1               5                   10                  15

Val Leu Val Gly Asp Val Gln Cys Gly Lys Thr Ala Met Leu Gln Val
            20                  25                  30

Leu Ala Lys Asp Cys Tyr Pro Glu Thr Tyr Val Pro Thr Val Phe Glu
        35                  40                  45

Asn Tyr Thr Ala Cys Leu Glu Thr Glu Glu Gln Arg Val Glu Leu Ser
    50                  55                  60

Leu Trp Asp Thr Ser Gly Ser Pro Tyr Tyr Asp Asn Val Arg Pro Leu
65                  70                  75                  80

Cys Tyr Ser Asp Ser Asp Ala Val Leu Leu Cys Phe Asp Ile Ser Arg
                85                  90                  95

Pro Glu Thr Val Asp Ser Ala Leu Lys Lys Trp Arg Thr Glu Ile Leu
            100                 105                 110

Asp Tyr Cys Pro Ser Thr Arg Val Leu Leu Ile Gly Cys Lys Thr Asp
        115                 120                 125

Leu Arg Thr Asp Leu Ser Thr Leu Met Glu Leu Ser His Gln Lys Gln
    130                 135                 140

Ala Pro Ile Ser Tyr Glu Gln Gly Cys Ala Ile Ala Lys Gln Leu Gly
145                 150                 155                 160

Ala Glu Ile Tyr Leu Glu Gly Ser Ala Phe Thr Ser Glu Lys Ser Ile
                165                 170                 175

His Ser Ile Phe Arg Thr Ala Ser Met Leu Cys Leu Asn Lys Pro Ser
            180                 185                 190

Pro Leu Pro Gln Lys Ser Pro Val Arg Ser Leu Ser Lys Arg Leu Leu
        195                 200                 205

His Leu Pro Ser Arg Ser Glu Leu Ile Ser Ser Thr Phe Lys Lys Glu
```

```
    210                 215                 220

Lys Ala Lys Ser Cys Ser Ile Met
225                 230


<210> SEQ ID NO 9
<211> LENGTH: 744
<212> TYPE: DNA
<213> ORGANISM: Homo sapiens

<400> SEQUENCE: 9

atggagagag ccagtctgat ccagaaggcc aagctggcag agcaggccga acgctatgag     60

gacatggcag ccttcatgaa aggcgccgtg gagaagggcg aggagctctc ctgcgaagag    120

cgaaacctgc tctcagtagc ctataagaac gtggtgggcg gccagagggc tgcctggagg    180

gtgctgtcca gtattgagca gaaaagcaac gaggagggct cggaggagaa ggggcccgag    240

gtgcgtgagt accgggagaa ggtggagact gagctccagg gcgtgtgcga caccgtgctg    300

ggcctgctgg acagccacct catcaaggag gccggggacg ccgagagccg ggtcttctac    360

ctgaagatga agggtgacta ctaccgctac ctggccgagg tggccaccgg tgacgacaag    420

aagcgcatca ttgactcagc ccggtcagcc taccaggagg ccatggacat cagcaagaag    480

gagatgccgc ccaccaaccc catccgcctg ggcctggccc tgaacttttc cgtcttccac    540

tacgagatcg ccaacagccc cgaggaggcc atctctctgg ccaagaccac tttcgacgag    600

gccatggctg atctgcacac cctcagcgag gactcctaca aagacagcac cctcatcatg    660

cagctgctgc gagacaacct gacactgtgg acggccgaca acgccgggga agagggggc    720

gaggctcccc aggagcccca gagc                                           744


<210> SEQ ID NO 10
<211> LENGTH: 248
<212> TYPE: PRT
<213> ORGANISM: Homo sapiens

<400> SEQUENCE: 10

Met Glu Arg Ala Ser Leu Ile Gln Lys Ala Lys Leu Ala Glu Gln Ala
1               5                   10                  15

Glu Arg Tyr Glu Asp Met Ala Ala Phe Met Lys Gly Ala Val Glu Lys
            20                  25                  30

Gly Glu Glu Leu Ser Cys Glu Glu Arg Asn Leu Leu Ser Val Ala Tyr
        35                  40                  45

Lys Asn Val Val Gly Gly Gln Arg Ala Ala Trp Arg Val Leu Ser Ser
    50                  55                  60

Ile Glu Gln Lys Ser Asn Glu Glu Gly Ser Glu Glu Lys Gly Pro Glu
65                  70                  75                  80

Val Arg Glu Tyr Arg Glu Lys Val Glu Thr Glu Leu Gln Gly Val Cys
                85                  90                  95

Asp Thr Val Leu Gly Leu Leu Asp Ser His Leu Ile Lys Glu Ala Gly
            100                 105                 110

Asp Ala Glu Ser Arg Val Phe Tyr Leu Lys Met Lys Gly Asp Tyr Tyr
        115                 120                 125

Arg Tyr Leu Ala Glu Val Ala Thr Gly Asp Asp Lys Lys Arg Ile Ile
    130                 135                 140

Asp Ser Ala Arg Ser Ala Tyr Gln Glu Ala Met Asp Ile Ser Lys Lys
145                 150                 155                 160

Glu Met Pro Pro Thr Asn Pro Ile Arg Leu Gly Leu Ala Leu Asn Phe
                165                 170                 175
```

```
Ser Val Phe His Tyr Glu Ile Ala Asn Ser Pro Glu Glu Ala Ile Ser
            180                 185                 190

Leu Ala Lys Thr Thr Phe Asp Glu Ala Met Ala Asp Leu His Thr Leu
        195                 200                 205

Ser Glu Asp Ser Tyr Lys Asp Ser Thr Leu Ile Met Gln Leu Leu Arg
    210                 215                 220

Asp Asn Leu Thr Leu Trp Thr Ala Asp Asn Ala Gly Glu Glu Gly Gly
225                 230                 235                 240

Glu Ala Pro Gln Glu Pro Gln Ser
                245
```

<210> SEQ ID NO 11
<211> LENGTH: 819
<212> TYPE: DNA
<213> ORGANISM: Homo sapiens

<400> SEQUENCE: 11

```
atgggtcaga aggtcactgg agggatcaag actgtggaca tgagggaccc cacgtacagg     60

cccctgaagc aggagctcca gggtctggat tactgcaagc ccacccggct ggatctgcta    120

ctggacatgc cccctgtgtc ctatgatgtc cagctgctgc attcatggaa caacaacgac    180

cgatcgctca atgtctttgt gaaggaggac gacaagctca tctttcaccg gcatccggtg    240

gcccagagca cggacgctat caggggcaaa gtcgggtata cccgtgggct gcacgtgtgg    300

cagatcacgt gggccatgag acagcggggc acacacgccg tggtgggggt ggcgacggca    360

gacgcccccc tgcactctgt cgggtacaca accctcgtgg ggaataacca cgagtcctgg    420

ggctgggact tggggcgcaa ccggctctac cacgatggca agaaccagcc aagcaaaaca    480

tacccagcct ttctggaacc agatgagaca ttcattgtcc ctgactcctt cctggtagcc    540

ctggacatgg acgacgggac tctgagcttc attgtggatg gacagtacat gggagtggct    600

tttcggggac tcaagggcaa aaaactgtat cctgtagtga gtgccgtctg ggccactgt     660

gagatccgaa tgcgctactt gaacggactc gatcccgagc cgctgccgct catggatttg    720

tgccgtcgct cggtgcgcct ggccctgggg agggagcgcc tgggggagat ccacacgctg    780

ccgctgccgg cttccctcaa ggcctacctc ctctaccag                           819
```

<210> SEQ ID NO 12
<211> LENGTH: 273
<212> TYPE: PRT
<213> ORGANISM: Homo sapiens

<400> SEQUENCE: 12

```
Met Gly Gln Lys Val Thr Gly Gly Ile Lys Thr Val Asp Met Arg Asp
1               5                   10                  15

Pro Thr Tyr Arg Pro Leu Lys Gln Glu Leu Gln Gly Leu Asp Tyr Cys
            20                  25                  30

Lys Pro Thr Arg Leu Asp Leu Leu Leu Asp Met Pro Pro Val Ser Tyr
        35                  40                  45

Asp Val Gln Leu Leu His Ser Trp Asn Asn Asn Asp Arg Ser Leu Asn
    50                  55                  60

Val Phe Val Lys Glu Asp Asp Lys Leu Ile Phe His Arg His Pro Val
65                  70                  75                  80

Ala Gln Ser Thr Asp Ala Ile Arg Gly Lys Val Gly Tyr Thr Arg Gly
                85                  90                  95

Leu His Val Trp Gln Ile Thr Trp Ala Met Arg Gln Arg Gly Thr His
            100                 105                 110
```

```
Ala Val Val Gly Val Ala Thr Ala Asp Ala Pro Leu His Ser Val Gly
        115                 120                 125

Tyr Thr Thr Leu Val Gly Asn Asn His Glu Ser Trp Gly Trp Asp Leu
    130                 135                 140

Gly Arg Asn Arg Leu Tyr His Asp Gly Lys Asn Gln Pro Ser Lys Thr
145                 150                 155                 160

Tyr Pro Ala Phe Leu Glu Pro Asp Glu Thr Phe Ile Val Pro Asp Ser
                165                 170                 175

Phe Leu Val Ala Leu Asp Met Asp Asp Gly Thr Leu Ser Phe Ile Val
            180                 185                 190

Asp Gly Gln Tyr Met Gly Val Ala Phe Arg Gly Leu Lys Gly Lys Lys
        195                 200                 205

Leu Tyr Pro Val Val Ser Ala Val Trp Gly His Cys Glu Ile Arg Met
    210                 215                 220

Arg Tyr Leu Asn Gly Leu Asp Pro Glu Pro Leu Pro Leu Met Asp Leu
225                 230                 235                 240

Cys Arg Arg Ser Val Arg Leu Ala Leu Gly Arg Glu Arg Leu Gly Glu
                245                 250                 255

Ile His Thr Leu Pro Leu Pro Ala Ser Leu Lys Ala Tyr Leu Leu Tyr
            260                 265                 270

Gln
```

```
<210> SEQ ID NO 13
<211> LENGTH: 2370
<212> TYPE: DNA
<213> ORGANISM: Homo sapiens

<400> SEQUENCE: 13

atggctgaac aagtccttcc tcaggctttg tatttgagca atatgcggaa agctgtgaag      60

atacgggaga gaactccaga agacattttt aaacctacta atgggatcat tcatcatttt     120

aaaaccatgc accgatacac actggaaatg ttcagaactt gccagttttg tcctcagttt     180

cgggagatca tccacaaagc cctcatcgac agaaacatcc aggccaccct ggaaagccag     240

aagaaactca actggtgtcg agaagtccgg aagcttgtgg cgctgaaaac gaacggtgac     300

ggcaattgcc tcatgcatgc cacttctcag tacatgtggg gcgttcagga cacagacttg     360

gtactgagga aggcgctgtt cagcacgctc aaggaaacag acacacgcaa ctttaaattc     420

cgctggcaac tggagtctct caaatctcag gaatttgttg aaacggggct ttgctatgat     480

actcggaact ggaatgatga atgggacaat cttatcaaaa tggcttccac agacacaccc     540

atggcccgaa gtggacttca gtacaactca ctggaagaaa tacacatatt tgtcctttgc     600

aacatcctca gaaggccaat cattgtcatt tcagacaaaa tgctaagaag tttggaatca     660

ggttccaatt tcgccccttt gaaagtgggt ggaatttact tgcctctcca ctggcctgcc     720

caggaatgct acagataccc cattgttctc ggctatgaca gccatcattt tgtacccttg     780

gtgaccctga aggacagtgg gcctgaaatc cgagctgttc cacttgttaa cagagaccgg     840

ggaagatttg aagacttaaa agttcacttt ttgacagatc ctgaaaatga gatgaaggag     900

aagctcttaa aagagtactt aatggtgata gaaatccccg tccaaggctg ggaccatggc     960

acaactcatc tcatcaatgc cgcaaagttg gatgaagcta acttaccaaa agaaatcaat    1020

ctggtagatg attactttga acttgttcag catgagtaca agaaatggca ggaaaacagc    1080

gagcagggga ggagagaggg gcacgcccag aatcccatgg aaccttccgt gccccagctt    1140

tctctcatgg atgtaaaatg tgaaacgccc aactgcccct tcttcatgtc tgtgaacacc    1200
```

```
cagcctttat gccatgagtg ctcagagagg cggcaaaaga atcaaaacaa actcccaaag   1260

ctgaactcca agccgggccc tgaggggctc cctggcatgg cgctcggggc ctctcgggga   1320

gaagcctatg agcccttggc gtggaaccct gaggagtcca ctgggggggcc tcattcggcc   1380

ccaccgacag cacccagccc ttttctgttc agtgagacca ctgccatgaa gtgcaggagc   1440

cccggctgcc ccttcacact gaatgtgcag cacaacggat tttgtgaacg ttgccacaac   1500

gcccggcaac ttcacgccag ccacgcccca gaccacacaa ggcacttgga tcccgggaag   1560

tgccaagcct gcctccagga tgttaccagg acatttaatg ggatctgcag tacttgcttc   1620

aaaaggacta cagcagaggc ctcctccagc ctcagcacca gcctccctcc ttcctgtcac   1680

cagcgttcca agtcagatcc ctcgcggctc gtccggagcc cctccccgca ttcttgccac   1740

agagctggaa acgacgcccc tgctggctgc ctgtctcaag ctgcacggac tcctggggac   1800

aggacgggga cgagcaagtg cagaaaagcc ggctgcgtgt attttgggac tccagaaaac   1860

aagggctttt gcacactgtg tttcatcgag tacagagaaa acaaacattt tgctgctgcc   1920

tcagggaaag tcagtcccac agcgtccagg ttccagaaca ccattccgtg cctggggagg   1980

gaatgcggca cccttggaag caccatgttt gaaggatact gccagaagtg tttcattgaa   2040

gctcagaatc agagatttca tgaggccaaa aggacagaag agcaactgag atcgagccag   2100

cgcagagatg tgcctcgaac cacacaaagc acctcaaggc ccaagtgcgc ccgggcctcc   2160

tgcaagaaca tcctggcctg ccgcagcgag gagctctgca tggagtgtca gcatcccaac   2220

cagaggatgg gccctggggc ccaccggggt gagcctgccc ccgaagaccc ccccaagcag   2280

cgttgccggg cccccgcctg tgatcatttt ggcaatgcca agtgcaacgg ctactgcaac   2340

gaatgctttc agttcaagca gatgtatggc                                     2370
```

<210> SEQ ID NO 14
<211> LENGTH: 790
<212> TYPE: PRT
<213> ORGANISM: Homo sapiens

<400> SEQUENCE: 14

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
            20                  25                  30

Thr Asn Gly Ile Ile His His Phe Lys Thr Met His Arg Tyr Thr Leu
        35                  40                  45

Glu Met Phe Arg Thr Cys Gln Phe Cys Pro Gln Phe Arg Glu Ile Ile
    50                  55                  60

His Lys Ala Leu Ile Asp Arg Asn Ile Gln Ala Thr Leu Glu Ser Gln
65                  70                  75                  80

Lys Lys Leu Asn Trp Cys Arg Glu Val Arg Lys Leu Val Ala Leu Lys
                85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
    130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175
```

```
Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
        195                 200                 205

Val Ile Ser Asp Lys Met Leu Arg Ser Leu Glu Ser Gly Ser Asn Phe
    210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
        275                 280                 285

His Phe Leu Thr Asp Pro Glu Asn Glu Met Lys Glu Lys Leu Leu Lys
    290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
        355                 360                 365

Ala Gln Asn Pro Met Glu Pro Ser Val Pro Gln Leu Ser Leu Met Asp
    370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
        435                 440                 445

Asn Pro Glu Glu Ser Thr Gly Gly Pro His Ser Ala Pro Pro Thr Ala
    450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
            500                 505                 510

Thr Arg His Leu Asp Pro Gly Lys Cys Gln Ala Cys Leu Gln Asp Val
        515                 520                 525

Thr Arg Thr Phe Asn Gly Ile Cys Ser Thr Cys Phe Lys Arg Thr Thr
    530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
```

```
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
            660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Arg Asp Val
    690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
            740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790


<210> SEQ ID NO 15
<211> LENGTH: 831
<212> TYPE: DNA
<213> ORGANISM: Homo sapiens

<400> SEQUENCE: 15

atgatcatct taatttactt atttctcttg ctatgggaag acactcaagg atggggattc      60

aaggatggaa tttttcataa ctccatatgg cttgaacgag cagccggtgt gtaccacaga     120

gaagcacggt ctggcaaata caagctcacc tacgcagaag ctaaggcggt gtgtgaattt     180

gaaggcggcc atctcgcaac ttacaagcag ctagaggcag ccagaaaaat tggatttcat     240

gtctgtgctg ctggatggat ggctaagggc agagttggat accccattgt gaagccaggg     300

cccaactgtg gatttggaaa aactggcatt attgattatg gaatccgtct caataggagt     360

gaaagatggg atgcctattg ctacaaccca cacgcaaagg agtgtggtgg cgtctttaca     420

gatccaaagc aaatttttaa atctccaggc ttcccaaatg agtacgaaga taaccaaatc     480

tgctactggc acattagact caagtatggt cagcgtattc acctgagttt tttagatttt     540

gaccttgaag atgacccagg ttgcttggct gattatgttg aaatatatga cagttacgat     600

gatgtccatg gctttgtggg aagatactgt ggagatgagc ttccagatga catcatcagt     660

acaggaaatg tcatgacctt gaagtttcta agtgatgctt cagtgacagc tggaggtttc     720

caaatcaaat atgttgcaat ggatcctgta tccaaatcca gtcaaggaaa aaatacaagt     780

actacttcta ctggaaataa aaacttttta gctggaagat ttagccactt a              831


<210> SEQ ID NO 16
<211> LENGTH: 277
<212> TYPE: PRT
<213> ORGANISM: Homo sapiens
```

<400> SEQUENCE: 16

```
Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275
```

<210> SEQ ID NO 17
<211> LENGTH: 468
<212> TYPE: DNA
<213> ORGANISM: Homo sapiens

<400> SEQUENCE: 17

```
atgtgtcact ctcgcagctg ccacccgacc atgaccatcc tgcaggcccc gaccccggcc     60

ccctccacca tcccgggacc ccggcggggc tccggtcctg agatcttcac cttcgaccct    120

ctcccggagc ccgcagcggc ccctgccggg cgccccagcg cctctcgcgg gcaccgaaag    180

cgcagccgca gggttctcta ccctcgagtg gtccggcgcc agctgccagt cgaggaaccg    240

aacccagcca aaaggcttct ctttctgctg ctcaccatcg tcttctgcca gatcctgatg    300

gctgaagagg gtgtgccggc gcccctgcct ccagaggacg cccctaacgc cgcatccctg    360

gcgcccaccc ctgtgtcccc cgtcctcgag ccctttaatc tgacttcgga gccctcggac    420

tacgctctgg acctcagcac tttcctccag caacacccgg ccgccttc                 468
```

<210> SEQ ID NO 18
<211> LENGTH: 156
<212> TYPE: PRT
<213> ORGANISM: Homo sapiens

<400> SEQUENCE: 18

```
Met Cys His Ser Arg Ser Cys His Pro Thr Met Thr Ile Leu Gln Ala
1               5                   10                  15

Pro Thr Pro Ala Pro Ser Thr Ile Pro Gly Pro Arg Arg Gly Ser Gly
            20                  25                  30

Pro Glu Ile Phe Thr Phe Asp Pro Leu Pro Glu Pro Ala Ala Ala Pro
        35                  40                  45

Ala Gly Arg Pro Ser Ala Ser Arg Gly His Arg Lys Arg Ser Arg Arg
    50                  55                  60

Val Leu Tyr Pro Arg Val Val Arg Arg Gln Leu Pro Val Glu Glu Pro
65                  70                  75                  80

Asn Pro Ala Lys Arg Leu Leu Phe Leu Leu Leu Thr Ile Val Phe Cys
                85                  90                  95

Gln Ile Leu Met Ala Glu Glu Gly Val Pro Ala Pro Leu Pro Pro Glu
            100                 105                 110

Asp Ala Pro Asn Ala Ala Ser Leu Ala Pro Thr Pro Val Ser Pro Val
        115                 120                 125

Leu Glu Pro Phe Asn Leu Thr Ser Glu Pro Ser Asp Tyr Ala Leu Asp
    130                 135                 140

Leu Ser Thr Phe Leu Gln Gln His Pro Ala Ala Phe
145                 150                 155
```

<210> SEQ ID NO 19
<211> LENGTH: 495
<212> TYPE: DNA
<213> ORGANISM: Homo sapiens

<400> SEQUENCE: 19

```
atgactttgg aggaattctc ggctggagag cagaagaccg aaaggatgga taaggtgggg      60

gatgccctgg aggaagtgct cagcaaagcc ctgagtcagc gcacgatcac tgtcggggtg     120

tacgaagcgg ccaagctgct caacgtcgac cccgataacg tggtgttgtg cctgctggcg     180

gcggacgagg acgacgacag agatgtggct ctgcagatcc acttcaccct gatccaggcg     240

ttttgctgcg agaacgacat caacatcctg cgcgtcagca acccgggccg gctggcggag     300

ctcctgctct tggagaccga cgctggcccc gcggcgagcg agggcgccga gcagcccccg     360

gacctgcact gcgtgctggt gacgaatcca cattcatctc aatggaagga tcctgcctta     420

agtcaactta tttgtttttg ccgggaaagt cgctacatgg atcaatgggt tccagtgatt     480

aatctccctg aacgg                                                      495
```

<210> SEQ ID NO 20
<211> LENGTH: 165
<212> TYPE: PRT
<213> ORGANISM: Homo sapiens

<400> SEQUENCE: 20

```
Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
            20                  25                  30

Gln Arg Thr Ile Thr Val Gly Val Tyr Glu Ala Ala Lys Leu Leu Asn
        35                  40                  45
```

```
Val Asp Pro Asp Asn Val Val Leu Cys Leu Leu Ala Ala Asp Glu Asp
    50                  55                  60

Asp Asp Arg Asp Val Ala Leu Gln Ile His Phe Thr Leu Ile Gln Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Leu Glu Thr Asp Ala Gly Pro Ala Ala
            100                 105                 110

Ser Glu Gly Ala Glu Gln Pro Pro Asp Leu His Cys Val Leu Val Thr
        115                 120                 125

Asn Pro His Ser Ser Gln Trp Lys Asp Pro Ala Leu Ser Gln Leu Ile
    130                 135                 140

Cys Phe Cys Arg Glu Ser Arg Tyr Met Asp Gln Trp Val Pro Val Ile
145                 150                 155                 160

Asn Leu Pro Glu Arg
                165


<210> SEQ ID NO 21
<211> LENGTH: 480
<212> TYPE: DNA
<213> ORGANISM: Homo sapiens

<400> SEQUENCE: 21

atgacgctgg aagagctcgt ggcgtgcgac aacgcggcgc agaagatgca gacggtgacc     60

gccgcggtgg aggagctttt ggtggccgct cagcgccagg atcgcctcac agtgggggtg    120

tacgagtcgg ccaagttgat gaatgtggac ccagacagcg tggtcctctg cctcttggcc    180

attgacgagg aggaggagga tgacatcgcc ctgcaaatcc acttcacgct catccagtcc    240

ttctgctgtg acaacgacat caacatcgtg cgggtgtcgg gcatgcagcg cctggcgcag    300

ctcctgggag agccggccga gacccagggc accaccgagg cccgagacct gcattgtctc    360

ctggtcacga accctcacac ggacgcctgg aagagccacg gcttggtgga ggtggccagc    420

tactgcgaag aaagccgggg caacaaccag tgggtcccct acatctctct tcaggaacgc    480


<210> SEQ ID NO 22
<211> LENGTH: 160
<212> TYPE: PRT
<213> ORGANISM: Homo sapiens

<400> SEQUENCE: 22

Met Thr Leu Glu Glu Leu Val Ala Cys Asp Asn Ala Ala Gln Lys Met
1               5                   10                  15

Gln Thr Val Thr Ala Ala Val Glu Glu Leu Leu Val Ala Ala Gln Arg
            20                  25                  30

Gln Asp Arg Leu Thr Val Gly Val Tyr Glu Ser Ala Lys Leu Met Asn
        35                  40                  45

Val Asp Pro Asp Ser Val Val Leu Cys Leu Leu Ala Ile Asp Glu Glu
    50                  55                  60

Glu Glu Asp Asp Ile Ala Leu Gln Ile His Phe Thr Leu Ile Gln Ser
65                  70                  75                  80

Phe Cys Cys Asp Asn Asp Ile Asn Ile Val Arg Val Ser Gly Met Gln
                85                  90                  95

Arg Leu Ala Gln Leu Leu Gly Glu Pro Ala Glu Thr Gln Gly Thr Thr
            100                 105                 110

Glu Ala Arg Asp Leu His Cys Leu Leu Val Thr Asn Pro His Thr Asp
        115                 120                 125
```

```
Ala Trp Lys Ser His Gly Leu Val Glu Val Ala Ser Tyr Cys Glu Glu
    130                 135                 140

Ser Arg Gly Asn Asn Gln Trp Val Pro Tyr Ile Ser Leu Gln Glu Arg
145                 150                 155                 160
```

<210> SEQ ID NO 23
<211> LENGTH: 531
<212> TYPE: DNA
<213> ORGANISM: Homo sapiens

<400> SEQUENCE: 23

```
atggaaatct gcagaggcct ccgcagtcac ctaatcactc tcctcctctt cctgttccat      60

tcagagacga tctgccgacc ctctgggaga aaatccagca agatgcaagc cttcagaatc     120

tgggatgtta accagaagac cttctatctg aggaacaacc aactagttgc tggatacttg     180

caaggaccaa atgtcaattt agaagaaaag atagatgtgg tacccattga gcctcatgct     240

ctgttcttgg gaatccatgg agggaagatg tgcctgtcct gtgtcaagtc tggtgatgag     300

accagactcc agctggaggc agttaacatc actgacctga gcgagaacag aaagcaggac     360

aagcgcttcg ccttcatccg ctcagacagc ggccccacca ccagttttga gtctgccgcc     420

tgccccggtt ggttcctctg cacagcgatg gaagctgacc agcccgtcag cctcaccaat     480

atgcctgacg aaggcgtcat ggtcaccaaa ttctacttcc aggaggacga g              531
```

<210> SEQ ID NO 24
<211> LENGTH: 177
<212> TYPE: PRT
<213> ORGANISM: Homo sapiens

<400> SEQUENCE: 24

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 25
<211> LENGTH: 594
<212> TYPE: DNA

<213> ORGANISM: Homo sapiens

<400> SEQUENCE: 25

```
atgaccctgc ggtgccttga gccctccggg aatggcgggg aagggacgcg gagccagtgg     60

gggaccgcgg ggtcggcgga ggagccatcc ccgcaggcgg cgcgtctggc gaaggccctg    120

cgggagctcg gtcagacagg atggtactgg ggaagtatga ctgttaatga agccaaagag    180

aaattaaaag aggcaccaga aggaactttc ttgattagag atagctcgca ttcagactac    240

ctactaacaa tatctgttaa aacatcagct ggaccaacta atcttcgaat cgaataccaa    300

gacggaaaat tcagattgga ctctatcata tgtgtcaaat ccaagcttaa acaatttgac    360

agtgtggttc atctgatcga ctactatgtt cagatgtgca aggataagcg gacaggtcca    420

gaagcccccc ggaacggcac tgttcacctt tatctgacca aaccgctcta cacgtcagca    480

ccatctctgc agcatctctg taggctcacc attaacaaat gtaccggtgc catctgggga    540

ctgcctttac caacaagact aaaagattac ttggaagaat ataaattcca ggta          594
```

<210> SEQ ID NO 26
<211> LENGTH: 198
<212> TYPE: PRT
<213> ORGANISM: Homo sapiens

<400> SEQUENCE: 26

```
Met Thr Leu Arg Cys Leu Glu Pro Ser Gly Asn Gly Gly Glu Gly Thr
1               5                   10                  15

Arg Ser Gln Trp Gly Thr Ala Gly Ser Ala Glu Glu Pro Ser Pro Gln
            20                  25                  30

Ala Ala Arg Leu Ala Lys Ala Leu Arg Glu Leu Gly Gln Thr Gly Trp
        35                  40                  45

Tyr Trp Gly Ser Met Thr Val Asn Glu Ala Lys Glu Lys Leu Lys Glu
    50                  55                  60

Ala Pro Glu Gly Thr Phe Leu Ile Arg Asp Ser Ser His Ser Asp Tyr
65                  70                  75                  80

Leu Leu Thr Ile Ser Val Lys Thr Ser Ala Gly Pro Thr Asn Leu Arg
                85                  90                  95

Ile Glu Tyr Gln Asp Gly Lys Phe Arg Leu Asp Ser Ile Ile Cys Val
            100                 105                 110

Lys Ser Lys Leu Lys Gln Phe Asp Ser Val Val His Leu Ile Asp Tyr
        115                 120                 125

Tyr Val Gln Met Cys Lys Asp Lys Arg Thr Gly Pro Glu Ala Pro Arg
    130                 135                 140

Asn Gly Thr Val His Leu Tyr Leu Thr Lys Pro Leu Tyr Thr Ser Ala
145                 150                 155                 160

Pro Ser Leu Gln His Leu Cys Arg Leu Thr Ile Asn Lys Cys Thr Gly
                165                 170                 175

Ala Ile Trp Gly Leu Pro Leu Pro Thr Arg Leu Lys Asp Tyr Leu Glu
            180                 185                 190

Glu Tyr Lys Phe Gln Val
        195
```

<210> SEQ ID NO 27
<211> LENGTH: 675
<212> TYPE: DNA
<213> ORGANISM: Homo sapiens

<400> SEQUENCE: 27

```
atggtcaccc acagcaagtt tcccgccgcc gggatgagcc gcccccctgga caccagcctg     60
```

```
cgcctcaaga ccttcagctc caagagcgag taccagctgg tggtgaacgc agtgcgcaag    120

ctgcaggaga gcggcttcta ctggagcgca gtgaccggcg gcgaggcgaa cctgctgctc    180

agtgccgagc ccgccggcac ctttctgatc cgcgacagct cggaccagcg ccacttcttc    240

acgctcagcg tcaagaccca gtctgggacc aagaacctgc gcatccagtg tgaggggggc    300

agcttctctc tgcagagcga tccccggagc acgcagcccg tgccccgctt cgactgcgtg    360

ctcaagctgg tgtaccacta catgccgccc cctggagccc cctccttccc ctcgccacct    420

actgaaccct cctccgaggt gcccgagcag ccgtctgccc agccactccc tgggagtccc    480

cccagaagag cctattacat ctactccggg ggcgagaaga tcccccctggt gttgagccgg    540

cccctctcct ccaacgtggc cactcttcag catctctgtc ggaagaccgt caacggccac    600

ctggactcct atgagaaagt cacccagctg ccggggccca ttcgggagtt cctggaccag    660

tacgatgccc cgctt                                                      675
```

<210> SEQ ID NO 28
<211> LENGTH: 225
<212> TYPE: PRT
<213> ORGANISM: Homo sapiens

<400> SEQUENCE: 28

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val Tyr His Tyr Met
        115                 120                 125

Pro Pro Pro Gly Ala Pro Ser Phe Pro Ser Pro Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225
```

<210> SEQ ID NO 29
<211> LENGTH: 1524
<212> TYPE: DNA

<213> ORGANISM: Homo sapiens

<400> SEQUENCE: 29

```
atgaactgcc agcagctgtg gctgggcttc ctactcccca tgacagtctc aggccgggtc     60
ctggggcttg cagaggtggc gcccgtggac tacctgtcac aatatgggta cctacagaag    120
cctctagaag gatctaataa cttcaagcca gaagatatca ccgaggctct gagagctttt    180
caggaagcat ctgaacttcc agtctcaggt cagctggatg atgccacaag ggcccgcatg    240
aggcagcctc gttgtggcct agaggatccc ttcaaccaga agacccttaa atacctgttg    300
ctgggccgct ggagaaagaa gcacctgact ttccgcatct tgaacctgcc ctccaccctt    360
ccaccccaca cagcccgggc agccctgcgt caagccttcc aggactggag caatgtggct    420
cccttgacct tccaagaggt gcaggctggt gcggctgaca tccgcctctc cttccatggc    480
cgccaaagct cgtactgttc caatactttt gatgggcctg ggagagtcct ggcccatgcc    540
gacatcccag agctgggcag tgtgcacttc gacgaagacg agttctggac tgaggggacc    600
taccgtgggg tgaacctgcg catcattgca gcccatgaag tgggccatgc tctggggctt    660
gggcactccc gatattccca ggccctcatg gccccagtct acgagggcta ccggccccac    720
tttaagctgc acccagatga tgtggcaggg atccaggctc tctatggcaa gaagagtcca    780
gtgataaggg atgaggaaga agaagagaca gagctgccca ctgtgccccc agtgcccaca    840
gaacccagtc ccatgccaga cccttgcagt agtgaactgg atgccatgat gctggggccc    900
cgtgggaaga cctatgcttt caaggggggac tatgtgtgga ctgtatcaga ttcaggaccg    960
ggcccccttgt tccgagtgtc tgccctttgg gaggggctcc ccggaaacct ggatgctgct   1020
gtctactcgc ctcgaacaca atggattcac ttctttaagg gagacaaggt gtggcgctac   1080
attaatttca agatgtctcc tggcttcccc aagaagctga atagggtaga acctaacctg   1140
gatgcagctc tctattggcc tctcaaccaa aaggtgttcc tctttaaggg ctccgggtac   1200
tggcagtggg acgagctagc ccgaactgac ttcagcagct accccaaacc aatcaagggt   1260
ttgtttacgg gagtgccaaa ccagccctcg gctgctatga gttggcaaga tggccgagtc   1320
tacttcttca agggcaaagt ctactggcgc ctcaaccagc agcttcgagt agagaaaggc   1380
tatcccagaa atatttccca caactggatg cactgtcgtc cccggactat agacactacc   1440
ccatcaggtg ggaataccac tccctcaggt acgggcataa ccttggatac cactctctca   1500
gccacagaaa ccacgtttga atac                                           1524
```

<210> SEQ ID NO 30
<211> LENGTH: 508
<212> TYPE: PRT
<213> ORGANISM: Homo sapiens

<400> SEQUENCE: 30

```
Met Asn Cys Gln Gln Leu Trp Leu Gly Phe Leu Leu Pro Met Thr Val
1               5                   10                  15

Ser Gly Arg Val Leu Gly Leu Ala Glu Val Ala Pro Val Asp Tyr Leu
            20                  25                  30

Ser Gln Tyr Gly Tyr Leu Gln Lys Pro Leu Glu Gly Ser Asn Asn Phe
        35                  40                  45

Lys Pro Glu Asp Ile Thr Glu Ala Leu Arg Ala Phe Gln Glu Ala Ser
    50                  55                  60

Glu Leu Pro Val Ser Gly Gln Leu Asp Asp Ala Thr Arg Ala Arg Met
65                  70                  75                  80

Arg Gln Pro Arg Cys Gly Leu Glu Asp Pro Phe Asn Gln Lys Thr Leu
```

```
                85                  90                  95

Lys Tyr Leu Leu Leu Gly Arg Trp Arg Lys Lys His Leu Thr Phe Arg
            100                 105                 110

Ile Leu Asn Leu Pro Ser Thr Leu Pro Pro His Thr Ala Arg Ala Ala
        115                 120                 125

Leu Arg Gln Ala Phe Gln Asp Trp Ser Asn Val Ala Pro Leu Thr Phe
    130                 135                 140

Gln Glu Val Gln Ala Gly Ala Ala Asp Ile Arg Leu Ser Phe His Gly
145                 150                 155                 160

Arg Gln Ser Ser Tyr Cys Ser Asn Thr Phe Asp Gly Pro Gly Arg Val
                165                 170                 175

Leu Ala His Ala Asp Ile Pro Glu Leu Gly Ser Val His Phe Asp Glu
            180                 185                 190

Asp Glu Phe Trp Thr Glu Gly Thr Tyr Arg Gly Val Asn Leu Arg Ile
        195                 200                 205

Ile Ala Ala His Glu Val Gly His Ala Leu Gly Leu Gly His Ser Arg
    210                 215                 220

Tyr Ser Gln Ala Leu Met Ala Pro Val Tyr Glu Gly Tyr Arg Pro His
225                 230                 235                 240

Phe Lys Leu His Pro Asp Asp Val Ala Gly Ile Gln Ala Leu Tyr Gly
                245                 250                 255

Lys Lys Ser Pro Val Ile Arg Asp Glu Glu Glu Glu Glu Thr Glu Leu
            260                 265                 270

Pro Thr Val Pro Pro Val Pro Thr Glu Pro Ser Pro Met Pro Asp Pro
        275                 280                 285

Cys Ser Ser Glu Leu Asp Ala Met Met Leu Gly Pro Arg Gly Lys Thr
    290                 295                 300

Tyr Ala Phe Lys Gly Asp Tyr Val Trp Thr Val Ser Asp Ser Gly Pro
305                 310                 315                 320

Gly Pro Leu Phe Arg Val Ser Ala Leu Trp Glu Gly Leu Pro Gly Asn
                325                 330                 335

Leu Asp Ala Ala Val Tyr Ser Pro Arg Thr Gln Trp Ile His Phe Phe
            340                 345                 350

Lys Gly Asp Lys Val Trp Arg Tyr Ile Asn Phe Lys Met Ser Pro Gly
        355                 360                 365

Phe Pro Lys Lys Leu Asn Arg Val Glu Pro Asn Leu Asp Ala Ala Leu
    370                 375                 380

Tyr Trp Pro Leu Asn Gln Lys Val Phe Leu Phe Lys Gly Ser Gly Tyr
385                 390                 395                 400

Trp Gln Trp Asp Glu Leu Ala Arg Thr Asp Phe Ser Ser Tyr Pro Lys
                405                 410                 415

Pro Ile Lys Gly Leu Phe Thr Gly Val Pro Asn Gln Pro Ser Ala Ala
            420                 425                 430

Met Ser Trp Gln Asp Gly Arg Val Tyr Phe Phe Lys Gly Lys Val Tyr
        435                 440                 445

Trp Arg Leu Asn Gln Gln Leu Arg Val Glu Lys Gly Tyr Pro Arg Asn
    450                 455                 460

Ile Ser His Asn Trp Met His Cys Arg Pro Arg Thr Ile Asp Thr Thr
465                 470                 475                 480

Pro Ser Gly Gly Asn Thr Thr Pro Ser Gly Thr Gly Ile Thr Leu Asp
                485                 490                 495

Thr Thr Leu Ser Ala Thr Glu Thr Thr Phe Glu Tyr
            500                 505
```

<210> SEQ ID NO 31
<211> LENGTH: 942
<212> TYPE: DNA
<213> ORGANISM: Homo sapiens

<400> SEQUENCE: 31

```
atggggctgg aggcggcgcg cgagctggag tgcgcggcgc tgggcacgct gctgcgggat     60

ccgcgggagg cggaacgcac gctgctgctg gactgccgcc ccttcctggc cttctgccgg    120

cgccacgtgc gcgccgcgcg gccagtgcct tggaacgcgc tgctgcggcg ccgcgcgcgc    180

ggccctcctg ccgccgttct cgcctgcctg ctgcccgacc gcgcgctgcg gacgcgcctg    240

gtccgcgggg agctggcgcg ggccgtggtg ctggacgagg gcagtgcctc ggtggcggag    300

ctccggcccg acagcccggc tcatgtgctg ctggccgcgc tgctgcacga gacccgcgcg    360

gggcccactg ccgtgtactt cctgcgagga ggcttcgacg gcttccaggg ctgctgtccc    420

gatctgtgct ctgaggcccc cgcccctgcg ctgccgccaa caggggacaa aaccagccgc    480

tccgactcca gggctcctgt ctacgaccag ggtggccctg tggagatctt gccctacctg    540

ttcctgggca gctgcagtca ctcgtcagac ctgcaggggc tgcaggcctg tggcatcaca    600

gccgtcctca acgtgtccgc cagctgcccc aaccactttg agggcctttt ccgctacaag    660

agtatccctg tggaggacaa ccagatggtg gagatcagtg cctggttcca ggaggccata    720

ggcttcattg actgggtgaa gaacagcgga ggccgggtgc tggtgcactg ccaggcgggt    780

atctcgcgct ctgccaccat ctgtctggca tacctcatgc agagtcgccg tgtgcggctg    840

gacgaggcct ttgacttcgt taagcagcgc cggggggtca tctcccccaa cttcagtttc    900

atggggcagc tgctgcagtt tgagacccag gtgctgtgtc ac                       942
```

<210> SEQ ID NO 32
<211> LENGTH: 314
<212> TYPE: PRT
<213> ORGANISM: Homo sapiens

<400> SEQUENCE: 32

```
Met Gly Leu Glu Ala Ala Arg Glu Leu Glu Cys Ala Ala Leu Gly Thr
1               5                   10                  15

Leu Leu Arg Asp Pro Arg Glu Ala Glu Arg Thr Leu Leu Leu Asp Cys
            20                  25                  30

Arg Pro Phe Leu Ala Phe Cys Arg Arg His Val Arg Ala Ala Arg Pro
        35                  40                  45

Val Pro Trp Asn Ala Leu Leu Arg Arg Arg Ala Arg Gly Pro Pro Ala
    50                  55                  60

Ala Val Leu Ala Cys Leu Leu Pro Asp Arg Ala Leu Arg Thr Arg Leu
65                  70                  75                  80

Val Arg Gly Glu Leu Ala Arg Ala Val Val Leu Asp Glu Gly Ser Ala
                85                  90                  95

Ser Val Ala Glu Leu Arg Pro Asp Ser Pro Ala His Val Leu Leu Ala
            100                 105                 110

Ala Leu Leu His Glu Thr Arg Ala Gly Pro Thr Ala Val Tyr Phe Leu
        115                 120                 125

Arg Gly Gly Phe Asp Gly Phe Gln Gly Cys Cys Pro Asp Leu Cys Ser
    130                 135                 140

Glu Ala Pro Ala Pro Ala Leu Pro Pro Thr Gly Asp Lys Thr Ser Arg
145                 150                 155                 160

Ser Asp Ser Arg Ala Pro Val Tyr Asp Gln Gly Gly Pro Val Glu Ile
                165                 170                 175
```

```
Leu Pro Tyr Leu Phe Leu Gly Ser Cys Ser His Ser Ser Asp Leu Gln
            180                 185                 190

Gly Leu Gln Ala Cys Gly Ile Thr Ala Val Leu Asn Val Ser Ala Ser
        195                 200                 205

Cys Pro Asn His Phe Glu Gly Leu Phe Arg Tyr Lys Ser Ile Pro Val
    210                 215                 220

Glu Asp Asn Gln Met Val Glu Ile Ser Ala Trp Phe Gln Glu Ala Ile
225                 230                 235                 240

Gly Phe Ile Asp Trp Val Lys Asn Ser Gly Gly Arg Val Leu Val His
                245                 250                 255

Cys Gln Ala Gly Ile Ser Arg Ser Ala Thr Ile Cys Leu Ala Tyr Leu
            260                 265                 270

Met Gln Ser Arg Arg Val Arg Leu Asp Glu Ala Phe Asp Phe Val Lys
        275                 280                 285

Gln Arg Arg Gly Val Ile Ser Pro Asn Phe Ser Phe Met Gly Gln Leu
    290                 295                 300

Leu Gln Phe Glu Thr Gln Val Leu Cys His
305                 310


<210> SEQ ID NO 33
<211> LENGTH: 1152
<212> TYPE: DNA
<213> ORGANISM: Homo sapiens

<400> SEQUENCE: 33

atgaaggtca cgtcgctcga cgggcgccag ctgcgcaaga tgctccgcaa ggaggcggcg      60

gcgcgctgcg tggtgctcga ctgccggccc tatctggcct tcgctgcctc gaacgtgcgc     120

ggctcgctca acgtcaacct caactcggtg gtgctgcggc gggcccgggg cggcgcggtg     180

tcggcgcgct acgtgctgcc cgacgaggcg gcgcgcgcgc ggctcctgca ggagggcggc     240

ggcggcgtcg cggccgtggt ggtgctggac cagggcagcc gccactggca gaagctgcga     300

gaggagagcg ccgcgcgtgt cgtcctcacc tcgctactcg cttgcctacc cgccggcccg     360

cgggtctact tcctcaaagg gggatatgag actttctact cggaatatcc tgagtgttgc     420

gtggatgtaa aacccatttc acaagagaag attgagagtg agagagccct catcagccag     480

tgtggaaaac cagtggtaaa tgtcagctac aggccagctt atgaccaggg tggcccagtt     540

gaaatccttc ccttcctcta ccttggaagt gcctaccatg catccaagtg cgagttcctc     600

gccaacttgc acatcacagc cctgctgaat gtctcccgac ggacctccga ggcctgcatg     660

acccacctac actacaaatg gatccctgtg gaagacagcc acacggctga cattagctcc     720

cactttcaag aagcaataga cttcattgac tgtgtcaggg aaaagggagg caaggtcctg     780

gtccactgtg aggctgggat ctcccgttca cccaccatct gcatggctta ccttatgaag     840

accaagcagt tccgcctgaa ggaggccttc gattacatca agcagaggag gagcatggtc     900

tcgcccaact ttggcttcat gggccagctc ctgcagtacg aatctgagat cctgccctcc     960

acgcccaacc cccagcctcc ctcctgccaa ggggaggcag caggctcttc actgataggc    1020

catttgcaga cactgagccc tgacatgcag ggtgcctact gcacattccc tgcctcggtg    1080

ctggcaccgg tgcctaccca ctcaacagtc tcagagctca gcagaagccc tgtggcaacg    1140

gccacatcct gc                                                        1152


<210> SEQ ID NO 34
<211> LENGTH: 384
<212> TYPE: PRT
```

<213> ORGANISM: Homo sapiens

<400> SEQUENCE: 34

```
Met Lys Val Thr Ser Leu Asp Gly Arg Gln Leu Arg Lys Met Leu Arg
1               5                   10                  15

Lys Glu Ala Ala Ala Arg Cys Val Val Leu Asp Cys Arg Pro Tyr Leu
            20                  25                  30

Ala Phe Ala Ala Ser Asn Val Arg Gly Ser Leu Asn Val Asn Leu Asn
        35                  40                  45

Ser Val Val Leu Arg Arg Ala Arg Gly Gly Ala Val Ser Ala Arg Tyr
    50                  55                  60

Val Leu Pro Asp Glu Ala Ala Arg Ala Arg Leu Leu Gln Glu Gly Gly
65                  70                  75                  80

Gly Gly Val Ala Ala Val Val Val Leu Asp Gln Gly Ser Arg His Trp
                85                  90                  95

Gln Lys Leu Arg Glu Glu Ser Ala Ala Arg Val Val Leu Thr Ser Leu
            100                 105                 110

Leu Ala Cys Leu Pro Ala Gly Pro Arg Val Tyr Phe Leu Lys Gly Gly
        115                 120                 125

Tyr Glu Thr Phe Tyr Ser Glu Tyr Pro Glu Cys Cys Val Asp Val Lys
    130                 135                 140

Pro Ile Ser Gln Glu Lys Ile Glu Ser Glu Arg Ala Leu Ile Ser Gln
145                 150                 155                 160

Cys Gly Lys Pro Val Val Asn Val Ser Tyr Arg Pro Ala Tyr Asp Gln
                165                 170                 175

Gly Gly Pro Val Glu Ile Leu Pro Phe Leu Tyr Leu Gly Ser Ala Tyr
            180                 185                 190

His Ala Ser Lys Cys Glu Phe Leu Ala Asn Leu His Ile Thr Ala Leu
        195                 200                 205

Leu Asn Val Ser Arg Arg Thr Ser Glu Ala Cys Met Thr His Leu His
    210                 215                 220

Tyr Lys Trp Ile Pro Val Glu Asp Ser His Thr Ala Asp Ile Ser Ser
225                 230                 235                 240

His Phe Gln Glu Ala Ile Asp Phe Ile Asp Cys Val Arg Glu Lys Gly
                245                 250                 255

Gly Lys Val Leu Val His Cys Glu Ala Gly Ile Ser Arg Ser Pro Thr
            260                 265                 270

Ile Cys Met Ala Tyr Leu Met Lys Thr Lys Gln Phe Arg Leu Lys Glu
        275                 280                 285

Ala Phe Asp Tyr Ile Lys Gln Arg Arg Ser Met Val Ser Pro Asn Phe
    290                 295                 300

Gly Phe Met Gly Gln Leu Leu Gln Tyr Glu Ser Glu Ile Leu Pro Ser
305                 310                 315                 320

Thr Pro Asn Pro Gln Pro Pro Ser Cys Gln Gly Glu Ala Ala Gly Ser
                325                 330                 335

Ser Leu Ile Gly His Leu Gln Thr Leu Ser Pro Asp Met Gln Gly Ala
            340                 345                 350

Tyr Cys Thr Phe Pro Ala Ser Val Leu Ala Pro Val Pro Thr His Ser
        355                 360                 365

Thr Val Ser Glu Leu Ser Arg Ser Pro Val Ala Thr Ala Thr Ser Cys
    370                 375                 380
```

<210> SEQ ID NO 35
<211> LENGTH: 741
<212> TYPE: DNA

<213> ORGANISM: Homo sapiens

<400> SEQUENCE: 35

```
atgctccaaa actcagcagt gcttctggtg ctggtgatca gtgcttctgc aacccatgag      60
gcggagcaga atgactctgt gagccccagg aaatcccgag tggcggccca aaactcagct     120
gaagtggttc gttgcctcaa cagtgctcta caggtcggct gcggggcttt tgcatgcctg     180
gaaaactcca cctgtgacac agatgggatg tatgacatct gtaaatcctt cttgtacagc     240
gctgctaaat ttgacactca gggaaaagca ttcgtcaaag agagcttaaa atgcatcgcc     300
aacggggtca cctccaaggt cttcctcgcc attcggaggt gctccacttt ccaaaggatg     360
attgctgagg tgcaggaaga gtgctacagc aagctgaatg tgtgcagcat cgccaagcgg     420
aaccctgaag ccatcactga ggtcgtccag ctgcccaatc acttctccaa cagatactat     480
aacagacttg tccgaagcct gctggaatgt gatgaagaca cagtcagcac aatcagagac     540
agcctgatgg agaaaattgg gcctaacatg gccagcctct tccacatcct gcagacagac     600
cactgtgccc aaacacaccc acgagctgac ttcaacagga gacgcaccaa tgagccgcag     660
aagctgaaag tcctcctcag gaacctccga ggtgaggagg actctccctc ccacatcaaa     720
cgcacatccc atgagagtgc a                                               741
```

<210> SEQ ID NO 36
<211> LENGTH: 247
<212> TYPE: PRT
<213> ORGANISM: Homo sapiens

<400> SEQUENCE: 36

```
Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Arg Thr Asn Glu Pro Gln Lys Leu Lys Val
    210                 215                 220
```

```
Leu Leu Arg Asn Leu Arg Gly Glu Glu Asp Ser Pro Ser His Ile Lys
225                 230                 235                 240

Arg Thr Ser His Glu Ser Ala
                245


<210> SEQ ID NO 37
<211> LENGTH: 2580
<212> TYPE: DNA
<213> ORGANISM: Homo sapiens

<400> SEQUENCE: 37

atggggccct ggggctggaa attgcgctgg accgtcgcct tgctcctcgc cgcggcgggg     60

actgcagtgg gcgacagatg tgaaagaaac gagttccagt gccaagacgg gaaatgcatc    120

tcctacaagt gggtctgcga tggcagcgct gagtgccagg atggctctga tgagtcccag    180

gagacgtgct tgtctgtcac ctgcaaatcc ggggacttca gctgtggggg ccgtgtcaac    240

cgctgcattc ctcagttctg gaggtgcgat ggccaagtgg actgcgacaa cggctcagac    300

gagcaaggct gtccccccaa gacgtgctcc caggacgagt ttcgctgcca cgatgggaag    360

tgcatctctc ggcagttcgt ctgtgactca gaccgggact gcttggacgg ctcagacgag    420

gcctcctgcc cggtgctcac ctgtggtccc gccagcttcc agtgcaacag ctccacctgc    480

atcccccagc tgtgggcctg cgacaacgac cccgactgcg aagatggctc ggatgagtgg    540

ccgcagcgct gtaggggtct ttacgtgttc caaggggaca gtagcccctg ctcggccttc    600

gagttccact gcctaagtgg cgagtgcatc cactccagct ggcgctgtga tggtggcccc    660

gactgcaagg acaaatctga cgaggaaaac tgcgctgtgg ccacctgtcg ccctgacgaa    720

ttccagtgct ctgatggaaa ctgcatccat ggcagccggc agtgtgaccg ggaatatgac    780

tgcaaggaca tgagcgatga agttggctgc gttaatgtga cactctgcga gggacccaac    840

aagttcaagt gtcacagcgg cgaatgcatc accctggaca aagtctgcaa catggctaga    900

gactgccggg actggtcaga tgaacccatc aaagagtgcg ggaccaacga atgcttggac    960

aacaacggcg gctgttccca cgtctgcaat gaccttaaga tcggctacga gtgcctgtgc   1020

cccgacggct tccagctggt ggcccagcga agatgcgaag atatcgatga gtgtcaggat   1080

cccgacacct gcagccagct ctgcgtgaac ctggagggtg gctacaagtg ccagtgtgag   1140

gaaggcttcc agctggaccc ccacacgaag gcctgcaagg ctgtgggctc catcgcctac   1200

ctcttcttca ccaaccggca cgaggtcagg aagatgacgc tggaccggag cgagtacacc   1260

agcctcatcc ccaacctgag gaacgtggtc gctctggaca cggaggtggc cagcaataga   1320

atctactggt ctgacctgtc ccagagaatg atctgcagca cccagcttga cagagcccac   1380

ggcgtctctt cctatgacac cgtcatcagc agggacatcc aggcccccga cgggctggct   1440

gtggactgga tccacagcaa catctactgg accgactctg tcctgggcac tgtctctgtt   1500

gcggatacca agggcgtgaa gaggaaaacg ttattcaggg agaacggctc caagccaagg   1560

gccatcgtgg tggatcctgt tcatggcttc atgtactgga ctgactgggg aactcccgcc   1620

aagatcaaga aagggggcct gaatggtgtg gacatctact cgctggtgac tgaaaacatt   1680

cagtggccca atggcatcac cctagatctc ctcagtggcc gcctctactg ggttgactcc   1740

aaacttcact ccatctcaag catcgatgtc aatgggggca accggaagac catcttggag   1800

gatgaaaaga ggctggccca cccccttctcc ttggccgtct ttgaggacaa agtatttttgg   1860

acagatatca tcaacgaagc cattttcagt gccaaccgcc tcacaggttc cgatgtcaac   1920

ttgttggctg aaaacctact gtccccagag gatatggtcc tcttccacaa cctcacccag   1980
```

```
ccaagaggag tgaactggtg tgagaggacc accctgagca atggcggctg ccagtatctg   2040

tgcctccctg ccccgcagat caaccccac tcgcccaagt ttacctgcgc ctgcccggac   2100

ggcatgctgc tggccaggga catgaggagc tgcctcacag aggctgaggc tgcagtggcc   2160

acccaggaga catccaccgt caggctaaag gtcagctcca cagccgtaag gacacagcac   2220

acaaccaccc ggcctgttcc cgacacctcc cggctgcctg gggccacccc tgggctcacc   2280

acggtggaga tagtgacaat gtctcaccaa gctctgggcg acgttgctgg cagaggaaat   2340

gagaagaagc ccagtagcgt gagggctctg tccattgtcc tccccatcgt gctcctcgtc   2400

ttcctttgcc tgggggtctt ccttctatgg aagaactggc ggcttaagaa catcaacagc   2460

atcaactttg acaaccccgt ctatcagaag accacagagg atgaggtcca catttgccac   2520

aaccaggacg gctacagcta cccctcgaga cagatggtca gtctggagga tgacgtggcg   2580


<210> SEQ ID NO 38
<211> LENGTH: 860
<212> TYPE: PRT
<213> ORGANISM: Homo sapiens

<400> SEQUENCE: 38

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
```

```
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700
```

```
Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860
```

<210> SEQ ID NO 39
<211> LENGTH: 1320
<212> TYPE: DNA
<213> ORGANISM: Homo sapiens

<400> SEQUENCE: 39

```
atggaacaac ggggacagaa cgccccggcc gcttcggggg cccggaaaag gcacggccca     60

ggacccaggg aggcgcgggg agccaggcct gggctccggg tccccaagac ccttgtgctc    120

gttgtcgccg cggtcctgct gttggtctca gctgagtctg ctctgatcac ccaacaagac    180

ctagctcccc agcagagagt ggccccacaa caaaagaggt ccagcccctc agagggattg    240

tgtccacctg gacaccatat ctcagaagac ggtagagatt gcatctcctg caaatatgga    300

caggactata gcactcactg gaatgacctc cttttctgct tgcgctgcac caggtgtgat    360

tcaggtgaag tggagctaag tccctgcacc acgaccagaa acacagtgtg tcagtgcgaa    420

gaaggcacct tccgggaaga agattctcct gagatgtgcc ggaagtgccg cacagggtgt    480

cccagaggga tggtcaaggt cggtgattgt acaccctgga gtgacatcga atgtgtccac    540

aaagaatcag gtacaaagca cagtggggaa gccccagctg tggaggagac ggtgacctcc    600

agcccaggga ctcctgcctc tccctgttct ctctcaggca tcatcatagg agtcacagtt    660

gcagccgtag tcttgattgt ggctgtgttt gtttgcaagt ctttactgtg gaagaaagtc    720

cttccttacc tgaaaggcat ctgctcaggt ggtggtgggg accctgagcg tgtggacaga    780

agctcacaac gacctggggc tgaggacaat gtcctcaatg agatcgtgag tatcttgcag    840

cccacccagg tccctgagca ggaaatggaa gtccaggagc cagcagagcc aacaggtgtc    900

aacatgttgt cccccgggga gtcagagcat ctgctggaac cggcagaagc tgaaaggtct    960

cagaggagga ggctgctggt tccagcaaat gaaggtgatc ccactgagac tctgagacag   1020

tgcttcgatg actttgcaga cttggtgccc tttgactcct gggagccgct catgaggaag   1080

ttgggcctca tggacaatga gataaaggtg gctaaagctg aggcagcggg ccacagggac   1140

accttgtaca cgatgctgat aaagtgggtc aacaaaaccg ggcgagatgc ctctgtccac   1200

accctgctgg atgccttgga gacgctggga gagagacttg ccaagcagaa gattgaggac   1260
```

```
cacttgttga gctctggaaa gttcatgtat ctagaaggta atgcagactc tgccatgtcc   1320


<210> SEQ ID NO 40
<211> LENGTH: 440
<212> TYPE: PRT
<213> ORGANISM: Homo sapiens

<400> SEQUENCE: 40

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
```

```
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440


<210> SEQ ID NO 41
<211> LENGTH: 387
<212> TYPE: DNA
<213> ORGANISM: Homo sapiens

<400> SEQUENCE: 41

atggctcggg gctcgctgcg ccggttgctg cggctcctcg tgctggggct ctggctggcg      60

ttgctgcgct ccgtggccgg ggagcaagcg ccaggcaccg ccccctgctc ccgcggcagc     120

tcctggagcg cggacctgga caagtgcatg gactgcgcgt cttgcagggc gcgaccgcac     180

agcgacttct gcctgggctg cgctgcagca cctcctgccc ccttccggct gctttggccc     240

atccttgggg gcgctctgag cctgaccttc gtgctggggc tgctttctgg ctttttggtc     300

tggagacgat gccgcaggag agagaagttc accacccccca tagaggagac cggcggagag    360

ggctgcccag ctgtggcgct gatccag                                         387


<210> SEQ ID NO 42
<211> LENGTH: 129
<212> TYPE: PRT
<213> ORGANISM: Homo sapiens

<400> SEQUENCE: 42

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln


<210> SEQ ID NO 43
<211> LENGTH: 1401
<212> TYPE: DNA
<213> ORGANISM: Homo sapiens

<400> SEQUENCE: 43

atggagtaca tgagcactgg aagtgacaat aaagaagaga ttgatttatt aattaaacat      60
```

```
ttaaatgtgt ctgatgtaat agacattatg gaaaatcttt atgcaagtga agagccagca    120

gtttatgaac ccagtctaat gaccatgtgt caagacagta atcaaaacga tgagcgttct    180

aagtctctgc tgcttagtgg ccaagaggta ccatggttgt catcagtcag atatggaact    240

gtggaggatt tgcttgcttt tgcaaaccat atatccaaca ctgcaaagca tttttatgga    300

caacgaccac aggaatctgg aattttatta aacatggtca tcactcccca aaatggacgt    360

taccaaatag attccgatgt tctcctgatc ccctggaagc tgacttacag gaatattggt    420

tctgatttta ttcctcgggg cgcctttgga aaggtatact tggcacaaga tataaagacg    480

aagaaaagaa tggcgtgtaa actgatccca gtagatcaat ttaagccatc tgatgtggaa    540

atccaggctt gcttccggca cgagaacatc gcagagctgt atggcgcagt cctgtggggt    600

gaaactgtcc atctctttat ggaagcaggc gagggagggt ctgttctgga gaaactggag    660

agctgtggac caatgagaga atttgaaatt atttgggtga caaagcatgt tctcaaggga    720

cttgattttc tacactcaaa gaaagtgatc catcatgata ttaaacctag caacattgtt    780

ttcatgtcca caaaagctgt tttggtggat tttggcctaa gtgttcaaat gaccgaagat    840

gtctattttc ctaaggacct ccgaggaaca gagatttaca tgagcccaga ggtcatcctg    900

tgcaggggcc attcaaccaa agcagacatc tacagcctgg gggccacgct catccacatg    960

cagacgggca ccccaccctg ggtgaagcgc taccctcgct cagcctatcc ctcctacctg   1020

tacataatcc acaagcaagc acctccactg gaagacattg cagatgactg cagtccaggg   1080

atgagagagc tgatagaagc ttccctggag agaaacccca atcaccgccc aagagccgca   1140

gacctactaa aacatgaggc cctgaacccg cccagagagg atcagccacg ctgtcagagt   1200

ctggactctg ccctcttgga gcgcaagagg ctgctgagta ggaaggagct ggaacttcct   1260

gagaacattg ctgattcttc gtgcacagga agcaccgagg aatctgagat gctcaagagg   1320

caacgctctc tctacatcga cctcggcgct ctggctggct acttcaatct tgttcgggga   1380

ccaccaacgc ttgaatatgg c                                             1401
```

<210> SEQ ID NO 44
<211> LENGTH: 467
<212> TYPE: PRT
<213> ORGANISM: Homo sapiens

<400> SEQUENCE: 44

```
Met Glu Tyr Met Ser Thr Gly Ser Asp Asn Lys Glu Glu Ile Asp Leu
1               5                   10                  15

Leu Ile Lys His Leu Asn Val Ser Asp Val Ile Asp Ile Met Glu Asn
            20                  25                  30

Leu Tyr Ala Ser Glu Glu Pro Ala Val Tyr Glu Pro Ser Leu Met Thr
        35                  40                  45

Met Cys Gln Asp Ser Asn Gln Asn Asp Glu Arg Ser Lys Ser Leu Leu
    50                  55                  60

Leu Ser Gly Gln Glu Val Pro Trp Leu Ser Ser Val Arg Tyr Gly Thr
65                  70                  75                  80

Val Glu Asp Leu Leu Ala Phe Ala Asn His Ile Ser Asn Thr Ala Lys
                85                  90                  95

His Phe Tyr Gly Gln Arg Pro Gln Glu Ser Gly Ile Leu Leu Asn Met
            100                 105                 110

Val Ile Thr Pro Gln Asn Gly Arg Tyr Gln Ile Asp Ser Asp Val Leu
        115                 120                 125

Leu Ile Pro Trp Lys Leu Thr Tyr Arg Asn Ile Gly Ser Asp Phe Ile
    130                 135                 140
```

```
Pro Arg Gly Ala Phe Gly Lys Val Tyr Leu Ala Gln Asp Ile Lys Thr
145                 150                 155                 160

Lys Lys Arg Met Ala Cys Lys Leu Ile Pro Val Asp Gln Phe Lys Pro
                165                 170                 175

Ser Asp Val Glu Ile Gln Ala Cys Phe Arg His Glu Asn Ile Ala Glu
            180                 185                 190

Leu Tyr Gly Ala Val Leu Trp Gly Glu Thr Val His Leu Phe Met Glu
        195                 200                 205

Ala Gly Glu Gly Gly Ser Val Leu Glu Lys Leu Glu Ser Cys Gly Pro
    210                 215                 220

Met Arg Glu Phe Glu Ile Ile Trp Val Thr Lys His Val Leu Lys Gly
225                 230                 235                 240

Leu Asp Phe Leu His Ser Lys Lys Val Ile His His Asp Ile Lys Pro
                245                 250                 255

Ser Asn Ile Val Phe Met Ser Thr Lys Ala Val Leu Val Asp Phe Gly
            260                 265                 270

Leu Ser Val Gln Met Thr Glu Asp Val Tyr Phe Pro Lys Asp Leu Arg
        275                 280                 285

Gly Thr Glu Ile Tyr Met Ser Pro Glu Val Ile Leu Cys Arg Gly His
    290                 295                 300

Ser Thr Lys Ala Asp Ile Tyr Ser Leu Gly Ala Thr Leu Ile His Met
305                 310                 315                 320

Gln Thr Gly Thr Pro Pro Trp Val Lys Arg Tyr Pro Arg Ser Ala Tyr
                325                 330                 335

Pro Ser Tyr Leu Tyr Ile Ile His Lys Gln Ala Pro Pro Leu Glu Asp
            340                 345                 350

Ile Ala Asp Asp Cys Ser Pro Gly Met Arg Glu Leu Ile Glu Ala Ser
        355                 360                 365

Leu Glu Arg Asn Pro Asn His Arg Pro Arg Ala Ala Asp Leu Leu Lys
    370                 375                 380

His Glu Ala Leu Asn Pro Pro Arg Glu Asp Gln Pro Arg Cys Gln Ser
385                 390                 395                 400

Leu Asp Ser Ala Leu Leu Glu Arg Lys Arg Leu Leu Ser Arg Lys Glu
                405                 410                 415

Leu Glu Leu Pro Glu Asn Ile Ala Asp Ser Ser Cys Thr Gly Ser Thr
            420                 425                 430

Glu Glu Ser Glu Met Leu Lys Arg Gln Arg Ser Leu Tyr Ile Asp Leu
        435                 440                 445

Gly Ala Leu Ala Gly Tyr Phe Asn Leu Val Arg Gly Pro Pro Thr Leu
    450                 455                 460

Glu Tyr Gly
465
```

<210> SEQ ID NO 45
<211> LENGTH: 1629
<212> TYPE: DNA
<213> ORGANISM: Homo sapiens

<400> SEQUENCE: 45

```
atggccgcgg ccaaggccga gatgcagctg atgtccccgc tgcagatctc tgacccgttc      60

ggatcctttc ctcactcgcc caccatggac aactacccta agctggagga gatgatgctg     120

ctgagcaacg gggctcccca gttcctcggc gccgccgggg ccccagaggg cagcggcagc     180

aacagcagca gcagcagcag cgggggcggt ggaggcggcg ggggcggcag caacagcagc     240
```

```
agcagcagca gcaccttcaa ccctcaggcg gacacgggcg agcagcccta cgagcacctg    300

accgcagagt cttttcctga catctctctg aacaacgaga aggtgctggt ggagaccagt    360

taccccagcc aaaccactcg actgcccccc atcacctata ctggccgctt ttccctggag    420

cctgcaccca acagtggcaa caccttgtgg cccgagcccc tcttcagctt ggtcagtggc    480

ctagtgagca tgaccaaccc accggcctcc tcgtcctcag caccatctcc agcggcctcc    540

tccgcctccg cctcccagag cccacccctg agctgcgcag tgccatccaa cgacagcagt    600

cccatttact cagcggcacc caccttcccc acgccgaaca ctgacatttt ccctgagcca    660

caaagccagg ccttcccggg ctcggcaggg acagcgctcc agtacccgcc tcctgcctac    720

cctgccgcca agggtggctt ccaggttccc atgatccccg actacctgtt tccacagcag    780

cagggggatc tgggcctggg caccccagac cagaagccct tccagggcct ggagagccgc    840

acccagcagc cttcgctaac ccctctgtct actattaagg cctttgccac tcagtcgggc    900

tcccaggacc tgaaggccct caataccagc taccagtccc agctcatcaa acccagccgc    960

atgcgcaagt accccaaccg gcccagcaag acgccccccc acgaacgccc ttacgcttgc   1020

ccagtggagt cctgtgatcg ccgcttctcc cgctccgacg agctcacccg ccacatccgc   1080

atccacacag gccagaagcc cttccagtgc cgcatctgca tgcgcaactt cagccgcagc   1140

gaccacctca ccacccacat ccgcacccac acaggcgaaa agcccttcgc ctgcgacatc   1200

tgtggaagaa agtttgccag gagcgatgaa cgcaagaggc ataccaagat ccacttgcgg   1260

cagaaggaca agaaagcaga caaaagtgtt gtggcctctt cggccacctc ctctctctct   1320

tcctacccgt ccccggttgc tacctcttac ccgtccccgg ttactacctc ttatccatcc   1380

ccggccacca cctcataccc atcccctgtg cccacctcct tctcctctcc cggctcctcg   1440

acctacccat cccctgtgca cagtggcttc ccctccccgt cggtggccac cacgtactcc   1500

tctgttcccc ctgctttccc ggcccaggtc agcagcttcc cttcctcagc tgtcaccaac   1560

tccttcagcg cctccacagg gctttcggac atgacagcaa ccttttctcc caggacaatt   1620

gaaatttgc                                                           1629
```

<210> SEQ ID NO 46
<211> LENGTH: 543
<212> TYPE: PRT
<213> ORGANISM: Homo sapiens

<400> SEQUENCE: 46

```
Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125
```

```
Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
        355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
                405                 410                 415

Ile His Leu Arg Gln Lys Asp Lys Lys Ala Asp Lys Ser Val Val Ala
            420                 425                 430

Ser Ser Ala Thr Ser Ser Leu Ser Ser Tyr Pro Ser Pro Val Ala Thr
        435                 440                 445

Ser Tyr Pro Ser Pro Val Thr Thr Ser Tyr Pro Ser Pro Ala Thr Thr
    450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
                485                 490                 495

Thr Thr Tyr Ser Ser Val Pro Pro Ala Phe Pro Ala Gln Val Ser Ser
            500                 505                 510

Phe Pro Ser Ser Ala Val Thr Asn Ser Phe Ser Ala Ser Thr Gly Leu
        515                 520                 525

Ser Asp Met Thr Ala Thr Phe Ser Pro Arg Thr Ile Glu Ile Cys
    530                 535                 540
```

<210> SEQ ID NO 47

<211> LENGTH: 1161
<212> TYPE: DNA
<213> ORGANISM: Homo sapiens

<400> SEQUENCE: 47

```
atgaccggca aactcgccga gaagctgccg gtgaccatga gcagtttgct aaaccaactg     60
cctgacaatc tgtaccccga ggagatcccc agcgcgctca acctcttctc cggcagcagc    120
gactcggtag tccattacaa tcagatggct acagagaatg taatggacat cggtctgacc    180
aacgagaagc ccaacccgga actctcttac tccggctcct tccagccagc cccccggcaac   240
aagaccgtga cctacttggg aaagttcgcc ttcgactccc cttccaactg gtgccaggac    300
aacatcatta gcctcatgag cgccggcatc ttgggggtgc ccccggcttc aggggcgctc    360
agcacgcaga cgtccacggc cagcatggtg cagccaccgc agggtgacgt ggaggccatg    420
tatcccgcgc tacccccccta ctccaactgc ggcgacctct actcagagcc cgtgtctttc   480
cacgaccccc agggcaatcc cgggctcgcc tattcccccc aggattacca atcggccaag    540
ccggcgttgg acagcaatct cttccccatg attcctgact acaacctcta ccaccacccc    600
aacgacatgg gctccattcc ggagcacaag cccttccagg gcatggaccc catccgggtc    660
aacccgcccc ctattacccc tctggagacc atcaaggcat tcaaagacaa gcagatccac    720
ccgggctttg gcagcctgcc ccagccgccg ctcaccctca agcccatccg gccccgcaag    780
taccccaacc ggcctagcaa gacaccgctc cacgaacggc cccacgcgtg cccggccgag    840
ggctgcgacc gccgtttcag ccgttcggac gagctgaccc ggcacctgcg catccacacg    900
ggccacaagc ccttccagtg ccggatctgc atgcggagct tcagccgcag cgaccacctc    960
accactcaca tccgcactca tacgggcgag aagccctttg cctgcgagtt ctgcgggcgc   1020
aagtttgcgc gcagcgacga gcgcaagcgc cacgccaaga tccacctcaa gcaaaaggag   1080
aagaaggcgg agaagggcgg tgcaccctct gcatcctcgg cgccccccgt gtcgctggcc   1140
cccgtggtca ccacctgcgc c                                             1161
```

<210> SEQ ID NO 48
<211> LENGTH: 387
<212> TYPE: PRT
<213> ORGANISM: Homo sapiens

<400> SEQUENCE: 48

```
Met Thr Gly Lys Leu Ala Glu Lys Leu Pro Val Thr Met Ser Ser Leu
1               5                   10                  15

Leu Asn Gln Leu Pro Asp Asn Leu Tyr Pro Glu Glu Ile Pro Ser Ala
            20                  25                  30

Leu Asn Leu Phe Ser Gly Ser Ser Asp Ser Val Val His Tyr Asn Gln
        35                  40                  45

Met Ala Thr Glu Asn Val Met Asp Ile Gly Leu Thr Asn Glu Lys Pro
    50                  55                  60

Asn Pro Glu Leu Ser Tyr Ser Gly Ser Phe Gln Pro Ala Pro Gly Asn
65                  70                  75                  80

Lys Thr Val Thr Tyr Leu Gly Lys Phe Ala Phe Asp Ser Pro Ser Asn
                85                  90                  95

Trp Cys Gln Asp Asn Ile Ile Ser Leu Met Ser Ala Gly Ile Leu Gly
            100                 105                 110

Val Pro Pro Ala Ser Gly Ala Leu Ser Thr Gln Thr Ser Thr Ala Ser
        115                 120                 125

Met Val Gln Pro Pro Gln Gly Asp Val Glu Ala Met Tyr Pro Ala Leu
    130                 135                 140
```

```
Pro Pro Tyr Ser Asn Cys Gly Asp Leu Tyr Ser Glu Pro Val Ser Phe
145                 150                 155                 160

His Asp Pro Gln Gly Asn Pro Gly Leu Ala Tyr Ser Pro Gln Asp Tyr
                165                 170                 175

Gln Ser Ala Lys Pro Ala Leu Asp Ser Asn Leu Phe Pro Met Ile Pro
            180                 185                 190

Asp Tyr Asn Leu Tyr His His Pro Asn Asp Met Gly Ser Ile Pro Glu
        195                 200                 205

His Lys Pro Phe Gln Gly Met Asp Pro Ile Arg Val Asn Pro Pro Pro
    210                 215                 220

Ile Thr Pro Leu Glu Thr Ile Lys Ala Phe Lys Asp Lys Gln Ile His
225                 230                 235                 240

Pro Gly Phe Gly Ser Leu Pro Gln Pro Pro Leu Thr Leu Lys Pro Ile
                245                 250                 255

Arg Pro Arg Lys Tyr Pro Asn Arg Pro Ser Lys Thr Pro Leu His Glu
            260                 265                 270

Arg Pro His Ala Cys Pro Ala Glu Gly Cys Asp Arg Arg Phe Ser Arg
        275                 280                 285

Ser Asp Glu Leu Thr Arg His Leu Arg Ile His Thr Gly His Lys Pro
    290                 295                 300

Phe Gln Cys Arg Ile Cys Met Arg Ser Phe Ser Arg Ser Asp His Leu
305                 310                 315                 320

Thr Thr His Ile Arg Thr His Thr Gly Glu Lys Pro Phe Ala Cys Glu
                325                 330                 335

Phe Cys Gly Arg Lys Phe Ala Arg Ser Asp Glu Arg Lys Arg His Ala
            340                 345                 350

Lys Ile His Leu Lys Gln Lys Glu Lys Lys Ala Glu Lys Gly Gly Ala
        355                 360                 365

Pro Ser Ala Ser Ser Ala Pro Pro Val Ser Leu Ala Pro Val Val Thr
    370                 375                 380

Thr Cys Ala
385
```

<210> SEQ ID NO 49
<211> LENGTH: 2850
<212> TYPE: DNA
<213> ORGANISM: Homo sapiens

<400> SEQUENCE: 49

```
atggggaacg cggagcgggc tccggggtct cggagctttg ggcccgtacc cacgctgctg      60

ctgctcgccg cggcgctact ggccgtgtcg gacgcactcg ggcgcccctc cgaggaggac     120

gaggagctag tggtgccgga gctggagcgc gccccgggac acgggaccac gcgcctccgc     180

ctgcacgcct ttgaccagca gctggatctg gagctgcggc ccgacagcag ctttttggcg     240

cccggcttca cgctccagaa cgtggggcgc aaatccgggt ccgagacgcc gcttccggaa     300

accgacctgg cgcactgctt ctactccggc accgtgaatg gcgatcccag ctcggctgcc     360

gccctcagcc tctgcgaggg cgtgcgcggc gccttctacc tgctggggga ggcgtatttc     420

atccagccgc tgcccgccgc cagcgagcgc ctcgccaccg ccgccccagg ggagaagccg     480

ccggcaccac tacagttcca cctcctgcgg cggaatcggc agggcgacgt cggcggcacg     540

tgcggggtcg tggacgacga gccccggccg actgggaaag cggagaccga agacgaggac     600

gaagggactg agggcgagga cgaaggggct cagtggtcgc cgcaggaccc ggcactgcaa     660

ggcgtaggac agcccacagg aactggaagc ataagaaaga agcgatttgt gtccagtcac     720
```

```
cgctatgtgg aaaccatgct tgtggcagac cagtcgatgg cagaattcca cggcagtggt    780

ctaaagcatt accttctcac gttgttttcg gtggcagcca gattgtacaa acaccccagc    840

attcgtaatt cagttagcct ggtggtggtg aagatcttgg tcatccacga tgaacagaag    900

gggccggaag tgacctccaa tgctgccctc actctgcgga acttttgcaa ctggcagaag    960

cagcacaacc cacccagtga ccgggatgca gagcactatg acacagcaat tcttttcacc   1020

agacaggact tgtgtgggtc ccagacatgt gatactcttg ggatggctga tgttggaact   1080

gtgtgtgatc cgagcagaag ctgctccgtc atagaagatg atggtttaca agctgccttc   1140

accacagccc atgaattagg ccacgtgttt aacatgccac atgatgatgc aaagcagtgt   1200

gccagcctta atggtgtgaa ccaggattcc cacatgatgg cgtcaatgct ttccaacctg   1260

gaccacagcc agccttggtc tccttgcagt gcctacatga ttacatcatt tctggataat   1320

ggtcatgggg aatgtttgat ggacaagcct cagaatccca tacagctccc aggcgatctc   1380

cctggcacct cgtacgatgc caaccggcag tgccagttta catttgggga ggactccaaa   1440

cactgccccg atgcagccag cacatgtagc accttgtggt gtaccggcac ctctggtggg   1500

gtgctggtgt gtcaaaccaa acacttcccg tgggcggatg gcaccagctg tggagaaggg   1560

aaatggtgta tcaacggcaa gtgtgtgaac aaaaccgaca gaaagcattt tgatacgcct   1620

tttcatggaa gctggggaat gtgggggcct tggggagact gttcgagaac gtgcggtgga   1680

ggagtccagt acacgatgag ggaatgtgac aacccagtcc caaagaatgg agggaagtac   1740

tgtgaaggca aacgagtgcg ctacagatcc tgtaaccttg aggactgtcc agacaataat   1800

ggaaaaacct ttagagagga acaatgtgaa gcacacaacg agttttcaaa agcttccttt   1860

gggagtgggc ctgcggtgga atggattccc aagtacgctg gcgtctcacc aaaggacagg   1920

tgcaagctca tctgccaagc caaaggcatt ggctacttct tcgttttgca gcccaaggtt   1980

gtagatggta ctccatgtag cccagattcc acctctgtct gtgtgcaagg acagtgtgta   2040

aaagctggtt gtgatcgcat catagactcc aaaaagaagt ttgataaatg tggtgtttgc   2100

gggggaaatg gatctacttg taaaaaaata tcaggatcag ttactagtgc aaaacctgga   2160

tatcatgata tcatcacaat tccaactgga gccaccaaca tcgaagtgaa acagcggaac   2220

cagaggggat ccaggaacaa tggcagcttt cttgccatca aagctgctga tggcacatat   2280

attcttaatg gtgactacac tttgtccacc ttagagcaag acattatgta caaaggtgtt   2340

gtcttgaggt acagcggctc ctctgcggca ttggaaagaa ttcgcagctt tagccctctc   2400

aaagagccct tgaccatcca ggttcttact gtgggcaatg cccttcgacc taaaattaaa   2460

tacacctact tcgtaaagaa gaagaaggaa tctttcaatg ctatccccac tttttcagca   2520

tgggtcattg aagagtgggg cgaatgttct aagtcatgtg aattgggttg gcagagaaga   2580

ctggtagaat gccgagacat taatggacag cctgcttccg agtgtgcaaa ggaagtgaag   2640

ccagccagca ccagaccttg tgcagaccat ccctgccccc agtggcagct gggggagtgg   2700

tcatcatgtt ctaagacctg tgggaagggt tacaaaaaaa gaagcttgaa gtgtctgtcc   2760

catgatggag ggtgttatc tcatgagagc tgtgatcctt taaagaaacc taaacatttc    2820

atagactttt gcacaatggc agaatgcagt                                    2850
```

<210> SEQ ID NO 50
<211> LENGTH: 950
<212> TYPE: PRT
<213> ORGANISM: Homo sapiens

<400> SEQUENCE: 50

```
Met Gly Asn Ala Glu Arg Ala Pro Gly Ser Arg Ser Phe Gly Pro Val
1               5                   10                  15

Pro Thr Leu Leu Leu Leu Ala Ala Ala Leu Leu Ala Val Ser Asp Ala
            20                  25                  30

Leu Gly Arg Pro Ser Glu Glu Asp Glu Glu Leu Val Val Pro Glu Leu
        35                  40                  45

Glu Arg Ala Pro Gly His Gly Thr Thr Arg Leu Arg Leu His Ala Phe
    50                  55                  60

Asp Gln Gln Leu Asp Leu Glu Leu Arg Pro Asp Ser Ser Phe Leu Ala
65                  70                  75                  80

Pro Gly Phe Thr Leu Gln Asn Val Gly Arg Lys Ser Gly Ser Glu Thr
                85                  90                  95

Pro Leu Pro Glu Thr Asp Leu Ala His Cys Phe Tyr Ser Gly Thr Val
            100                 105                 110

Asn Gly Asp Pro Ser Ser Ala Ala Ala Leu Ser Leu Cys Glu Gly Val
        115                 120                 125

Arg Gly Ala Phe Tyr Leu Leu Gly Glu Ala Tyr Phe Ile Gln Pro Leu
    130                 135                 140

Pro Ala Ala Ser Glu Arg Leu Ala Thr Ala Ala Pro Gly Glu Lys Pro
145                 150                 155                 160

Pro Ala Pro Leu Gln Phe His Leu Leu Arg Arg Asn Arg Gln Gly Asp
                165                 170                 175

Val Gly Gly Thr Cys Gly Val Val Asp Asp Glu Pro Arg Pro Thr Gly
            180                 185                 190

Lys Ala Glu Thr Glu Asp Glu Asp Glu Gly Thr Glu Gly Glu Asp Glu
        195                 200                 205

Gly Ala Gln Trp Ser Pro Gln Asp Pro Ala Leu Gln Gly Val Gly Gln
    210                 215                 220

Pro Thr Gly Thr Gly Ser Ile Arg Lys Lys Arg Phe Val Ser Ser His
225                 230                 235                 240

Arg Tyr Val Glu Thr Met Leu Val Ala Asp Gln Ser Met Ala Glu Phe
                245                 250                 255

His Gly Ser Gly Leu Lys His Tyr Leu Leu Thr Leu Phe Ser Val Ala
            260                 265                 270

Ala Arg Leu Tyr Lys His Pro Ser Ile Arg Asn Ser Val Ser Leu Val
        275                 280                 285

Val Val Lys Ile Leu Val Ile His Asp Glu Gln Lys Gly Pro Glu Val
    290                 295                 300

Thr Ser Asn Ala Ala Leu Thr Leu Arg Asn Phe Cys Asn Trp Gln Lys
305                 310                 315                 320

Gln His Asn Pro Pro Ser Asp Arg Asp Ala Glu His Tyr Asp Thr Ala
                325                 330                 335

Ile Leu Phe Thr Arg Gln Asp Leu Cys Gly Ser Gln Thr Cys Asp Thr
            340                 345                 350

Leu Gly Met Ala Asp Val Gly Thr Val Cys Asp Pro Ser Arg Ser Cys
        355                 360                 365

Ser Val Ile Glu Asp Asp Gly Leu Gln Ala Ala Phe Thr Thr Ala His
    370                 375                 380

Glu Leu Gly His Val Phe Asn Met Pro His Asp Asp Ala Lys Gln Cys
385                 390                 395                 400

Ala Ser Leu Asn Gly Val Asn Gln Asp Ser His Met Met Ala Ser Met
                405                 410                 415

Leu Ser Asn Leu Asp His Ser Gln Pro Trp Ser Pro Cys Ser Ala Tyr
```

```
            420                 425                 430

Met Ile Thr Ser Phe Leu Asp Asn Gly His Gly Glu Cys Leu Met Asp
        435                 440                 445

Lys Pro Gln Asn Pro Ile Gln Leu Pro Gly Asp Leu Pro Gly Thr Ser
    450                 455                 460

Tyr Asp Ala Asn Arg Gln Cys Gln Phe Thr Phe Gly Glu Asp Ser Lys
465                 470                 475                 480

His Cys Pro Asp Ala Ala Ser Thr Cys Ser Thr Leu Trp Cys Thr Gly
                485                 490                 495

Thr Ser Gly Gly Val Leu Val Cys Gln Thr Lys His Phe Pro Trp Ala
            500                 505                 510

Asp Gly Thr Ser Cys Gly Glu Gly Lys Trp Cys Ile Asn Gly Lys Cys
        515                 520                 525

Val Asn Lys Thr Asp Arg Lys His Phe Asp Thr Pro Phe His Gly Ser
    530                 535                 540

Trp Gly Met Trp Gly Pro Trp Gly Asp Cys Ser Arg Thr Cys Gly Gly
545                 550                 555                 560

Gly Val Gln Tyr Thr Met Arg Glu Cys Asp Asn Pro Val Pro Lys Asn
                565                 570                 575

Gly Gly Lys Tyr Cys Glu Gly Lys Arg Val Arg Tyr Arg Ser Cys Asn
            580                 585                 590

Leu Glu Asp Cys Pro Asp Asn Asn Gly Lys Thr Phe Arg Glu Glu Gln
        595                 600                 605

Cys Glu Ala His Asn Glu Phe Ser Lys Ala Ser Phe Gly Ser Gly Pro
    610                 615                 620

Ala Val Glu Trp Ile Pro Lys Tyr Ala Gly Val Ser Pro Lys Asp Arg
625                 630                 635                 640

Cys Lys Leu Ile Cys Gln Ala Lys Gly Ile Gly Tyr Phe Phe Val Leu
                645                 650                 655

Gln Pro Lys Val Val Asp Gly Thr Pro Cys Ser Pro Asp Ser Thr Ser
            660                 665                 670

Val Cys Val Gln Gly Gln Cys Val Lys Ala Gly Cys Asp Arg Ile Ile
        675                 680                 685

Asp Ser Lys Lys Lys Phe Asp Lys Cys Gly Val Cys Gly Gly Asn Gly
    690                 695                 700

Ser Thr Cys Lys Lys Ile Ser Gly Ser Val Thr Ser Ala Lys Pro Gly
705                 710                 715                 720

Tyr His Asp Ile Ile Thr Ile Pro Thr Gly Ala Thr Asn Ile Glu Val
                725                 730                 735

Lys Gln Arg Asn Gln Arg Gly Ser Arg Asn Asn Gly Ser Phe Leu Ala
            740                 745                 750

Ile Lys Ala Ala Asp Gly Thr Tyr Ile Leu Asn Gly Asp Tyr Thr Leu
        755                 760                 765

Ser Thr Leu Glu Gln Asp Ile Met Tyr Lys Gly Val Val Leu Arg Tyr
    770                 775                 780

Ser Gly Ser Ser Ala Ala Leu Glu Arg Ile Arg Ser Phe Ser Pro Leu
785                 790                 795                 800

Lys Glu Pro Leu Thr Ile Gln Val Leu Thr Val Gly Asn Ala Leu Arg
                805                 810                 815

Pro Lys Ile Lys Tyr Thr Tyr Phe Val Lys Lys Lys Lys Glu Ser Phe
            820                 825                 830

Asn Ala Ile Pro Thr Phe Ser Ala Trp Val Ile Glu Glu Trp Gly Glu
        835                 840                 845
```

```
Cys Ser Lys Ser Cys Glu Leu Gly Trp Gln Arg Arg Leu Val Glu Cys
    850                 855                 860

Arg Asp Ile Asn Gly Gln Pro Ala Ser Glu Cys Ala Lys Glu Val Lys
865                 870                 875                 880

Pro Ala Ser Thr Arg Pro Cys Ala Asp His Pro Cys Pro Gln Trp Gln
                885                 890                 895

Leu Gly Glu Trp Ser Ser Cys Ser Lys Thr Cys Gly Lys Gly Tyr Lys
            900                 905                 910

Lys Arg Ser Leu Lys Cys Leu Ser His Asp Gly Gly Val Leu Ser His
        915                 920                 925

Glu Ser Cys Asp Pro Leu Lys Lys Pro Lys His Phe Ile Asp Phe Cys
    930                 935                 940

Thr Met Ala Glu Cys Ser
945                 950
```

<210> SEQ ID NO 51
<211> LENGTH: 705
<212> TYPE: DNA
<213> ORGANISM: Homo sapiens

<400> SEQUENCE: 51

```
atggaccccg ctcgccccct ggggctgtcg attctgctgc ttttcctgac ggaggctgca     60

ctgggcgatg ctgctcagga gccaacagga aataacgcgg agatctgtct cctgccccta    120

gactacggac cctgccgggc cctacttctc cgttactact acgacaggta cacgcagagc    180

tgccgccagt tcctgtacgg gggctgcgag ggcaacgcca acaatttcta cacctgggag    240

gcttgcgacg atgcttgctg gaggatagaa aaagttccca aagtttgccg gctgcaagtg    300

agtgtggacg accagtgtga ggggtccaca gaaaagtatt tctttaatct aagttccatg    360

acatgtgaaa aattcttttc cggtgggtgt caccggaacc ggattgagaa caggtttcca    420

gatgaagcta cttgtatggg cttctgcgca ccaaagaaaa ttccatcatt ttgctacagt    480

ccaaaagatg agggactgtg ctctgccaat gtgactcgct attattttaa tccaagatac    540

agaacctgtg atgctttcac ctatactggc tgtggaggga atgacaataa ctttgttagc    600

agggaggatt gcaaacgtgc atgtgcaaaa gctttgaaaa agaaaaagaa gatgccaaag    660

cttcgctttg ccagtagaat ccggaaaatt cggaagaagc aattt                    705
```

<210> SEQ ID NO 52
<211> LENGTH: 235
<212> TYPE: PRT
<213> ORGANISM: Homo sapiens

<400> SEQUENCE: 52

```
Met Asp Pro Ala Arg Pro Leu Gly Leu Ser Ile Leu Leu Leu Phe Leu
1               5                   10                  15

Thr Glu Ala Ala Leu Gly Asp Ala Ala Gln Glu Pro Thr Gly Asn Asn
            20                  25                  30

Ala Glu Ile Cys Leu Leu Pro Leu Asp Tyr Gly Pro Cys Arg Ala Leu
        35                  40                  45

Leu Leu Arg Tyr Tyr Tyr Asp Arg Tyr Thr Gln Ser Cys Arg Gln Phe
    50                  55                  60

Leu Tyr Gly Gly Cys Glu Gly Asn Ala Asn Asn Phe Tyr Thr Trp Glu
65                  70                  75                  80

Ala Cys Asp Asp Ala Cys Trp Arg Ile Glu Lys Val Pro Lys Val Cys
                85                  90                  95

Arg Leu Gln Val Ser Val Asp Asp Gln Cys Glu Gly Ser Thr Glu Lys
```

```
            100                 105                 110

Tyr Phe Phe Asn Leu Ser Ser Met Thr Cys Glu Lys Phe Phe Ser Gly
        115                 120                 125

Gly Cys His Arg Asn Arg Ile Glu Asn Arg Phe Pro Asp Glu Ala Thr
    130                 135                 140

Cys Met Gly Phe Cys Ala Pro Lys Lys Ile Pro Ser Phe Cys Tyr Ser
145                 150                 155                 160

Pro Lys Asp Glu Gly Leu Cys Ser Ala Asn Val Thr Arg Tyr Tyr Phe
                165                 170                 175

Asn Pro Arg Tyr Arg Thr Cys Asp Ala Phe Thr Tyr Thr Gly Cys Gly
            180                 185                 190

Gly Asn Asp Asn Asn Phe Val Ser Arg Glu Asp Cys Lys Arg Ala Cys
        195                 200                 205

Ala Lys Ala Leu Lys Lys Lys Lys Lys Met Pro Lys Leu Arg Phe Ala
    210                 215                 220

Ser Arg Ile Arg Lys Ile Arg Lys Lys Gln Phe
225                 230                 235


<210> SEQ ID NO 53
<211> LENGTH: 756
<212> TYPE: DNA
<213> ORGANISM: Homo sapiens

<400> SEQUENCE: 53

atgggggtac tgctcacaca gaggacgctg ctcagtctgg tccttgcact cctgtttcca      60

agcatggcga gcatggcggc tataggcagc tgctcgaaag agtaccgcgt gctccttggc     120

cagctccaga agcagacaga tctcatgcag gacaccagca gactcctgga cccctatata     180

cgtatccaag gcctggatgt tcctaaactg agagagcact gcagggagcg ccccggggcc     240

ttccccagtg aggagaccct gagggggctg ggcaggcggg gcttcctgca gaccctcaat     300

gccacactgg gctgcgtcct gcacagactg gccgacttag agcagcgcct ccccaaggcc     360

caggatttgg agaggtctgg gctgaacatc gaggacttgg agaagctgca gatggcgagg     420

ccgaacatcc tcgggctcag gaacaacatc tactgcatgg cccagctgct ggacaactca     480

gacacggctg agcccacgaa ggctggccgg ggggcctctc agccgcccac ccccacccct     540

gcctcggatg cttttcagcg caagctggag ggctgcaggt tcctgcatgg ctaccatcgc     600

ttcatgcact cagtggggcg ggtcttcagc aagtgggggg agagcccgaa ccggagccgg     660

agacacagcc cccaccaggc cctgaggaag gggtgcgca ggaccagacc ctccaggaaa      720

ggcaagagac tcatgaccag ggacagctg ccccgg                                756


<210> SEQ ID NO 54
<211> LENGTH: 252
<212> TYPE: PRT
<213> ORGANISM: Homo sapiens

<400> SEQUENCE: 54

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60
```

```
Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250
```

<210> SEQ ID NO 55
<211> LENGTH: 6603
<212> TYPE: DNA
<213> ORGANISM: Homo sapiens

<400> SEQUENCE: 55

```
atgggggcca tgactcagct gttggcaggt gtctttcttg ctttccttgc cctcgctacc     60

gaaggtgggg tcctcaagaa agtcatccgg cacaagcgac agagtggggt gaacgccacc    120

ctgccagaag agaaccagcc agtggtgttt aaccacgttt acaacatcaa gctgccagtg    180

ggatcccagt gttcggtgga tctggagtca gccagtgggg agaaagacct ggcaccgcct    240

tcagagccca gcgaaagctt tcaggagcac acagtagatg gggaaaacca gattgtcttc    300

acacatcgca tcaacatccc ccgccgggcc tgtggctgtg ccgcagcccc tgatgttaag    360

gagctgctga gcagactgga ggagctggag aacctggtgt cttccctgag ggagcaatgt    420

actgcaggag caggctgctg tctccagcct gccacaggcc gcttggacac caggcccttc    480

tgtagcggtc ggggcaactt cagcactgaa ggatgtggct gtgtctgcga acctggctgg    540

aaaggcccca actgctctga gcccgaatgt ccaggcaact gtcaccttcg aggccggtgc    600

attgatgggc agtgcatctg tgacgacggc ttcacgggcg aggactgcag ccagctggct    660

tgccccagcg actgcaatga ccagggcaag tgcgtgaatg gagtctgcat ctgtttcgaa    720

ggctacgccg gggctgactg cagccgtgaa atctgcccag tgccctgcag tgaggagcac    780

ggcacatgtg tagatggctt gtgtgtgtgc cacgatggct ttgcaggcga tgactgcaac    840

aagcctctgt gtctcaacaa ttgctacaac cgtggacgat gcgtggagaa tgagtgcgtg    900

tgtgatgagg gtttcacggg cgaagactgc agtgagctca tctgccccaa tgactgcttc    960

gaccggggcc gctgcatcaa tggcacctgc tactgcgaag aaggcttcac aggtgaagac   1020

tgcgggaaac ccacctgccc acatgcctgc cacacccagg gccggtgtga ggaggggcag   1080
```

-continued

```
tgtgtatgtg atgagggctt tgccggtttg gactgcagcg agaagaggtg tcctgctgac   1140

tgtcacaatc gtggccgctg tgtagacggg cggtgtgagt gtgatgatgg tttcactgga   1200

gctgactgtg gggagctcaa gtgtcccaat ggctgcagtg gccatggccg ctgtgtcaat   1260

gggcagtgtg tgtgtgatga gggctatact ggggaggact gcagccagct acggtgcccc   1320

aatgactgtc acagtcgggg ccgctgtgtc gagggcaaat gtgtatgtga gcaaggcttc   1380

aagggctatg actgcagtga catgagctgc cctaatgact gtcaccagca cggccgctgt   1440

gtgaatggca tgtgtgtttg tgatgacggc tacacagggg aagactgccg ggatcgccaa   1500

tgccccaggg actgcagcaa caggggcctc tgtgtggacg gacagtgcgt ctgtgaggac   1560

ggcttcaccg gccctgactg tgcagaactc tcctgtccaa atgactgcca tggccagggt   1620

cgctgtgtga atgggcagtg cgtgtgccat gaaggattta tgggcaaaga ctgcaaggag   1680

caaagatgtc ccagtgactg tcatggccag ggccgctgcg tggacggcca gtgcatctgc   1740

cacgagggct tcacaggcct ggactgtggc cagcactcct gccccagtga ctgcaacaac   1800

ttaggacaat gcgtctcggg ccgctgcatc tgcaacgagg gctacagcgg agaagactgc   1860

tcagaggtgt ctcctcccaa agacctcgtt gtgacagaag tgacggaaga gacggtcaac   1920

ctggcctggg acaatgagat gcgggtcaca gagtaccttg tcgtgtacac gcccacccac   1980

gagggtggtc tggaaatgca gttccgtgtg cctggggacc agacgtccac catcatccag   2040

gagctggagc ctggtgtgga gtactttatc cgtgtatttg ccatcctgga gaacaagaag   2100

agcattcctg tcagcgccag ggtggccacg tacttacctg cacctgaagg cctgaaattc   2160

aagtccatca aggagacatc tgtggaagtg gagtgggatc ctctagacat tgcttttgaa   2220

acctgggaga tcatcttccg gaatatgaat aaagaagatg agggagagat caccaaaagc   2280

ctgaggaggc cagagacctc ttaccggcaa actggtctag ctcctgggca agagtatgag   2340

atatctctgc acatagtgaa aaacaatacc cggggccctg gcctgaagag ggtgaccacc   2400

acacgcttgg atgcccccag ccagatcgag gtgaaagatg tcacagacac cactgccttg   2460

atcacctggt tcaagcccct ggctgagatc gatggcattg agctgaccta cggcatcaaa   2520

gacgtgccag gagaccgtac caccatcgat ctcacagagg acgagaacca gtactccatc   2580

gggaacctga agcctgacac tgagtacgag gtgtccctca tctcccgcag aggtgacatg   2640

tcaagcaacc cagccaaaga gaccttcaca acaggcctcg atgctcccag gaatcttcga   2700

cgtgtttccc agacagataa cagcatcacc ctggaatgga ggaatggcaa ggcagctatt   2760

gacagttaca gaattaagta tgcccccatc tctggagggg accacgctga ggttgatgtt   2820

ccaaagagcc aacaagccac aaccaaaacc acactcacag gtctgaggcc gggaactgaa   2880

tatgggattg gagtttctgc tgtgaaggaa gacaaggaga gcaatccagc gaccatcaac   2940

gcagccacag agttggacac gcccaaggac cttcaggttt ctgaaactgc agagaccagc   3000

ctgaccctgc tctggaagac accgttggcc aaatttgacc gctaccgcct caattacagt   3060

ctccccacag gccagtgggt gggagtgcag cttccaagaa acaccacttc ctatgtcctg   3120

agaggcctgg aaccaggaca ggagtacaat gtcctcctga cagccgagaa aggcagacac   3180

aagagcaagc ccgcacgtgt gaaggcatcc actgaacaag cccctgagct ggaaaacctc   3240

accgtgactg aggttggctg ggatggcctc agactcaact ggaccgcggc tgaccaggcc   3300

tatgagcact ttatcattca ggtgcaggag gccaacaagg tggaggcagc tcggaacctc   3360

accgtgcctg gcagccttcg ggctgtggac ataccgggcc tcaaggctgc tacgccttat   3420

acagtctcca tctatggggt gatccagggc tatagaacac cagtgctctc tgctgaggcc   3480
```

```
tccacagggg aaactcccaa tttgggagag gtcgtggtgg ccgaggtggg ctgggatgcc   3540
ctcaaactca actggactgc tccagaaggg gcctatgagt actttttcat tcaggtgcag   3600
gaggctgaca cagtagaggc agcccagaac ctcaccgtcc caggaggact gaggtccaca   3660
gacctgcctg ggctcaaagc agccactcat tataccatca ccatccgcgg ggtcactcag   3720
gacttcagca caacccctct ctctgttgaa gtcttgacag aggaggttcc agatatggga   3780
aacctcacag tgaccgaggt tagctgggat gctctcagac tgaactggac cacgccagat   3840
ggaacctatg accagtttac tattcaggtc caggaggctg accaggtgga agaggctcac   3900
aatctcacgg ttcctggcag cctgcgttcc atggaaatcc caggcctcag ggctggcact   3960
ccttacacag tcaccctgca cggcgaggtc aggggccaca gcactcgacc ccttgctgta   4020
gaggtcgtca cagaggatct cccacagctg ggagatttag ccgtgtctga ggttggctgg   4080
gatggcctca gactcaactg gaccgcagct gacaatgcct atgagcactt tgtcattcag   4140
gtgcaggagg tcaacaaagt ggaggcagcc cagaacctca cgttgcctgg cagcctcagg   4200
gctgtggaca tcccgggcct cgaggctgcc acgccttata gagtctccat ctatggggtg   4260
atccggggct atagaacacc agtactctct gctgaggcct ccacagccaa agaacctgaa   4320
attggaaact taaatgtttc tgacataact cccgagagct tcaatctctc ctggatggct   4380
accgatggga tcttcgagac ctttaccatt gaaattattg attccaatag gttgctggag   4440
actgtggaat ataatatctc tggtgctgaa cgaactgccc atatctcagg gctacccccct  4500
agtactgatt ttattgtcta cctctctgga cttgctccca gcatccggac caaaaccatc   4560
agtgccacag ccacgacaga ggccctgccc cttctggaaa acctaaccat ttccgacatt   4620
aatccctacg ggttcacagt ttcctggatg gcatcggaga atgcctttga cagctttcta   4680
gtaacggtgg tggattctgg gaagctgctg gacccccagg aattcacact ttcaggaacc   4740
cagaggaagc tggagcttag aggcctcata actggcattg gctatgaggt tatggtctct   4800
ggcttcaccc aagggcatca aaccaagccc ttgagggctg agattgttac agaagccgaa   4860
ccggaagttg acaaccttct ggtttcagat gccaccccag acggtttccg tctgtcctgg   4920
acagctgatg aaggggtctt cgacaatttt gttctcaaaa tcagagatac caaaaagcag   4980
tctgagccac tggaaataac cctacttgcc cccgaacgta ccagggactt aacaggtctc   5040
agagaggcta ctgaatacga aattgaactc tatggaataa gcaaaggaag gcgatcccag   5100
acagtcagtg ctatagcaac aacagccatg ggctccccaa aggaagtcat tttctcagac   5160
atcactgaaa attcggctac tgtcagctgg agggcaccca cggcccaagt ggagagcttc   5220
cggattacct atgtgcccat tacaggaggt acaccctcca tggtaactgt ggacggaacc   5280
aagactcaga ccaggctggt gaaactcata cctggcgtgg agtaccttgt cagcatcatc   5340
gccatgaagg gctttgagga aagtgaacct gtctcagggt cattcaccac agctctggat   5400
ggcccatctg gcctggtgac agccaacatc actgactcag aagccttggc caggtggcag   5460
ccagccattg ccactgtgga cagttatgtc atctcctaca caggcgagaa agtgccagaa   5520
attacacgca cggtgtccgg gaacacagtg gagtatgctc tgaccgacct cgagcctgcc   5580
acggaataca cactgagaat ctttgcagag aaagggcccc agaagagctc aaccatcact   5640
gccaagttca caacagacct cgattctcca agagacttga ctgctactga ggttcagtcg   5700
gaaactgccc tccttacctg gcgacccccc cgggcatcag tcaccggtta cctgctggtc   5760
tatgaatcag tggatggcac agtcaaggaa gtcattgtgg gtccagatac cacctcctac   5820
agcctggcag acctgagccc atccacccac tacacagcca agatccaggc actcaatggg   5880
```

```
cccctgagga gcaatatgat ccagaccatc ttcaccacaa ttggactcct gtaccccttc   5940

cccaaggact gctcccaagc aatgctgaat ggagacacga cctctggcct ctacaccatt   6000

tatctgaatg gtgataaggc tcaggcgctg gaagtcttct gtgacatgac ctctgatggg   6060

ggtggatgga ttgtgttcct gagacgcaaa aacggacgcg agaacttcta ccaaaactgg   6120

aaggcatatg ctgctggatt tggggaccgc agagaagaat tctggcttgg gctggacaac   6180

ctgaacaaaa tcacagccca ggggcagtac gagctccggg tggacctgcg ggaccatggg   6240

gagacagcct ttgctgtcta tgacaagttc agcgtgggag atgccaagac tcgctacaag   6300

ctgaaggtgg aggggtacag tgggacagca ggtgactcca tggcctacca caatggcaga   6360

tccttctcca cctttgacaa ggacacagat tcagccatca ccaactgtgc tctgtcctac   6420

aaaggggctt tctggtacag gaactgtcac cgtgtcaacc tgatggggag atatggggac   6480

aataaccaca gtcagggcgt taactggttc cactggaagg gccacgaaca ctcaatccag   6540

tttgctgaga tgaagctgag accaagcaac ttcagaaatc ttgaaggcag gcgcaaacgg   6600

gca                                                                 6603


<210> SEQ ID NO 56
<211> LENGTH: 2201
<212> TYPE: PRT
<213> ORGANISM: Homo sapiens

<400> SEQUENCE: 56

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
```

```
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Leu Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670
```

```
Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp  Lys Thr Pro
        995                 1000                1005

Leu Ala  Lys Phe Asp Arg Tyr  Arg Leu Asn Tyr Ser  Leu Pro Thr
    1010                1015                1020

Gly Gln  Trp Val Gly Val Gln  Leu Pro Arg Asn Thr  Thr Ser Tyr
    1025                1030                1035

Val Leu  Arg Gly Leu Glu Pro  Gly Gln Glu Tyr Asn  Val Leu Leu
    1040                1045                1050

Thr Ala  Glu Lys Gly Arg His  Lys Ser Lys Pro Ala  Arg Val Lys
    1055                1060                1065

Ala Ser  Thr Glu Gln Ala Pro  Glu Leu Glu Asn Leu  Thr Val Thr
    1070                1075                1080

Glu Val  Gly Trp Asp Gly Leu  Arg Leu Asn Trp Thr  Ala Ala Asp
    1085                1090                1095
```

```
Gln Ala  Tyr Glu His Phe Ile  Ile Gln Val Gln Glu  Ala Asn Lys
    1100                 1105                 1110

Val Glu  Ala Ala Arg Asn Leu  Thr Val Pro Gly Ser  Leu Arg Ala
    1115                 1120                 1125

Val Asp  Ile Pro Gly Leu Lys  Ala Ala Thr Pro Tyr  Thr Val Ser
    1130                 1135                 1140

Ile Tyr  Gly Val Ile Gln Gly  Tyr Arg Thr Pro Val  Leu Ser Ala
    1145                 1150                 1155

Glu Ala  Ser Thr Gly Glu Thr  Pro Asn Leu Gly Glu  Val Val Val
    1160                 1165                 1170

Ala Glu  Val Gly Trp Asp Ala  Leu Lys Leu Asn Trp  Thr Ala Pro
    1175                 1180                 1185

Glu Gly  Ala Tyr Glu Tyr Phe  Phe Ile Gln Val Gln  Glu Ala Asp
    1190                 1195                 1200

Thr Val  Glu Ala Ala Gln Asn  Leu Thr Val Pro Gly  Gly Leu Arg
    1205                 1210                 1215

Ser Thr  Asp Leu Pro Gly Leu  Lys Ala Ala Thr His  Tyr Thr Ile
    1220                 1225                 1230

Thr Ile  Arg Gly Val Thr Gln  Asp Phe Ser Thr Thr  Pro Leu Ser
    1235                 1240                 1245

Val Glu  Val Leu Thr Glu Glu  Val Pro Asp Met Gly  Asn Leu Thr
    1250                 1255                 1260

Val Thr  Glu Val Ser Trp Asp  Ala Leu Arg Leu Asn  Trp Thr Thr
    1265                 1270                 1275

Pro Asp  Gly Thr Tyr Asp Gln  Phe Thr Ile Gln Val  Gln Glu Ala
    1280                 1285                 1290

Asp Gln  Val Glu Glu Ala His  Asn Leu Thr Val Pro  Gly Ser Leu
    1295                 1300                 1305

Arg Ser  Met Glu Ile Pro Gly  Leu Arg Ala Gly Thr  Pro Tyr Thr
    1310                 1315                 1320

Val Thr  Leu His Gly Glu Val  Arg Gly His Ser Thr  Arg Pro Leu
    1325                 1330                 1335

Ala Val  Glu Val Val Thr Glu  Asp Leu Pro Gln Leu  Gly Asp Leu
    1340                 1345                 1350

Ala Val  Ser Glu Val Gly Trp  Asp Gly Leu Arg Leu  Asn Trp Thr
    1355                 1360                 1365

Ala Ala  Asp Asn Ala Tyr Glu  His Phe Val Ile Gln  Val Gln Glu
    1370                 1375                 1380

Val Asn  Lys Val Glu Ala Ala  Gln Asn Leu Thr Leu  Pro Gly Ser
    1385                 1390                 1395

Leu Arg  Ala Val Asp Ile Pro  Gly Leu Glu Ala Ala  Thr Pro Tyr
    1400                 1405                 1410

Arg Val  Ser Ile Tyr Gly Val  Ile Arg Gly Tyr Arg  Thr Pro Val
    1415                 1420                 1425

Leu Ser  Ala Glu Ala Ser Thr  Ala Lys Glu Pro Glu  Ile Gly Asn
    1430                 1435                 1440

Leu Asn  Val Ser Asp Ile Thr  Pro Glu Ser Phe Asn  Leu Ser Trp
    1445                 1450                 1455

Met Ala  Thr Asp Gly Ile Phe  Glu Thr Phe Thr Ile  Glu Ile Ile
    1460                 1465                 1470

Asp Ser  Asn Arg Leu Leu Glu  Thr Val Glu Tyr Asn  Ile Ser Gly
    1475                 1480                 1485

Ala Glu  Arg Thr Ala His Ile  Ser Gly Leu Pro Pro  Ser Thr Asp
```

```
    1490                1495                1500

Phe Ile  Val Tyr Leu Ser Gly  Leu Ala Pro Ser Ile  Arg Thr Lys
    1505                1510                1515

Thr Ile  Ser Ala Thr Ala Thr  Thr Glu Ala Leu Pro  Leu Leu Glu
    1520                1525                1530

Asn Leu  Thr Ile Ser Asp Ile  Asn Pro Tyr Gly Phe  Thr Val Ser
    1535                1540                1545

Trp Met  Ala Ser Glu Asn Ala  Phe Asp Ser Phe Leu  Val Thr Val
    1550                1555                1560

Val Asp  Ser Gly Lys Leu Leu  Asp Pro Gln Glu Phe  Thr Leu Ser
    1565                1570                1575

Gly Thr  Gln Arg Lys Leu Glu  Leu Arg Gly Leu Ile  Thr Gly Ile
    1580                1585                1590

Gly Tyr  Glu Val Met Val Ser  Gly Phe Thr Gln Gly  His Gln Thr
    1595                1600                1605

Lys Pro  Leu Arg Ala Glu Ile  Val Thr Glu Ala Glu  Pro Glu Val
    1610                1615                1620

Asp Asn  Leu Leu Val Ser Asp  Ala Thr Pro Asp Gly  Phe Arg Leu
    1625                1630                1635

Ser Trp  Thr Ala Asp Glu Gly  Val Phe Asp Asn Phe  Val Leu Lys
    1640                1645                1650

Ile Arg  Asp Thr Lys Lys Gln  Ser Glu Pro Leu Glu  Ile Thr Leu
    1655                1660                1665

Leu Ala  Pro Glu Arg Thr Arg  Asp Leu Thr Gly Leu  Arg Glu Ala
    1670                1675                1680

Thr Glu  Tyr Glu Ile Glu Leu  Tyr Gly Ile Ser Lys  Gly Arg Arg
    1685                1690                1695

Ser Gln  Thr Val Ser Ala Ile  Ala Thr Thr Ala Met  Gly Ser Pro
    1700                1705                1710

Lys Glu  Val Ile Phe Ser Asp  Ile Thr Glu Asn Ser  Ala Thr Val
    1715                1720                1725

Ser Trp  Arg Ala Pro Thr Ala  Gln Val Glu Ser Phe  Arg Ile Thr
    1730                1735                1740

Tyr Val  Pro Ile Thr Gly Gly  Thr Pro Ser Met Val  Thr Val Asp
    1745                1750                1755

Gly Thr  Lys Thr Gln Thr Arg  Leu Val Lys Leu Ile  Pro Gly Val
    1760                1765                1770

Glu Tyr  Leu Val Ser Ile Ile  Ala Met Lys Gly Phe  Glu Glu Ser
    1775                1780                1785

Glu Pro  Val Ser Gly Ser Phe  Thr Thr Ala Leu Asp  Gly Pro Ser
    1790                1795                1800

Gly Leu  Val Thr Ala Asn Ile  Thr Asp Ser Glu Ala  Leu Ala Arg
    1805                1810                1815

Trp Gln  Pro Ala Ile Ala Thr  Val Asp Ser Tyr Val  Ile Ser Tyr
    1820                1825                1830

Thr Gly  Glu Lys Val Pro Glu  Ile Thr Arg Thr Val  Ser Gly Asn
    1835                1840                1845

Thr Val  Glu Tyr Ala Leu Thr  Asp Leu Glu Pro Ala  Thr Glu Tyr
    1850                1855                1860

Thr Leu  Arg Ile Phe Ala Glu  Lys Gly Pro Gln Lys  Ser Ser Thr
    1865                1870                1875

Ile Thr  Ala Lys Phe Thr Thr  Asp Leu Asp Ser Pro  Arg Asp Leu
    1880                1885                1890
```

```
Thr Ala  Thr Glu Val Gln Ser  Glu Thr Ala Leu Leu  Thr Trp Arg
    1895                 1900                 1905

Pro Pro  Arg Ala Ser Val Thr  Gly Tyr Leu Leu Val  Tyr Glu Ser
    1910                 1915                 1920

Val Asp  Gly Thr Val Lys Glu  Val Ile Val Gly Pro  Asp Thr Thr
    1925                 1930                 1935

Ser Tyr  Ser Leu Ala Asp Leu  Ser Pro Ser Thr His  Tyr Thr Ala
    1940                 1945                 1950

Lys Ile  Gln Ala Leu Asn Gly  Pro Leu Arg Ser Asn  Met Ile Gln
    1955                 1960                 1965

Thr Ile  Phe Thr Thr Ile Gly  Leu Leu Tyr Pro Phe  Pro Lys Asp
    1970                 1975                 1980

Cys Ser  Gln Ala Met Leu Asn  Gly Asp Thr Thr Ser  Gly Leu Tyr
    1985                 1990                 1995

Thr Ile  Tyr Leu Asn Gly Asp  Lys Ala Gln Ala Leu  Glu Val Phe
    2000                 2005                 2010

Cys Asp  Met Thr Ser Asp Gly  Gly Gly Trp Ile Val  Phe Leu Arg
    2015                 2020                 2025

Arg Lys  Asn Gly Arg Glu Asn  Phe Tyr Gln Asn Trp  Lys Ala Tyr
    2030                 2035                 2040

Ala Ala  Gly Phe Gly Asp Arg  Arg Glu Glu Phe Trp  Leu Gly Leu
    2045                 2050                 2055

Asp Asn  Leu Asn Lys Ile Thr  Ala Gln Gly Gln Tyr  Glu Leu Arg
    2060                 2065                 2070

Val Asp  Leu Arg Asp His Gly  Glu Thr Ala Phe Ala  Val Tyr Asp
    2075                 2080                 2085

Lys Phe  Ser Val Gly Asp Ala  Lys Thr Arg Tyr Lys  Leu Lys Val
    2090                 2095                 2100

Glu Gly  Tyr Ser Gly Thr Ala  Gly Asp Ser Met Ala  Tyr His Asn
    2105                 2110                 2115

Gly Arg  Ser Phe Ser Thr Phe  Asp Lys Asp Thr Asp  Ser Ala Ile
    2120                 2125                 2130

Thr Asn  Cys Ala Leu Ser Tyr  Lys Gly Ala Phe Trp  Tyr Arg Asn
    2135                 2140                 2145

Cys His  Arg Val Asn Leu Met  Gly Arg Tyr Gly Asp  Asn Asn His
    2150                 2155                 2160

Ser Gln  Gly Val Asn Trp Phe  His Trp Lys Gly His  Glu His Ser
    2165                 2170                 2175

Ile Gln  Phe Ala Glu Met Lys  Leu Arg Pro Ser Asn  Phe Arg Asn
    2180                 2185                 2190

Leu Glu  Gly Arg Arg Lys Arg  Ala
    2195                 2200
```

<210> SEQ ID NO 57
<211> LENGTH: 1134
<212> TYPE: DNA
<213> ORGANISM: Homo sapiens

<400> SEQUENCE: 57

```
atggcaactg ccctcccgcc gcgtctccag ccggtgcggg ggaacgagac cctgcgggag     60

cattaccagt acgtggggaa gttggcgggc aggctgaagg aggcctccga gggcagcacg    120

ctcaccaccg tgctcttctt ggtcatctgc agcttcatcg tcttggagaa cctgatggtt    180

ttgattgcca tctggaaaaa caataaattt cacaaccgca tgtacttttt cattggcaac    240

ctggctctct gcgacctgct ggccggcatc gcttacaagg tcaacattct gatgtctggc    300
```

```
aagaagacgt tcagcctgtc tcccacggtc tggttcctca gggagggcag tatgttcgtg    360

gcccttgggg cgtccacctg cagcttactg gccatcgcca tcgagcggca cttgacaatg    420

atcaaaatga ggccttacga cgccaacaag aggcaccgcg tcttcctcct gatcgggatg    480

tgctggctca ttgccttcac gctgggcgcc ctgcccattc tgggctggaa ctgcctgcac    540

aatctccctg actgctctac catcctgccc ctctactcca agaagtacat tgccttctgc    600

atcagcatct tcacggccat cctggtgacc atcgtgatcc tctacgcacg catctacttc    660

ctggtgaagt ccagcagccg taaggtggcc aaccacaaca actcggagcg gtccatggca    720

ctgctgcgga ccgtggtgat tgtggtgagc gtgttcatcg cctgctggtc cccactcttc    780

atcctcttcc tcattgatgt ggcctgcagg gtgcaggcgt gccccatcct cttcaaggct    840

cagtggttca tcgtgttggc tgtgctcaac tccgccatga acccggtcat ctacacgctg    900

gccagcaagg agatgcggcg ggccttcttc cgtctggtct gcaactgcct ggtcagggga    960

cggggggccc gcgcctcacc catccagcct gcgctcgacc caagcagaag taaatcaagc   1020

agcagcaaca atagcagcca ctctccgaag gtcaaggaag acctgcccca cacagccccc   1080

tcatcctgca tcatggacaa gaacgcagca cttcagaatg ggatcttctg caac         1134
```

<210> SEQ ID NO 58
<211> LENGTH: 378
<212> TYPE: PRT
<213> ORGANISM: Homo sapiens

<400> SEQUENCE: 58

```
Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
            20                  25                  30

Lys Glu Ala Ser Glu Gly Ser Thr Leu Thr Thr Val Leu Phe Leu Val
        35                  40                  45

Ile Cys Ser Phe Ile Val Leu Glu Asn Leu Met Val Leu Ile Ala Ile
    50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
        115                 120                 125

Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
            180                 185                 190

Ser Lys Lys Tyr Ile Ala Phe Cys Ile Ser Ile Phe Thr Ala Ile Leu
        195                 200                 205

Val Thr Ile Val Ile Leu Tyr Ala Arg Ile Tyr Phe Leu Val Lys Ser
    210                 215                 220

Ser Ser Arg Lys Val Ala Asn His Asn Asn Ser Glu Arg Ser Met Ala
```

```
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
            260                 265                 270

Ala Cys Pro Ile Leu Phe Lys Ala Gln Trp Phe Ile Val Leu Ala Val
        275                 280                 285

Leu Asn Ser Ala Met Asn Pro Val Ile Tyr Thr Leu Ala Ser Lys Glu
    290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Ser Asn Asn Ser Ser His Ser Pro Lys Val Lys
            340                 345                 350

Glu Asp Leu Pro His Thr Ala Pro Ser Ser Cys Ile Met Asp Lys Asn
        355                 360                 365

Ala Ala Leu Gln Asn Gly Ile Phe Cys Asn
    370                 375
```

<210> SEQ ID NO 59
<211> LENGTH: 1152
<212> TYPE: DNA
<213> ORGANISM: Homo sapiens

<400> SEQUENCE: 59

```
atggcagccc agaatggaaa caccagtttc acacccaact ttaatccacc ccaagaccat     60

gcctcctccc tctcctttaa cttcagttat ggtgattatg acctccctat ggatgaggat    120

gaggacatga ccaagacccg gaccttcttc gcagccaaga tcgtcattgg cattgcactg    180

gcaggcatca tgctggtctg cggcatcggt aactttgtct ttatcgctgc cctcacccgc    240

tataagaagt tgcgcaacct caccaatctg ctcattgcca acctggccat ctccgacttc    300

ctggtggcca tcatctgctg ccccttcgag atggactact acgtggtacg gcagctctcc    360

tgggagcatg gccacgtgct ctgtgcctcc gtcaactacc tgcgcaccgt ctccctctac    420

gtctccacca atgccttgct ggccattgcc attgacagat atctcgccat cgttcacccc    480

ttgaaaccac ggatgaatta tcaaacggcc tccttcctga tcgccttggt ctggatggtg    540

tccattctca ttgccatccc atcggcttac tttgcaacag aaacggtcct ctttattgtc    600

aagagccagg agaagatctt ctgtggccag atctggcctg tggatcagca gctctactac    660

aagtcctact tcctcttcat ctttggtgtc gagttcgtgg gccctgtggt caccatgacc    720

ctgtgctatg ccaggatctc ccgggagctc tggttcaagg cagtccctgg gttccagacg    780

gagcagattc gcaagcggct gcgctgccgc aggaagacgg tcctggtgct catgtgcatt    840

ctcacggcct atgtgctgtg ctgggcaccc ttctacggtt tcaccatcgt tcgtgacttc    900

ttccccactg tgttcgtgaa ggaaaagcac tacctcactg ccttctacgt ggtcgagtgc    960

atcgccatga gcaacagcat gatcaacacc gtgtgcttcg tgacggtcaa gaacaacacc   1020

atgaagtact tcaagaagat gatgctgctg cactggcgtc cctcccagcg ggggagcaag   1080

tccagtgctg accttgacct cagaaccaac ggggtgccca ccacagaaga ggtggactgt   1140

atcaggctga ag                                                       1152
```

<210> SEQ ID NO 60
<211> LENGTH: 384

<212> TYPE: PRT
<213> ORGANISM: Homo sapiens

<400> SEQUENCE: 60

Met Ala Ala Gln Asn Gly Asn Thr Ser Phe Thr Pro Asn Phe Asn Pro
1               5                   10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45

Phe Phe Ala Ala Lys Ile Val Ile Gly Ile Ala Leu Ala Gly Ile Met
    50                  55                  60

Leu Val Cys Gly Ile Gly Asn Phe Val Phe Ile Ala Ala Leu Thr Arg
65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
    130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190

Thr Glu Thr Val Leu Phe Ile Val Lys Ser Gln Glu Lys Ile Phe Cys
        195                 200                 205

Gly Gln Ile Trp Pro Val Asp Gln Gln Leu Tyr Tyr Lys Ser Tyr Phe
    210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
            260                 265                 270

Thr Val Leu Val Leu Met Cys Ile Leu Thr Ala Tyr Val Leu Cys Trp
        275                 280                 285

Ala Pro Phe Tyr Gly Phe Thr Ile Val Arg Asp Phe Phe Pro Thr Val
    290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
            340                 345                 350

Arg Pro Ser Gln Arg Gly Ser Lys Ser Ser Ala Asp Leu Asp Leu Arg
        355                 360                 365

Thr Asn Gly Val Pro Thr Thr Glu Glu Val Asp Cys Ile Arg Leu Lys
    370                 375                 380

<210> SEQ ID NO 61
<211> LENGTH: 885

<212> TYPE: DNA
<213> ORGANISM: Homo sapiens

<400> SEQUENCE: 61

```
atgctgcagg gccctggctc gctgctgctg ctcttcctcg cctcgcactg ctgcctgggc     60

tcggcgcgcg ggctcttcct ctttggccag cccgacttct cctacaagcg cagcaattgc    120

aagcccatcc ctgccaacct gcagctgtgc cacggcatcg aataccagaa catgcggctg    180

cccaacctgc tgggccacga gaccatgaag gaggtgctgg agcaggccgg cgcttggatc    240

ccgctggtca tgaagcagtg ccacccggac accaagaagt tcctgtgctc gctcttcgcc    300

cccgtctgcc tcgatgacct agacgagacc atccagccat gccactcgct ctgcgtgcag    360

gtgaaggacc gctgcgcccc ggtcatgtcc gccttcggct tcccctggcc cgacatgctt    420

gagtgcgacc gtttccccca ggacaacgac ctttgcatcc ccctcgctag cagcgaccac    480

ctcctgccag ccaccgagga agctccaaag gtatgtgaag cctgcaaaaa taaaaatgat    540

gatgacaacg acataatgga aacgctttgt aaaaatgatt ttgcactgaa aataaaagtg    600

aaggagataa cctacatcaa ccgagatacc aaaatcatcc tggagaccaa gagcaagacc    660

atttacaagc tgaacggtgt gtccgaaagg gacctgaaga aatcggtgct gtggctcaaa    720

gacagcttgc agtgcacctg tgaggagatg aacgacatca acgcgcccta tctggtcatg    780

ggacagaaac agggtgggga gctggtgatc acctcggtga agcggtggca gaaggggcag    840

agagagttca agcgcatctc ccgcagcatc cgcaagctgc agtgc                    885
```

<210> SEQ ID NO 62
<211> LENGTH: 295
<212> TYPE: PRT
<213> ORGANISM: Homo sapiens

<400> SEQUENCE: 62

```
Met Leu Gln Gly Pro Gly Ser Leu Leu Leu Leu Phe Leu Ala Ser His
1               5                   10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
```

-continued

```
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295


<210> SEQ ID NO 63
<211> LENGTH: 1011
<212> TYPE: DNA
<213> ORGANISM: Homo sapiens

<400> SEQUENCE: 63

atggaccaaa atgaacacag tcactgggga ccacatgcaa agggccaatg tgccagcaga      60

tctgagctga gaatcatcct ggtgggcaaa acaggaactg gcaaaagtgc tgcagggaac     120

agcatcctca ggaagcaagc atttgaatcg aagctgggtt cccagacctt gactaagact     180

tgcagcaaaa gtcagggaag ctggggaaat agagagattg tcattattga cacaccagat     240

atgttttctt ggaaggacca ctgtgaagct ctgtacaaag aggtgcagag gtgctacttg     300

ctgtctgcac caggacccca tgtgctgctc ctggtgactc agctgggccg ctatacctca     360

caggaccagc aggctgcaca gagggtgaag gagatctttg gagaggatgc catgggacac     420

acaattgtcc tctttaccca caaggaagac ctcaatggtg gctccctgat ggattacatg     480

cacgactcag ataacaaagc cctaagcaag ctggtggcag catgtggtgg gcgaatctgt     540

gcctttaata accgtgctga agggagcaat caggatgacc aagtgaagga actaatggac     600

tgtattgagg atctgttgat ggagaaaaat ggtgatcact ataccaatgg gttgtacagc     660

ctaatacaga ggtctaaatg tggacctgtg ggatcagatg aaagagtaaa ggaattcaaa     720

cagagcctta taaagtacat ggaaactcaa agaagttaca cagccttggc tgaagcaaac     780

tgcctaaaag gagccttaat caaaacacaa ctgtgtgttt tattttgtat tcagttgttt     840

ctcagattga taattctgtg gctttgcata ctgcacagca tgtgcaattt gttttgttgc     900

ttactcttta gtatgtgcaa tttattctgc agtttgctgt ttattatacc caaaaagtta     960

atgatatttt tgagaacagt tattagacta gaacgcaaga ctcctaggtt a             1011


<210> SEQ ID NO 64
<211> LENGTH: 337
<212> TYPE: PRT
<213> ORGANISM: Homo sapiens

<400> SEQUENCE: 64

Met Asp Gln Asn Glu His Ser His Trp Gly Pro His Ala Lys Gly Gln
1               5                   10                  15

Cys Ala Ser Arg Ser Glu Leu Arg Ile Ile Leu Val Gly Lys Thr Gly
            20                  25                  30

Thr Gly Lys Ser Ala Ala Gly Asn Ser Ile Leu Arg Lys Gln Ala Phe
        35                  40                  45

Glu Ser Lys Leu Gly Ser Gln Thr Leu Thr Lys Thr Cys Ser Lys Ser
```

```
    50                  55                  60

Gln Gly Ser Trp Gly Asn Arg Glu Ile Val Ile Ile Asp Thr Pro Asp
65                  70                  75                  80

Met Phe Ser Trp Lys Asp His Cys Glu Ala Leu Tyr Lys Glu Val Gln
                85                  90                  95

Arg Cys Tyr Leu Leu Ser Ala Pro Gly Pro His Val Leu Leu Leu Val
            100                 105                 110

Thr Gln Leu Gly Arg Tyr Thr Ser Gln Asp Gln Gln Ala Ala Gln Arg
        115                 120                 125

Val Lys Glu Ile Phe Gly Glu Asp Ala Met Gly His Thr Ile Val Leu
    130                 135                 140

Phe Thr His Lys Glu Asp Leu Asn Gly Gly Ser Leu Met Asp Tyr Met
145                 150                 155                 160

His Asp Ser Asp Asn Lys Ala Leu Ser Lys Leu Val Ala Ala Cys Gly
                165                 170                 175

Gly Arg Ile Cys Ala Phe Asn Asn Arg Ala Glu Gly Ser Asn Gln Asp
            180                 185                 190

Asp Gln Val Lys Glu Leu Met Asp Cys Ile Glu Asp Leu Leu Met Glu
        195                 200                 205

Lys Asn Gly Asp His Tyr Thr Asn Gly Leu Tyr Ser Leu Ile Gln Arg
    210                 215                 220

Ser Lys Cys Gly Pro Val Gly Ser Asp Glu Arg Val Lys Glu Phe Lys
225                 230                 235                 240

Gln Ser Leu Ile Lys Tyr Met Glu Thr Gln Arg Ser Tyr Thr Ala Leu
                245                 250                 255

Ala Glu Ala Asn Cys Leu Lys Gly Ala Leu Ile Lys Thr Gln Leu Cys
            260                 265                 270

Val Leu Phe Cys Ile Gln Leu Phe Leu Arg Leu Ile Ile Leu Trp Leu
        275                 280                 285

Cys Ile Leu His Ser Met Cys Asn Leu Phe Cys Cys Leu Leu Phe Ser
    290                 295                 300

Met Cys Asn Leu Phe Cys Ser Leu Leu Phe Ile Ile Pro Lys Lys Leu
305                 310                 315                 320

Met Ile Phe Leu Arg Thr Val Ile Arg Leu Glu Arg Lys Thr Pro Arg
                325                 330                 335

Leu


<210> SEQ ID NO 65
<211> LENGTH: 1173
<212> TYPE: DNA
<213> ORGANISM: Homo sapiens

<400> SEQUENCE: 65

atgttcccca atggcaccgc ctcctctcct tcctcctctc ctagccccag cccgggcagc      60

tgcggcgaag gcggcggcag caggggcccc ggggccggcg ctgcggacgg catggaggag     120

ccagggcgaa atgcgtccca gaacgggacc ttgagcgagg gccagggcag cgccatcctg     180

atctctttca tctactccgt ggtgtgcctg gtggggctgt gtgggaactc tatggtcatc     240

tacgtgatcc tgcgctatgc caagatgaag acggccacca acatctacat cctaaatctg     300

gccattgctg atgagctgct catgctcagc gtgcccttcc tagtcacctc cacgttgttg     360

cgccactggc ccttcggtgc gctgctctgc cgcctcgtgc tcagcgtgga cgcggtcaac     420

atgttcacca gcatctactg tctgactgtg ctcagcgtgg accgctacgt ggccgtggtg     480

catcccatca aggcggcccg ctaccgccgg cccaccgtgg ccaaggtagt aaacctgggc     540
```

```
gtgtgggtgc tatcgctgct cgtcatcctg cccatcgtgg tcttctctcg caccgcggcc    600

aacagcgacg gcacggtggc ttgcaacatg ctcatgccag agcccgctca acgctggctg    660

gtgggcttcg tgttgtacac atttctcatg ggcttcctgc tgcccgtggg ggctatctgc    720

ctgtgctacg tgctcatcat tgctaagatg cgcatggtgg ccctcaaggc cggctggcag    780

cagcgcaagc gctcggagcg caagatcacc ttaatggtga tgatggtggt gatggtgttt    840

gtcatctgct ggatgccttt ctacgtggtg cagctggtca acgtgtttgc tgagcaggac    900

gacgccacgg tgagtcagct gtcggtcatc ctcggctatg ccaacagctg cgccaacccc    960

atcctctatg gctttctctc agacaacttc aagcgctctt tccaacgcat cctatgcctc   1020

agctggatgg acaacgccgc ggaggagccg gttgactatt acgccaccgc gctcaagagc   1080

cgtgcctaca gtgtggaaga cttccaacct gagaacctgg agtccggcgg cgtcttccgt   1140

aatggcacct gcacgtcccg gatcacgacg ctc                                1173
```

<210> SEQ ID NO 66
<211> LENGTH: 391
<212> TYPE: PRT
<213> ORGANISM: Homo sapiens

<400> SEQUENCE: 66

```
Met Phe Pro Asn Gly Thr Ala Ser Ser Pro Ser Ser Ser Pro Ser Pro
1               5                   10                  15

Ser Pro Gly Ser Cys Gly Glu Gly Gly Gly Ser Arg Gly Pro Gly Ala
            20                  25                  30

Gly Ala Ala Asp Gly Met Glu Glu Pro Gly Arg Asn Ala Ser Gln Asn
        35                  40                  45

Gly Thr Leu Ser Glu Gly Gln Gly Ser Ala Ile Leu Ile Ser Phe Ile
    50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
```

```
        260                 265                 270

Val Met Met Val Val Met Val Phe Val Ile Cys Trp Met Pro Phe Tyr
    275                 280                 285

Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
    370                 375                 380

Thr Ser Arg Ile Thr Thr Leu
385                 390


<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

tcccttggtc cactcacaga ct                                              22


<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

tgtgtaaagt acggagcgaa gttg                                            24


<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

tgccttgcac agcctcgcaa tgagc                                           25


<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

tgtgaaaggc acagcagtcc cga                                             23


<210> SEQ ID NO 71
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

tcagcatggg ctgctacaac ggt                                              23


<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

ctcaagtctg tttcttcttc                                                  20


<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      antigenic peptide

<400> SEQUENCE: 73

Arg Arg Tyr Lys Ile His Pro Asp Phe Ser Pro Ser Val Lys Gln Cys
1               5                   10                  15


<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl anthranilic acid
<220> FEATURE:
<221> NAME/KEY: MOD_RES
<222> LOCATION: (7)..(7)
<223> OTHER INFORMATION: Norvaline
<220> FEATURE:
<221> NAME/KEY: MOD_RES
<222> LOCATION: (8)..(8)
<223> OTHER INFORMATION: Lys(dinitrophenol)
<220> FEATURE:
<223> OTHER INFORMATION: C-term amidated

<400> SEQUENCE: 74

Xaa Pro Lys Pro Leu Ala Xaa Trp Lys
1               5
```

PREVENTIVE/REMEDY FOR RESPIRATORY DISEASES

CROSS-REFERENCES TO RELATED APPLICATIONS

The present application is a 35 U.S.C. §371 national stage of PCT application PCT/JP05/06444, filed Mar. 25, 2005, which claims priority of Japanese Application Serial Number 2004-092064, filed Mar. 26, 2004.

TECHNICAL FIELD

The present invention relates to prophylactic/therapeutic agents and diagnostic agents for respiratory diseases, screening of the prophylactic/therapeutic agents for respiratory diseases, etc.

BACKGROUND ART

As the smoking generation is aged and their average life expectancy is prolonged, chronic obstructive pulmonary disease, chronic bronchitis, pulmonary emphysema, diffuse panbronchiolitis, intrinsic asthma, etc. are considered to be major diseases in respiratory diseases in the future.

It is revealed that smoking can be an evident causative factor of chronic obstructive pulmonary disease. Obstructive disorders proceed by smoking, and the degree of the disorders depends on the number of cigarettes smoked. Specifically, the disorders proceed more easily as smoking is initiated at an early age. In addition, a dose correlation between smoking and bronchial gland hyperplasia has been confirmed.

In animal experiments, there are many reports that emphysematous change can be caused by smoking.

Physiological changes in chronic obstructive pulmonary disease (hereinafter abbreviated sometimes as COPD) are characterized with unique abnormal findings observed in 3 regions, that is, central airway, peripheral airway, and lung parenchyma. In lesions in the central airway, hyperplasia of goblet cells and morphological change in secretary tissues such as growth and hypertrophy of cells in submucosal glands are observed. With respect to inflammatory cells, an increase in macrophages and activated T lymphocytes is indicated in the airway mucus. As lesions in the region of bronchiole, mucus plugging in the airway lumen, abnormal formation of goblet cells in the airway epithelium, infiltration of inflammatory cells in the airway wall, and thickening and fibrosis of smooth muscles are observed. In alveolar parenchyma, pulmonary emphysema lesions defined by destruction and disappearance of alveolus and expansion of the air space are observed. Imbalance between protease and antiprotease is considered involved in these lesions. Any of these physiological changes cause airway obstruction.

Cholesterol 25-hydroxylase (CH25H) (GenBank Accession NO. NM_003956) is one kind of cholesterol hydroxylase and has an activity of converting cholesterol into 25-hydroxycholesterol (25-HC) (J. Biol. Chem. 273:34316-34327 (1998)). The product 25-hydroxycholesterol is known to induce interleukin-β in macrophage (Eur. J. Clin. Invest. 32:35-42 (2002)).

Prostate differentiation factor (GDF15, PLAB) (GenBank Accession NO. AF003934) has an effect of promoting a neutrophil infiltration action via interleukin 8 (J. Immunol. 171: 2057-2065 (2003)).

Matrix metalloproteinase 19 (MMP19) (GenBank Accession NO. U38321) is an enzyme having a proteolysis enzyme activity (J. Biol. Chem. 272:4281-4286 (1997)).

Under these circumstances, there is desire for the development of prophylactic/therapeutic agents for respiratory diseases (for example, chronic obstructive pulmonary disease etc.), which are excellent with less side effects, as well as diagnostic agents for respiratory diseases.

DISCLOSURE OF THE INVENTION

In order to solve the problems described above, the present inventors made extensive studies and have found a gene whose expression is significantly increased or decreased in lung tissue in a patient with lung cancer with a complication of chronic obstructive pulmonary disease (COPD), and as a result of further examination on the basis of this finding, the present invention has been accomplished.

That is, the present invention relates to:

(1) A prophylactic/therapeutic agent for respiratory diseases, comprising a compound or its salt that inhibits the activity of a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, its partial peptide, or a salt thereof.

(1a) A prophylactic/therapeutic agent for respiratory diseases, comprising a compound or its salt that inhibits the activity of a protein comprising the same or substantially the same amino acid sequence as the amino acid sequence represented by SEQ ID NO: 2, its partial peptide, or a salt thereof.

(1b) A prophylactic/therapeutic agent for respiratory diseases, comprising a compound or its salt that inhibits the activity of a protein comprising the same or substantially the same amino acid sequence as the amino acid sequence represented by SEQ ID NO: 4, its partial peptide, or a salt thereof.

(1c) A prophylactic/therapeutic agent for respiratory diseases, comprising a compound or its salt that inhibits the activity of a protein comprising the same or substantially the same amino acid sequence as the amino acid sequence represented by SEQ ID NO: 30, its partial peptide, or a salt thereof.

(2) The agent according to (1), wherein the compound is a compound that inhibits the activity of a protein comprising the amino acid sequence represented by SEQ ID NO: 2, its partial peptide, or a salt thereof.

(3) A prophylactic/therapeutic agent for respiratory diseases, comprising a compound or its salt that inhibits the expression of a gene for a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, its partial peptide, or a salt thereof.

(3a) A prophylactic/therapeutic agent for respiratory diseases, comprising a compound or its salt that inhibits the expression of a gene for a protein comprising the same or substantially the same amino acid sequence as the amino acid sequence represented by SEQ ID NO: 2, its partial peptide, or a salt thereof.

(3b) A prophylactic/therapeutic agent for respiratory diseases, comprising a compound or its salt that inhibits the expression of a gene for a protein comprising the same or substantially the same amino acid sequence as the amino acid sequence represented by SEQ ID NO: 4, its partial peptide, or a salt thereof.

(3c) A prophylactic/therapeutic agent for respiratory diseases, comprising a compound or its salt that inhibits the expression of a gene for a protein comprising the same or substantially the same amino acid sequence as the amino acid sequence represented by SEQ ID NO: 30, its partial peptide, or a salt thereof.

(4) The agent according to (3), wherein the compound is a compound that inhibits the expression of a gene for a protein comprising the amino acid sequence represented by SEQ ID NO: 2, its partial peptide, or a salt thereof.

(5) An antisense polynucleotide comprising the entire or part of a base sequence complementary or substantially complementary to a base sequence of a polynucleotide encoding a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, or its partial peptide.

(5a) An antisense polynucleotide comprising the entire or part of a base sequence complementary or substantially complementary to a base sequence of a polynucleotide encoding a protein comprising the same or substantially the same amino acid sequence as the amino acid sequence represented by SEQ ID NO: 2, SEQ ID NO: 4 or SEQ ID NO: 30, or its partial peptide.

(6) A pharmaceutical preparation comprising the antisense polynucleotide according to (5).

(6a) A pharmaceutical preparation comprising the antisense polynucleotide according to (5a).

(7) The pharmaceutical preparation according to (6), which is a prophylactic/therapeutic agent for respiratory diseases.

(7a) The pharmaceutical preparation according to (6a), which is a prophylactic/therapeutic agent for respiratory diseases.

(8) An antibody against a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 or SEQ ID NO: 62, or against its partial peptide or a salt thereof.

(8a) An antibody against a protein comprising the same or substantially the same amino acid sequence as the amino acid sequence represented by SEQ ID NO: 2, SEQ ID NO: 4 or SEQ ID NO: 30, or against its partial peptide or against a salt thereof.

(9) A pharmaceutical preparation comprising the antibody according to (8).

(9a) A pharmaceutical preparation comprising the antibody according to (8a).

(10) The pharmaceutical preparation according to (9), which is a prophylactic/therapeutic agent for respiratory diseases.

(10a) The pharmaceutical preparation according to (9a), which is a prophylactic/therapeutic agent for respiratory diseases.

(11) A diagnostic agent comprising the antibody according to (8).

(12) The diagnostic agent according to (11), which is a diagnostic agent for respiratory diseases.

(13) A diagnostic agent for respiratory diseases comprising a polynucleotide encoding a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, or its partial peptide.

(14) A prophylactic/therapeutic agent for respiratory diseases, which comprises a compound or its salt having an action of inhibiting a cholesterol hydroxylation activity.

(15) A method of screening a prophylactic/therapeutic agent for respiratory diseases, which comprises using a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, its partial peptide, or a salt thereof.

(15a) A method of screening a prophylactic/therapeutic agent for respiratory diseases, which comprises using a protein comprising the same or substantially the same amino acid sequence as the amino acid sequence represented by SEQ ID NO: 2, its partial peptide, or a salt thereof.

(15b) A method of screening a prophylactic/therapeutic agent for cancer, which comprises using a protein comprising the same or substantially the same amino acid sequence as the amino acid sequence represented by SEQ ID NO: 4, its partial peptide, or a salt thereof.

(15c) A method of screening a prophylactic/therapeutic agent for cancer, which comprises using a protein comprising the same or substantially the same amino acid sequence as the amino acid sequence represented by SEQ ID NO: 30, its partial peptide, or a salt thereof.

(15d) A prophylactic/therapeutic agent for respiratory diseases, which is obtained by using the screening method according to (15) to (15c).

(16) The screening method according to (15), which comprises using a protein comprising the amino acid sequence represented by SEQ ID NO: 2, its partial peptide, or a salt thereof.

(17) A kit for screening a prophylactic/therapeutic agent for respiratory diseases, comprising a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, its partial peptide, or a salt thereof.

(17a) A kit for screening a prophylactic/therapeutic agent for respiratory diseases, comprising a protein comprising the same or substantially the same amino acid sequence as the amino acid sequence represented by SEQ ID NO: 2, its partial peptide, or a salt thereof.

(17b) A kit for screening a prophylactic/therapeutic agent for respiratory diseases, comprising a protein comprising the same or substantially the same amino acid sequence as the amino acid sequence represented by SEQ ID NO: 4, its partial peptide, or a salt thereof.

(17c) A kit for screening a prophylactic/therapeutic agent for respiratory diseases, comprising a protein comprising the same or substantially the same amino acid sequence as the amino acid sequence represented by SEQ ID NO: 30, its partial peptide, or a salt thereof.

(17d) A prophylactic/therapeutic agent for respiratory diseases, which is obtainable by using the screening kit according to (17) to (17c).

(18) The screening kit according to (17), which comprises a protein comprising the amino acid sequence represented by SEQ ID NO: 2, its partial peptide, or a salt thereof.

(19) A method of screening a prophylactic/therapeutic agent for respiratory diseases, which comprises using a polynucleotide encoding a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, or its partial peptide.

(19a) A method of screening a prophylactic/therapeutic agent for respiratory diseases, which comprises using a polynucleotide encoding a protein comprising the same or substantially the same amino acid sequence as the amino acid sequence represented by SEQ ID NO: 2, or its partial peptide.

(19b) A method of screening a prophylactic/therapeutic agent for respiratory diseases, which comprises using a polynucleotide encoding a protein comprising the same or substantially the same amino acid sequence as the amino acid sequence represented by SEQ ID NO: 4, or its partial peptide.

(19c) A method of screening a prophylactic/therapeutic agent for respiratory diseases, which comprises using a polynucleotide encoding a protein comprising the same or substantially the same amino acid sequence as the amino acid sequence represented by SEQ ID NO: 30, or its partial peptide.

(19d) A prophylactic/therapeutic agent for respiratory diseases, which is obtainable by using the screening method according to (19) to (19c).

(20) The screening method according to (19), which comprises using a polynucleotide encoding a protein comprising the amino acid sequence represented by SEQ ID NO: 2 or its partial peptide.

(21) A kit for screening a prophylactic/therapeutic agent for respiratory diseases, comprising a polynucleotide encoding a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, or its partial peptide.

(21a) A kit for screening a prophylactic/therapeutic agent for respiratory diseases, comprising a polynucleotide encoding a protein comprising the same or substantially the same amino acid sequence as the amino acid sequence represented by SEQ ID NO: 2, or its partial peptide.

(21b) A kit for screening a prophylactic/therapeutic agent for respiratory diseases, comprising the same or substantially the same amino acid sequence as the amino acid sequence represented by SEQ ID NO: 4.

(21c) A kit for screening a prophylactic/therapeutic agent for respiratory diseases, comprising a polynucleotide encoding a protein comprising the same or substantially the same amino acid sequence as the amino acid sequence represented by SEQ ID NO: 30, or its partial peptide.

(21d) A prophylactic/therapeutic agent for respiratory diseases, which is obtainable by using the screening kit according to (21) to (21c).

(22) The screening kit according to (21), comprising a polynucleotide encoding a protein comprising the amino acid sequence represented by SEQ ID NO: 2, or its partial peptide.

(23) A method of preventing/treating respiratory diseases, which comprises administering to a mammal an effective dose of a compound or its salt that inhibits the activity of a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 or SEQ ID NO: 62, or its partial peptide or a salt thereof, or a compound or its salt that inhibits the expression of a gene for the protein.

(24) The method according to (23), wherein the compound is a compound that inhibits the activity of a protein comprising the amino acid sequence represented by SEQ ID NO: 2, its partial peptide, or a salt thereof, or a compound that inhibits the expression of a gene for the protein.

(25) A method of preventing/treating respiratory diseases, which comprises inhibiting the activity of a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, or SEQ ID NO: 62, its partial peptide, or a salt thereof, or inhibiting the expression of a gene for said protein.

(26) The method according to (25), wherein the activity of a protein comprising the amino acid sequence represented by SEQ ID NO: 2, its partial peptide, or a salt thereof, or the expression of a gene for the protein, is inhibited.

(27) Use of a compound or its salt that inhibits the activity of a protein comprising the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 or SEQ ID NO: 62, or its partial peptide or a salt thereof, or a compound or its salt that inhibits the expression of a gene for the protein, to manufacture a prophylactic/therapeutic agent for respiratory diseases.

(28) Use according to (27), wherein the compound is a compound that inhibits the activity of a protein comprising the amino acid sequence represented by SEQ ID NO: 2, its partial peptide, or a salt thereof, or a compound that inhibits the expression of a gene for the protein.

(29) A prophylactic/therapeutic agent for respiratory diseases, which comprises a compound or a salt thereof that promotes the activity of a protein comprising the same or substantially the same amino acid sequence as the amino acid sequence represented by SEQ ID NO: 64 or SEQ ID NO: 66, or its partial peptide or a salt thereof.

(30) A prophylactic/therapeutic agent for respiratory diseases, which comprises a compound or a salt thereof that promotes the expression of a gene for a protein comprising the same or substantially the same amino acid sequence represented by SEQ ID NO: 64 or SEQ ID NO: 66, or its partial peptide or a salt thereof.

(31) An antibody against a protein comprising the same or substantially the same amino acid sequence as the amino acid sequence represented by SEQ ID NO: 64 or SEQ ID NO: 66, or against its partial peptide or against a salt thereof.

(32) A diagnostic agent comprising the antibody according to (31).

(33) The diagnostic agent according to (34) [sic], which is a diagnostic agent for respiratory diseases.

(34) A diagnostic agent for respiratory diseases, comprising a polynucleotide encoding a protein comprising the same or substantially the same amino acid sequence as the amino acid sequence represented by SEQ ID NO: 64 or SEQ ID NO: 66, or its partial peptide.

(35) A method of screening a prophylactic/therapeutic agent for respiratory diseases, which comprises using a protein comprising the same or substantially the same amino acid sequence as the amino acid sequence represented by SEQ ID NO: 64 or SEQ ID NO: 66, its partial peptide, or a salt thereof.

(36) A kit for screening a prophylactic/therapeutic agent for respiratory diseases, comprising a protein comprising the same or substantially the same amino acid sequence as the amino acid sequence represented by SEQ ID NO: 64 or SEQ ID NO: 66, its partial peptide, or a salt thereof.

(37) A method of screening a prophylactic/therapeutic agent for respiratory diseases, which comprises using a polynucleotide encoding a protein comprising the same or substantially the same amino acid sequence as the amino acid sequence represented by SEQ ID NO: 64 or SEQ ID NO: 66, or its partial peptide.

(38) A kit for screening a prophylactic/therapeutic agent for respiratory diseases, comprising a polynucleotide encoding a protein comprising the same or substantially the same amino acid sequence as the amino acid sequence represented by SEQ ID NO: 64 or SEQ ID NO: 66, or its partial peptide.

(39) A method of preventing/treating respiratory diseases, which comprises administering to a mammal an effective dose of a compound or its salt that promotes the activity of a protein comprising the same or substantially the same amino acid sequence as the amino acid sequence represented by SEQ ID NO: 64 or SEQ ID NO: 66, or its partial peptide or a salt thereof, or a compound or its salt that promotes the expression of a gene for the protein.

(40) A method of preventing/treating respiratory diseases, which comprises promoting the activity of a protein comprising the same or substantially the same amino acid sequence as the amino acid sequence represented by SEQ ID NO: 64 or SEQ ID NO: 66, or its partial peptide or a salt thereof, or promoting the expression of a gene for the protein.

(41) Use of a compound or its salt that promotes the activity of a protein comprising the same or substantially the same amino acid sequence as the amino acid sequence represented by SEQ ID NO: 64 or SEQ ID NO: 66, or its partial peptide or a salt thereof, or a compound or its salt that promotes the expression of a gene for the protein, to manufacture a prophylactic/therapeutic agent for respiratory diseases.

BEST MODE FOR CARRYING OUT THE INVENTION

Figure 1:
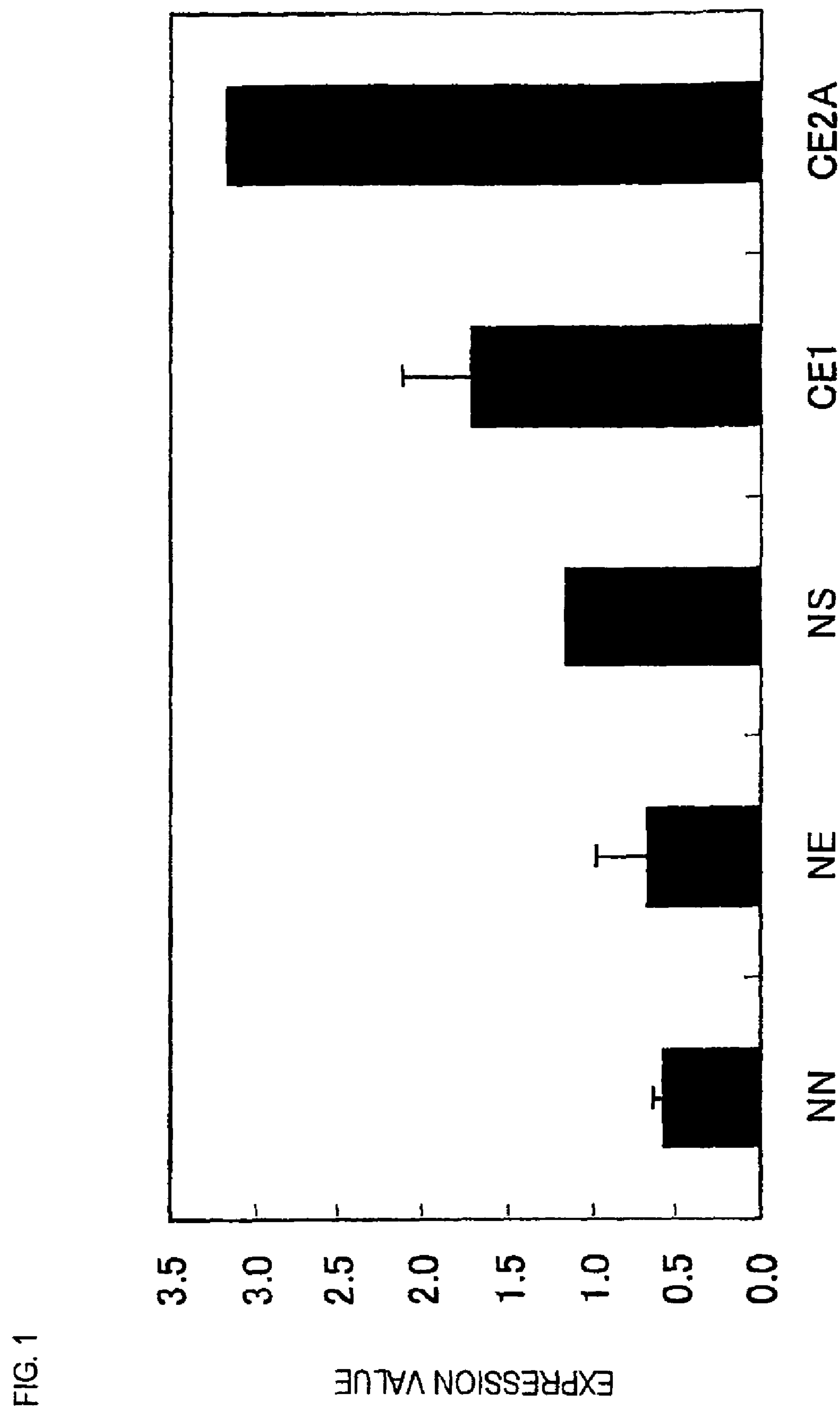
FIG. 1 is a graph showing the expression level of CH25H gene in each group.

The protein, which has the same or substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66 (hereinafter the protein is sometimes referred to as the protein of the present invention or the protein used in the present invention) may be any protein derived from any cells of human and warm-blooded animals (e.g., guinea pig, rat, mouse, fowl, rabbit, swine, ovine, bovine, simian, etc.) (such as hepatocytes, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; the protein may also be a synthetic protein.

The amino acid sequence having substantially the same amino acid sequence as that represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66 includes amino acid sequences having at least about 50% homology, preferably at least about 60% homology, more preferably at least about 70% homology, much more preferably at least about 80% homology, further much more preferably at least about 90% homology and most preferably at least about 95% homology, to the amino acid sequence shown by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66; and so on.

Homology of the amino acid sequences can be determined under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

Preferred examples of the protein comprising substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66 include proteins having substantially the same amino acid sequence as the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66 and having an activity of substantially the same nature as that of the protein comprising the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, and the like.

The activity of substantially the same nature as that of the protein comprising the amino acid sequence represented by SEQ ID NO: 2 includes, for example, a cholesterol hydroxylation activity.

The activity of substantially the same nature as that of the protein comprising the amino acid sequence represented by SEQ ID NO: 4 includes, for example, a neutrophil infiltration activity via interleukin 8 production from macrophage.

The activity of substantially the same nature as that of the protein comprising the amino acid sequence represented by SEQ ID NO: 30 includes, for example, a proteolysis enzyme activity.

The "substantially the same nature" is used to mean that the characteristics of these activities is equivalent in terms of its nature (e.g., physiologically or pharmacologically). Thus, the cholesterol hydroxylation activity, neutrophil infiltration activity and proteolysis enzyme activity described above are preferably equivalent (e.g., about 0.01 to 100 times, preferably about 0.1 to 10 times, more preferably 0.5 to 2 times), but differences in degree such as a level of these activities, quantitative factors such as a molecular weight of the protein may be present and allowable.

The cholesterol hydroxylation activity can be assayed by methods known per se, for example, a method described in J. Biol. Chem. 273:34316-34327 (1998) or with its modifications.

Specifically, the protein of the present invention (preferably a protein comprising the same or substantially the same amino acid sequence as the amino acid sequence represented by SEQ ID NO: 2) is reacted with a labeled cholesterol substrate, and the product is separated from the substrate by thin layer chromatography, and the amount of the product (for example, radioactivity) is measured to determine the cholesterol hydroxylation activity. As the labeled cholesterol substrate, cholesterol labeled with a radioisotope (for example, [$^{125}$I], [$^{131}$I], [$^{3}$H], [$^{14}$C] etc.) is used. Measurement of the radioactivity is carried out in a known method using a scintillation counter etc.

Measurement of the neutrophil infiltration activity can be carried out according to methods known per se, for example a method described in J. Immunol. 171:2057-2065 (2003) or with its modifications.

The protein of the present invention (preferably a protein comprising the same or substantially the same amino acid sequence as the amino acid sequence represented by SEQ ID NO: 4) and interleukin 8, together with a cell culture medium, are introduced into a lower chamber of Trans-well (manufactured by Corning), while neutrophils are added to an upper chamber, and the number of neutrophils passing through an endothelial cell layer and infiltrating from the upper chamber to the lower chamber is determined, whereby the neutrophil infiltration activity is measured.

The proteolysis enzyme activity can be assayed by methods known per se, for example, a method described in J. Biol. Chem. 272:4281-4286 (1997) or with its modifications.

The protein of the present invention (preferably a protein comprising the same or substantially the same amino acid sequence as the amino acid sequence represented by SEQ ID NO: 30) is reacted with a labeled substrate peptide, and the amount of the substrate peptide decomposed (for example, fluorescence intensity) is measured, whereby the proteolysis activity is measured. As the labeled substrate peptide, use is made of, for example, a substrate peptide (for example, Nma-Pro-Lys-Pro-Leu-Ala-Nva-Trp-Lys (Dnp)-$NH_2$ (SEQ ID NO: 74), Nma: N-methyl anthranilic acid etc.) labeled with a fluorescent substance (for example, fluorescamine, fluorescein isocyanate etc.). The fluorescence intensity is measured according to methods known in the art, for example a method using a fluorescence measuring apparatus.

Examples of the protein used in the present invention include so-called muteins such as proteins comprising (i) the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, of which at least 1 or 2 (e.g., about 1 to about 100, preferably about 1 to about 30, more preferably about 1 to about 10 and most preferably several (1 to 5)) amino acids are deleted; (ii) the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, to which at least 1 or 2 (e.g., about 1 to about 100, preferably about 1 to about 30, more preferably about 1 to about 10 and most preferably several (1 to 5)) amino acids are added; (iii) the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, in which at least 1 or 2 (e.g., about 1 to about 100, preferably about 1 to about 30, more preferably about 1 to about 10 and most preferably several (1 to 5)) amino acids are inserted; (iv) the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, in which at least 1 or 2 (e.g., about 1 to about 100, preferably about 1 to about 30, more preferably about 1 to about 10 and most preferably several (1 to 5)) amino acids are substituted by other amino acids; or (v) a combination of these amino acid sequences; and the like.

Where the amino acid sequence contains insertion, deletion or substitution as described above, the position of its insertion, deletion or substitution is not particularly limited.

Throughout the specification, the proteins are represented in accordance with the conventional way of describing proteins, that is, the N-terminus (amino terminus) at the left hand and the C-terminus (carboxyl terminus) at the right hand. In the protein used in the present invention, the C-terminus may be in any form of a carboxyl group (—COOH), a carboxylate (—COO—), an amide (—$CONH_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc. or an α-naphthyl-$C_{1-2}$ alkyl group such as ax-naphthylmethyl, etc.; pivaloyloxymethyl and the like.

Where the protein used in the present invention contains a carboxyl group (or a carboxylate) at a position other than the C-terminus, the carboxyl group may be amidated or esterified and such an amide or ester is also included within the protein used in the present invention. Examples of the ester group in this case may be the C-terminal esters described above, etc.

Furthermore, examples of the protein used in the present invention include those in which the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

Specific examples of the protein used in the present invention include, for example, a protein comprising the amino acid sequence represented by SEQ ID NO: 2, a protein comprising the amino acid sequence represented by SEQ ID NO: 4, a protein comprising the amino acid sequence represented by SEQ ID NO: 6, a protein comprising the amino acid sequence represented by SEQ ID NO: 8, a protein comprising the amino acid sequence represented by SEQ ID NO: 10, a protein comprising the amino acid sequence represented by SEQ ID NO: 12, a protein comprising the amino acid sequence represented by SEQ ID NO: 14, a protein comprising the amino acid sequence represented by SEQ ID NO: 16, a protein comprising the amino acid sequence represented by SEQ ID NO: 18, a protein comprising the amino acid sequence represented by SEQ ID NO: 20, a protein comprising the amino acid sequence represented by SEQ ID NO: 22, a protein comprising the amino acid sequence represented by SEQ ID NO: 24, a protein comprising the amino acid sequence represented by SEQ ID NO: 26, a protein comprising the amino acid sequence represented by SEQ ID NO: 28, a protein comprising the amino acid sequence represented by SEQ ID NO: 30, a protein comprising the amino acid sequence represented by SEQ ID NO: 32, a protein comprising the amino acid sequence represented by SEQ ID NO: 34, a protein comprising the amino acid sequence represented by SEQ ID NO: 36, a protein comprising the amino acid sequence represented by SEQ ID NO: 38, a protein comprising the amino acid sequence represented by SEQ ID NO: 40, a protein comprising the amino acid sequence represented by SEQ ID NO: 42, a protein comprising the amino acid sequence represented by SEQ ID NO: 44, a protein comprising the amino acid sequence represented by SEQ ID NO: 46, a protein comprising the amino acid sequence represented by SEQ ID NO: 48, a protein comprising the amino acid sequence represented by SEQ ID NO: 50, a protein comprising the amino acid sequence represented by SEQ ID NO: 52, a protein comprising the amino acid sequence represented by SEQ ID NO: 54, a protein comprising the amino acid sequence represented by SEQ ID NO: 56, a protein comprising the amino acid sequence represented by SEQ ID NO: 58, a protein comprising the amino acid sequence represented by SEQ ID NO: 60, a protein comprising the amino acid sequence represented by SEQ ID NO: 62, a protein comprising the amino acid sequence represented by SEQ ID NO: 64, a protein comprising the amino acid sequence represented by SEQ ID NO: 66, etc.

The partial peptide of the protein used in the present invention may be any peptide as long as it is a partial peptide of the protein used in the present invention described above and preferably has the property equivalent to that of the protein used in the present invention described above.

Specific examples include a peptide having an amino acid sequence in positions 1 to 272 in the amino acid sequence represented by SEQ ID NO: 2, a peptide having an amino acid sequence in positions 1 to 308 in the amino acid sequence represented by SEQ ID NO: 4, etc. Preferably used are peptides having, e.g., at least 20, preferably at least 50, more preferably at least 70, much more preferably at least 100, and most preferably at least 200, amino acids in the constituent amino acid sequence of the protein used in the present invention, and the like.

The partial peptide used in the present invention may contain deletion of at least 1 or 2 (preferably about 1 to about 10 and most preferably several (1 to 5)) amino acids in the amino acid sequence; addition of at least 1 or 2 (preferably about 1 to about 20, more preferably about 1 to about 10 and most preferably several (1 to 5)) amino acids in the amino acid sequence; insertion of at least 1 or 2 (preferably about 1 to about 20, more preferably about 1 to about 10 and most preferably several (1 to 5)) amino acids in the amino acid sequence; or substitution of at least 1 or 2 (preferably about 1 to about 10, more preferably about several amino acids and most preferably several (1 to 5)) amino acids in the amino acid sequence by other amino acids.

In the partial peptide used in the present invention, the C-terminus may be in any form of a carboxyl group (—COOH), a carboxylate (—COO—), an amide (—$CONH_2$) or an ester (—COOR).

Furthermore, the partial peptide used in the present invention includes those having a carboxyl group (or a carboxylate) at a position other than the C-terminus, those having an amino group protected with a protecting group at the N-terminal amino acid residues (e.g., methionine residue); those being cleaved at the N-terminal region in vivo and with the glutamyl group thus formed being pyroglutaminated; those having a substituent on the side chain of an amino acid in the molecule wherein the substituent is protected with a suitable protecting group, or conjugated peptides such as so-called glycopeptides having sugar chains; etc., as in the protein used in the present invention described above.

The partial peptide used in the present invention may also be used as an antigen for producing antibodies.

As salts of the protein or partial peptide used in the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein or partial peptide used in the present invention or salts thereof may be manufactured by publicly known methods used to purify a protein from human or warm-blooded animal cells or tissues described above. Alternatively, they may also be manufactured by culturing transformants containing DNAs encoding these proteins. Furthermore, they may also be manufactured by a modification of the methods for peptide synthesis, which will be later described.

Where these proteins are manufactured from human or mammalian tissues or cells, human or mammalian tissues or cells are homogenized, extracted with an acid or the like, and the extract is purified/isolated by a combination of chromatography techniques such as reverse phase chromatography, ion exchange chromatography, and the like.

To synthesize the protein or partial peptide used in the present invention or its salts, or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which $\alpha$-amino groups and functional groups on the side chains are appropriately protected, are condensed on the resin in accordance with the sequence of the objective protein according to various condensation methods publicly known in the art. At the end of the reaction, the protein or partial peptide is excised from the resin and at the same time, the protecting groups are removed. Then, intramolecular disulfide bond-forming reaction is performed in a highly diluted solution to obtain the objective protein or partial peptide, or amides thereof.

For condensation of the protected amino acids described above, a variety of activation reagents for protein synthesis may be used, and carbodiimides are particularly employed. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be appropriately chosen from solvents that are known to be usable for protein condensation reactions. Examples of such solvents are acid amides such as N, N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to avoid any possible effect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphiniothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, Cl2-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the desired protein or partial peptide, for example, the α-carboxyl group of the carboxy terminal amino acid is first protected by amidation; the peptide (protein) chain is then extended from the amino group side to a desired length. Then, a protein or partial peptide, in which only the protecting group of the N-terminal α-amino group of the peptide chain has been eliminated, and a protein or partial peptide, in which only the protecting group of the C-terminal carboxyl group has been eliminated, are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the esterified protein or peptide, for example, the α-carboxyl group of the carboxy terminal amino acid is condensed with a desired alcohol to prepare the amino acid ester, which is followed by procedures similar to the preparation of the amidated protein or peptide above to give the desired esterified protein or peptide.

The partial peptide used in the present invention or salts thereof can be manufactured by publicly known methods for peptide synthesis, or by cleaving the protein used in the present invention with an appropriate peptidase. The methods for peptide synthesis include, for example, either solid phase synthesis or liquid phase synthesis may be used. That is, the partial peptide or amino acids that can construct the partial peptide used in the present invention are condensed with the remaining part. Where the product contains protecting groups, these protecting groups are removed to give the desired peptide. Publicly known methods for condensation and elimination of the protecting groups are described in (i) to (v) below.

(i) M. Bodanszky & M. A. Ondetti: Peptide Synthesis, Interscience Publishers, New York (1966)
(ii) Schroeder & Luebke: The Peptide, Academic Press, New York (1965)
(iii) Nobuo Izumiya, et al.: Peptide Gosei-no-Kiso to Jikken (Basics and experiments of peptide synthesis), published by Maruzen Co. (1975)
(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)
(v) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide used in the present invention. When the partial peptide obtained by the above methods is in a free form, the partial peptide can be converted into an appropriate salt by a publicly known method or its modification; when the partial peptide is obtained in a salt form, it can be converted into a free form or other different salt form by a publicly known method or its modification.

The polynucleotide encoding the protein used in the present invention may be any polynucleotide so long as it contains the base sequence encoding the protein used in the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the protein used in the present invention may be any one of, for example, a DNA comprising the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65, or a DNA comprising a base sequence hybridizable to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 under high stringent conditions and encoding a protein which has the properties of substantially the same nature as those of the protein having the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66 described above.

Specific examples of the DNA that is hybridizable to the base sequence represented by SEQ ID NO: 1, SEQ ID NO: 3, SEQ ID NO: 5, SEQ ID NO 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 under high stringent conditions include DNAs comprising at least about 50% homology, preferably at least about 60% homology, more preferably at least about 70% homology, much more preferably at least about 80% homology, further much more preferably at least about 90% homology and most preferably at least about 95% homology, to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65; and the like.

Homology in the base sequence can be measured under the following conditions (an expectation value=10; gaps are allowed; filtering=ON; match score=1; mismatch score=−3) using the homology scoring algorithm NCBI BLAST (National Center for Biotechnology Information Basic Local Alignment Search Tool).

The hybridization can be carried out by publicly known methods or by modifications thereof, for example, by the method described in Molecular Cloning, 2nd (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, a DNA comprising the base sequence represented by SEQ ID NO: 1, etc. are used as the DNA encoding the protein comprising the amino acid sequence represented by SEQ ID NO: 2; a DNA comprising the base sequence represented by SEQ ID NO: 3, etc. are used as the DNA encoding the protein comprising the amino acid sequence represented by SEQ ID NO: 4; a DNA comprising the base sequence represented by SEQ ID NO: 5, etc. are used as the DNA encoding the protein comprising the amino acid sequence represented by SEQ ID NO: 6; a DNA comprising the base sequence represented by SEQ ID NO: 7, etc. are used as the DNA encoding the protein comprising the amino acid sequence represented by SEQ ID NO: 8; a DNA comprising the base sequence represented by SEQ ID NO: 9, etc. are used as the DNA encoding the protein comprising the amino acid sequence represented by SEQ ID NO: 10; a DNA comprising the base sequence represented by SEQ ID NO: 11, etc. are used as the DNA encoding the protein comprising the amino acid sequence represented by SEQ ID NO: 12; a DNA comprising the base sequence represented by SEQ ID NO: 13, etc. are used as the DNA encoding the protein comprising the amino acid sequence represented by SEQ ID NO: 14; a DNA comprising the base sequence represented by SEQ ID NO: 15, etc. are used as the DNA encoding the protein comprising the amino acid sequence represented by SEQ ID NO: 16; a DNA comprising the base sequence represented by SEQ ID NO: 17, etc. are used as the DNA encoding the protein comprising the amino acid sequence represented by SEQ ID NO: 18; a DNA comprising the base sequence represented by SEQ ID NO: 19, etc. are used as the DNA encoding the protein comprising the amino acid sequence represented by SEQ ID NO: 20; a DNA comprising the base sequence represented by SEQ ID NO: 21, etc. are used as the DNA encoding the protein comprising the amino acid sequence represented by SEQ ID NO: 22; a DNA comprising the base sequence represented by SEQ ID NO: 23, etc. are used as the DNA encoding the protein comprising the amino acid sequence represented by SEQ ID NO: 24; a DNA comprising the base sequence represented by SEQ ID NO: 25, etc. are used as the DNA encoding the protein comprising the amino acid sequence represented by SEQ ID NO: 26; a DNA comprising the base sequence represented by SEQ ID NO: 27, etc. are used as the DNA encoding the protein comprising the amino acid sequence represented by SEQ ID NO: 28; a DNA comprising the base sequence represented by SEQ ID NO: 29, etc. are used as the DNA encoding the protein comprising the amino acid sequence represented by SEQ ID NO: 30; a DNA comprising the base sequence represented by SEQ ID NO: 31, etc. are used as the DNA encoding the protein comprising the amino acid sequence represented by SEQ ID NO: 32; a DNA comprising the base sequence represented by SEQ ID NO: 33, etc. are used as the DNA encoding the protein comprising the amino acid sequence represented by SEQ ID NO: 34; a DNA comprising the base sequence represented by SEQ ID NO: 35, etc. are used as the DNA encoding the protein comprising the amino acid sequence represented by SEQ ID NO: 36; a DNA comprising the base sequence represented by SEQ ID NO: 37, etc. are used as the DNA encoding the protein comprising the amino acid sequence represented by SEQ ID NO: 38; a DNA comprising the base sequence represented by SEQ ID NO: 39, etc. are used as the DNA encoding the protein comprising the amino acid sequence represented by SEQ ID NO: 40; a DNA comprising the base sequence represented by SEQ ID NO: 41, etc. are used as the DNA encoding the protein comprising the amino acid sequence represented by SEQ ID NO: 42; a DNA comprising the base sequence represented by SEQ ID NO: 43, etc. are used as the DNA encoding the protein comprising the amino acid sequence represented by SEQ ID NO: 44; a DNA comprising the base sequence represented by SEQ ID NO: 45, etc. are used as the DNA encoding the protein comprising the amino acid sequence represented by SEQ ID NO: 46; a DNA comprising the base sequence represented by SEQ ID NO: 47, etc. are used as the DNA encoding the protein comprising the amino acid sequence represented by SEQ ID NO: 48; a DNA comprising the base sequence represented by SEQ ID NO: 49, etc. are used as the DNA encoding the protein comprising the amino acid sequence represented by SEQ ID NO: 50; a DNA comprising the base sequence represented by SEQ ID NO: 51, etc. are used as the DNA encoding the protein comprising the amino acid sequence represented by SEQ ID NO: 52; a DNA comprising the base sequence represented by SEQ ID NO: 53, etc. are used as the DNA encoding the protein comprising the amino acid sequence represented by SEQ ID NO: 54; a DNA comprising the base sequence represented by SEQ ID NO: 55, etc. are used as the DNA encoding the protein comprising the amino acid sequence represented by SEQ ID NO: 56; a DNA comprising the base sequence represented by SEQ ID NO: 57, etc. are used as the DNA encoding the protein comprising the amino acid sequence represented by SEQ ID NO: 58; a DNA comprising the base sequence represented by SEQ ID NO: 59, etc. are used as the DNA encoding the protein comprising the amino acid sequence represented by SEQ ID NO: 60; a DNA comprising the base sequence represented by SEQ ID NO: 61, etc. are used as the DNA encoding the protein comprising the amino acid sequence represented by SEQ ID NO: 62; a DNA comprising the base sequence represented by SEQ ID NO:

63, etc. are used as the DNA encoding the protein comprising the amino acid sequence represented by SEQ ID NO: 64; and a DNA comprising the base sequence represented by SEQ ID NO: 65, etc. are used as the DNA encoding the protein comprising the amino acid sequence represented by SEQ ID NO: 66.

The polynucleotide (eg. the DNA) encoding the partial peptide used in the present invention may be any DNA so long as it contains the base sequence encoding the partial peptide used in the present invention described above. The DNA may also be any of genomic DNA, genomic DNA library, cDNA derived from the cells and tissues described above, cDNA library derived from the cells and tissues described above and synthetic DNA.

As the DNA encoding the partial peptide used in the present invention, there are employed, for example, (i) a DNA comprising a part of the DNA having the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65, or (ii) a DNA comprising a base sequence hybridizable to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 under high stringent conditions and comprising a part of DNA encoding a protein having the activities of substantially the same nature as those of the protein of the present invention, and the like.

The DNA hybridizable to the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 indicates the same meaning as described above.

Methods for the hybridization and the high stringent conditions that can be used are the same as those described above.

For cloning of the DNA that completely encodes the protein or partial peptide used in the present invention (hereinafter sometimes merely referred to as the protein of the present invention in the description of cloning of DNAs encoding the protein and partial peptide and their expression), the DNA can be either amplified by PCR using synthetic DNA primers containing a part of the base sequence of the protein of the present invention, or the DNA inserted into an appropriate vector can be selected by hybridization with a labeled DNA fragment or synthetic DNA that encodes a part or entire region of the protein of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Substitution of the base sequence of DNA can be effected by publicly known methods such as the ODA-LA PCR method, the Gapped duplex method, the Kunkel method, etc., or its modification, using PCR, a publicly known kit available as Mutan™-super Express Km (manufactured by Takara Shuzo Co., Ltd.) or Mutan™-K (manufactured by Takara Shuzo Co., Ltd.), etc.

The cloned DNA encoding the protein can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the protein of the present invention can be manufactured, for example, by (a) excising the desired DNA fragment from the DNA encoding the protein of the present invention, and then (b) ligating the DNA fragment with an appropriate expression vector downstream a promoter in the vector.

Examples of the vector include plasmids derived form *Escherichia coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus *Escherichia*, preferred examples of the promoter include trp promoter, lac promoter, recA promoter, λPL promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Ampr), neomycin resistant gene (hereinafter sometimes abbreviated as Neor, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the protein of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the protein of the present invention thus constructed, transformants can be manufactured.

Examples of the host, which may be employed, are genus *Escherichia*, genus *Bacillus*, yeast, insect cells, insects, animal cells, etc.

Specific examples of the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the genus *Bacillus* include *Bacillus subtilis* MI14 [Gene, 24, 255 (1983)], 207-21 [Journal of Biochemistry, 95, 87 (1984)], etc.

Examples of yeast include *Saccharomyces cerevisiae* AH22, AH22R-, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr-) cell), mouse L cell, mouse AtT-20, mouse myeloma cell, mouse ATDC5 cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors containing the DNAs encoding the protein can be obtained.

Where the host is bacteria belonging to the genus *Escherichia* or the genus *Bacillus*, the transformant can be appropriately cultured in a liquid medium, which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature), 195, 788 (1962)) to which an appropriate additive such as immobilized 10% bovine serum is added. Preferably, pH of the medium is adjusted to about 6.2 to 6.4. Normally, the transformant is cultivated at about 27° C. for about 3 to 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30 to 40° C. for about 15 to 60 hours and, if necessary, the culture can be aerated or agitated.

As described above, the protein of the present invention can be produced in the cell of, in the cell membrane of, or outside of the transformant.

The protein of the present invention can be separated and purified from the culture described above by the following procedures.

When the protein of the present invention is extracted from the culture of bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc to produce crude extract of the protein. Thus, the crude extract of the protein can be obtained. The buffer used for the procedures may contain a protein modifier such as urea or guanidine hydrochloride, or a surfactant such as Triton X-100™, etc. When the protein of the present invention is secreted in the culture broth, the supernatant can be separated, after completion of the cultivation, from the bacteria or cell to collect the supernatant by a publicly known method.

The protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein thus obtained is in a free form, the protein can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein-modifying enzyme so that the protein can be subjected to addition of an appropriate modification or removal of a partial polypeptide. Examples of the protein-modifying enzyme include trypsin, chymotrypsin, arginyl endopeptidase, protein kinase, glycosidase and the like.

The presence of the thus produced protein of the present invention can be determined by an enzyme immunoassay or western blotting using a specific antibody.

The antibodies against the protein or partial peptide used in the present invention, or its salts may be any of polyclonal and monoclonal antibodies, as long as they are capable of recognizing the protein or partial peptide used in the present invention, or its salts.

The antibodies against the protein or partial peptide used in the present invention, or its salts (hereinafter they are sometimes collectively referred to as the protein of the present invention in the description of the antibodies) can be produced by a publicly known method of producing an antibody or antiserum, using the protein of the present invention as an antigen.

[Preparation of Monoclonal Antibody]

(a) Preparation of Monoclonal Antibody-Producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are simian, rabbits, canine, guinea pigs, mice, rats, ovine, goats and fowl, with the use of mice and rats being preferred.

In the preparation of monoclonal antibody-producing cells, a warm-blooded animal, e.g., mouse, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the protein as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally under 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (protein antigen) per se, or a complex of immunogen and a carrier protein is formed and the animal is immunized with the complex in a manner similar to the method described above for the manufacture of monoclonal antibodies. The product containing the antibody against the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described above.

The antisense polynucleotide having a complementary or substantially complementary base sequence to the base sequence of a polynucleotide encoding the protein or partial peptide used in the present invention (e.g., DNA (hereinafter these DNAs are sometimes collectively referred to as the DNA of the present invention in the description of antisense polynucleotide)) can be any antisense polynucleotide, so long as it possesses a base sequence complementary or substantially complementary to the base sequence of the DNA of the present invention and capable of suppressing the expression of said DNA, but antisense DNA is preferred.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention), and the like. Especially in the entire base sequence of the complementary strand to the DNA of the present invention, preferred are (a) an antisense polynucleotide having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon) in the case of antisense polynucleotide directed to translation inhibition and (b) an antisense polynucleotide having at least about 70% homology, preferably at least about 80% homology, more preferably at least about 90% homology and most preferably at least about 95% homology, to the complementary strand of the entire base sequence of the DNA of the present invention having intron, in the case of antisense polynucleotide directed to RNA degradation by RNaseH, respectively.

Specific examples include an antisense polynucleotide containing the entire or part of a base sequence complementary or substantially complementary to a base sequence of DNA containing the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65, preferably an antisense polynucleotide containing the entire or part of a base sequence complementary to a base sequence of DNA containing the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65 (more preferably, an antisense polynucleotide containing the entire or part of a base sequence complementary to a base sequence of DNA containing the base sequence represented by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, or SEQ ID NO: 65, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. Also, the sugar (deoxyribose) in each nucleotide may be replaced by a chemically modified structure such as 2'-O-methylation, etc. The base part (pyrimidine, purine) may also be chemically modified and may be any one which hybridizes to a DNA containing the base sequence represented by SEQ ID NO: 2. These antisense polynucleotides may be synthesized using a publicly known DNA synthesizer, etc.

According to the present invention, the antisense polynucleotide capable of inhibiting the replication or expression of a gene for the protein of the present invention can be designed and synthesized based on the base sequence information of cloned or identified protein-encoding DNA. Such a nucleotide (a nucleic acid) is hybridizable to RNA of a gene for the protein of the present invention to inhibit the synthesis or function of said RNA or is capable of modulating and/or controlling the expression of a gene for the protein of the present invention via interaction with RNA associated with the protein of the present invention. Polynucleotides complementary to the selected sequences of RNA associated with the protein of the present invention and polynucleotides specifically hybridizable to RNA associated with the protein of the present invention are useful in modulating and/or controlling the in vivo and in vitro expression of the protein gene of the present invention, and are useful for the treatment or diagnosis of diseases, etc. The term “corresponding” is used to mean homologous to or complementary to a particular sequence of the nucleotide including the gene, base sequence or nucleic acid. The term “corresponding” between nucleotides, base sequences or nucleic acids and proteins usually refer to amino acids of a protein under the order derived from the sequence of nucleotides (nucleic acids) or their complements. In the protein genes, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target, or the relationship between the target and the polynucleotides hybridizable with the target, can be denoted to be “antisense”. Examples of the antisense polynucleotides include polynucleotides containing 2-deoxy-D-ribose, polynucleotides containing D-ribose, any other type of polynucleotides which are N-glycosides of a purine or pyrimidine base, or other polymers having non-nucleotide backbones (e.g., commercially available protein nucleic acids and synthetic sequence-specific nucleic acid polymers) or other polymers containing particular linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms “nucleoside”, “nucleotide” and “nucleic acid” are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide of the present invention is RNA, DNA or a modified nucleic acid (RNA, DNA). Specific examples of the modified nucleic acid are sulfur and thiophosphate derivatives of nucleic acids, those resistant to degradation of polynucleoside amides or oligonucleoside amides, etc. The antisense nucleic acid of the present invention can be modified preferably based on the following design. The antisense nucleic acide of the present invention can be modified preferably based on the following design, that is, by increasing the intracellular stability of the antisense polynucleotide, enhancing the cell permeability of the antisense polynucleotide, increasing the affinity of the polynucleotide to the targeted sense strand to a higher level, or minimizing the toxicity, if any, of the antisense nucleic acide.

Many of such modifications are known and disclosed in, for example, Pharm. Tech. Japan, Vol. 8, p. 247 or 395, 1992, Antisense Research and Applications, CRC Press, 1993, etc.

The antisense nucleic acide of the present invention may contain altered or modified sugars, bases or linkages. The antisense nucleic acide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory activity of the antisense nucleic acide can be examined using the transformant of the present invention, the gene expression system of the present invention in vivo and in vitro, or the translation system for the protein of the present invention in vivo and in vitro. The nucleic acid can be applied to cells by various methods known per se.

Hereinafter, the protein of the present invention, its partial peptides, or salts thereof (hereinafter sometimes merely referred to as the protein of the present invention), the polynucleotide (e.g., DNA) (hereinafter sometimes merely referred to as the DNA of the present invention) encoding the protein of the present invention or its partial peptides, the antibodies against the protein of the present invention, its partial peptides, or salts thereof (hereinafter sometimes referred to as the antibodies of the present invention) and the antisense polynucleotides to the polynucleotide (e.g., DNA) of the present invention (hereinafter sometimes merely referred to as the antisense polynucleotides of the present invention) are specifically described for their applications.

The protein comprising an amino acid sequence identical or substantially identical with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 or SEQ ID NO: 62, or its partial peptide or a salt thereof is sometimes referred to "protein A of the present invention".

The protein comprising an amino acid sequence identical or substantially identical with the amino acid sequence represented by SEQ ID NO: 64 or SEQ ID NO: 66, or its partial peptide or a salt thereof is sometimes referred to "protein B of the present invention".

(1) Screening of Pharmaceutical Candidate Compounds for Disease

The protein A of the present invention is increasingly expressed in the lung as chronic obstructive pulmonary disease proceeds, and thus the compound or its salt that inhibits the activity of the protein A of the present invention can be used as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

The protein A of the present invention is useful as a reagent for screening the compound or its salt that regulates (preferably inhibits) the activity of the protein A of the present invention.

The compound or its salt that regulates (preferably inhibits) the activity of the protein A of the present invention is screened by measuring and comparing the activity of the protein A of the present invention in the case (i) where a cell having an ability to produce the protein A of the present invention is cultured and in the case (ii) a cell having an ability to produce the protein A of the present invention is cultured in the presence of a test compound.

As the cell having an ability to produce the protein A of the present invention, for example, a host (transformant) transformed with a vector containing the DNA encoding the protein of the present invention is used. Preferably, animal cells such as COS7 cells, CHO cells, HEK293 cells, etc. are used as the host. In the screening, it is preferable to use the transformant in which the protein A of the present invention has been expressed on the cell membrane or in the cells, e.g., by culturing through the procedures described above. The procedures for culturing the cells capable of expressing the protein A of the present invention are similar to the culturing procedures for the transformant of the present invention described above.

Examples of the test compound include peptides, proteins, antibodies, non-peptide compounds, synthetic compounds, fermentation products, cell extracts, plant extracts, animal tissue extracts, blood plasma etc.

For example, a test compound that decreases the activity of the protein A of the present invention in (ii) above by about at least 20%, preferably at least 30%, more preferably about at least 50% as compared with the activity in (i) above can be selected as a compound that inhibits the activity of the protein A of the present invention, while a test compound that increases the activity of the protein A of the present invention in (ii) above by about at least 20%, preferably at least 30%, more preferably about at least 50% as compared with the activity in (i) above can be selected as a compound that promotes the activity of the protein A of the present invention.

Hereinafter, the case where the protein A of the present invention is a protein comprising an amino acid sequence identical or substantially identical with the amino acid sequence represented by SEQ ID NO: 2, or its partial peptide or a salt thereof (abbreviated as protein A1 of the present invention) is described.

The protein A1 of the present invention produces 25-hydroxycholesterol from cholesterol in alveolar macrophage, and the 25-hydroxycholesterol promotes production of inflammatory cytokines (for example, CXCL2 and IL-1β) thereby accelerating neutrophil infiltration in the airway and advancing the morbid state of chronic obstructive pulmonary disease. Accordingly, the compound or its salt that inhibits the activity of the protein A1 of the present invention can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

Specifically, the screening method using the protein A1 of the present invention includes a method of screening the compound or its salt that regulates (preferably inhibits) the activity of the protein A1 of the present invention, which comprises comparing (ia) the cholesterol hydroxylation activity of (the cell having an ability to produce) the protein A1 of the present invention, with (iia) the cholesterol hydroxylation activity of (the cell having an ability to produce) the protein A1 of the present invention in the presence of a test compound.

The cholesterol hydroxylation activity can be assayed by methods known per se, for example, a method described in J. Biol. Chem. 273:34316-34327 (1998) or with its modifications.

Specifically, the compound or its salt that regulates (preferably inhibits) the activity of the protein A1 of the present invention is screened by measuring the cholesterol hydroxylation activity in the case (ib) where the protein A1 of the present invention is reacted with a labeled cholesterol and in the case (iib) where the protein A1 of the present invention is reacted with a labeled cholesterol, in the presence of a test compound. This reaction is carried out in a suitable buffer. The cholesterol hydroxylation activity is determined by separating the product from the substrate by thin layer chromatography and then measuring the amount of the product (for example, radioactivity etc.). Measurement of the radioactivity is carried out according to a known method using a scintillation counter etc.

The protein A1 produced by culturing cells having an ability to produce the protein A1 of the present invention, cells having an ability to produce the protein A1 of the present invention, etc., are used as the protein A1 of the present invention. For example, the protein A1 expressed by cells obtained by inserting the base sequence represented by SEQ ID NO: 1 into a (commercial) expression vector for animal cell and then introducing it into animal cells (for example, COS cells), or cells obtained by inserting the base sequence represented by SEQ ID NO: 1 into an expression vector for animal cell and then introducing it into animal cells (for example, COS cells), etc., can be used.

The labeling agent used includes, radioisotopes (for example, [$^{125}$I], [$^{131}$I], [$^{3}$H], [$^{14}$C], [$^{32}$P], [$^{33}$P], [$^{35}$S], etc.), fluorescent substances [for example, cyanine fluorescent dyes (e.g., Cy2, Cy3, Cy5, Cy5.5, Cy7 (manufactured by Amersham Biosciences Corp.), etc.), fluorescamine, fluorescein isothiocyanate, NBD (7-nitrobenz-2-oxa-1,3-diazol), BODIPY (boron-dipyrromethene) etc.], enzymes (for example, β-galactosidase, β-glucosidase, alkaline phosphatase, peroxidase, malate dehydrogenase etc), luminescent substances (for example, luminol, a luminol derivative, luciferin, lucigenin etc.), biotin, and lanthanide elements.

The screening method wherein a protein comprising an amino acid sequence identical or substantially identical with the amino acid sequence represented by SEQ ID NO: 30, or a partial peptide or its salt (abbreviated as protein A2 of the present invention) is used, for example, as the protein A of the present invention is described below, Specific examples includes a method of screening the compound or its salt that regulates (preferably inhibits) the activity of the protein A2 of the present invention, which comprises comparing (ic) the proteolysis activity of the protein A2 of the present invention, with (iic) the proteolysis activity of the protein A2 of the present invention in the presence of a test compound.

The proteolysis hydrolysis activity can be assayed by methods known per se, for example, a method described in J. Biol. Chem. 272:4281-4286 (1997) or with its modifications.

Specifically, the compound or its salt that regulates (preferably inhibits) the activity of the protein A2 of the present invention is screened by measuring the proteolysis activity in the case (id) where the protein A2 of the present invention is reacted with a labeled substrate peptide and in the case (iid) where the protein A2 of the presence is reacted with a substrate peptide in the presence of a test compound. This reaction is carried out in a suitable buffer. By measuring the amount of the substrate peptide decomposed (for example, fluorescence intensity), the proteolysis activity is measured. As the labeled substrate peptide, use is made of, for example, a substrate peptide (for example, Nma-Pro-Lys-Pro-Leu-Ala-Nva-Trp-Lys (Dnp)-$NH_2$ (SEQ ID NO: 74), Nma: N-methyl anthranilic acid etc.) labeled with a fluorescent substance (for example, fluorescamine, fluorescein isocyanate etc.). The fluorescence intensity is measured according to methods known in the art, for example a method using a fluorescence measuring apparatus.

As the protein A2 of the present invention, use is made of the one produced by culturing cells having an ability to produce the protein A2 of the present invention. For example, the base represented by SEQ ID NO: 29 is introduced into a commercial expression vector for prokaryotic cell, then introduced into a prokaryotic cell (for example, *Escherichia coli*), then expressed and re-folded to give the protein having the activity.

The protein B of the present invention is decreasingly expressed in the lung as chronic obstructive pulmonary disease proceeds, and thus the compound or its salt that promotes the activity of the protein B of the present invention can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

The protein B of the present invention is useful as a reagent for screening the compound or its salt that regulates (preferably promotes) the activity of the protein B of the present invention.

The compound or its salt that regulates (preferably promotes) the activity of the protein B of the present invention is screened by measuring and comparing the activity of the protein B of the present invention in the case (i') where a cell having an ability to produce the protein B of the present invention is cultured and in the case (ii') where a cell having an ability to produce the protein B of the present invention is cultured in the presence of a test compound.

As the cell having an ability to produce the protein B of the present invention, for example, a host (transformant) transformed with a vector containing the DNA encoding the protein of the present invention is used. Preferably, animal cells such as COS7 cells, CHO cells, HEK293 cells, etc. are used as the host. In the screening, it is preferable to use the transformant in which the protein B of the present invention has been expressed on the cell membrane or in the cells, e.g., by culturing it through the procedures described above. The procedures for culturing the cells capable of expressing the protein B of the present invention are similar to the culturing procedures for the transformant of the present invention described above.

Examples of the test compound include peptides, proteins, antibodies, non-peptide compounds, synthetic compounds, fermentation products, cell extracts, plant extracts, animal tissue extracts, blood plasma etc.

For example, a test compound that increases the activity of the protein B of the present invention in (ii') above by about at least 20%, preferably at least 30%, more preferably about at least 50% as compared with the activity in (i') above can be selected as a compound that promotes the activity of the protein B of the present invention, while a test compound that decreases the activity of the protein B of the present invention in (ii') above by about at least 20%, preferably at least 30%, more preferably about at least 50% as compared with the activity in (i') above can be selected as a compound that inhibits the activity of the protein B of the present invention.

The gene encoding the protein A of the present invention is increasingly expressed in the lung as chronic obstructive pulmonary disease proceeds, and thus the compound or its salt that inhibits the expression of the gene encoding the protein A of the present invention can be used as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

The protein A1 of the present invention produces 25-hydroxycholesterol from cholesterol in alveolar macrophage, and the 25-hydroxycholesterol promotes production of inflammatory cytokines (for example, CXCL2 and IL-1β) thereby accelerating neutrophil infiltration in the airway and advancing the morbid state of chronic obstructive pulmonary disease. Accordingly, the compound or its salt that inhibits the expression of the gene encoding the protein A1 of the present invention can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

The gene encoding the protein B of the present invention is decreasingly expressed in the lung as chronic obstructive pulmonary disease proceeds, and thus the compound or its salt that regulates (preferably promotes) the expression of the gene encoding the protein B of the present invention can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

Therefore, the polynucleotide (for example, DNA) of the present invention is useful as a reagent for:

(a) screening the compound or its salt that regulates (preferably inhibits) the expression of the gene encoding the protein A of the present invention, or (b) screening the compound or its salt that regulates (preferably promotes) the expression of the gene encoding the protein B of the present invention.

The screening method includes a method which comprises measuring and comparing the expression level of the gene (for example, the amount of the protein of the present invention or the amount of mRNA encoding the protein) in the case (iii) where cells having an ability to produce the protein of the present invention are cultured, with that in the case (iv) where cells having an ability to produce the protein of the present invention are cultured in the presence of a test compound.

The test compound and the cells having an ability to produce the protein of the present invention include those described above.

In measuring the amount of the protein, the protein present in a cellular extract or the like can be measured according to known methods, for example by Western analysis, ELISA or the like, or a modification thereof, with antibodies recognizing the protein of the present invention.

The amount of mRNA can be measured according to known methods, for example by Northern hybridization using, as a probe, SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63 or SEQ ID NO: 65 or a nucleic acid comprising a part thereof, or by Northern hybridization using, as a primer, SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63 or SEQ ID NO: 65 or a nucleic acid comprising a part thereof, or by the PCR method using, as a primer, SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63 or SEQ ID NO: 65 or a nucleic acid comprising a part thereof, or by a modification thereof.

For example, when a test compound increases the expression level of the gene in the case (iv) described above by at least about 20%, preferably at least 30% and more preferably at least about 50%, as compared to the case (iii) above, the test compound can be selected to be a compound promoting the expression of the gene encoding the protein of the present invention; when a test compound inhibits the expression level of the gene in the case (iv) described above by at least about 20%, preferably at least 30% and more preferably at least about 50%, as compared to the case (iii) above, the test compound can be selected to be a compound suppressing the expression of the gene encoding the protein of the present invention.

The screening kit of the present invention comprises the protein used in the present invention, the cell having an ability to produce the protein used in the present invention, the polynucleotide encoding the protein, or the like.

The compounds or salts thereof, which are obtainable using the screening method or screening kit of the present invention, are compounds (or salts thereof) selected from the above-mentioned test compounds, for example, peptides, proteins, antibodies, non-peptide compounds, synthetic compounds, fermentation products, cell extracts, plant extracts, animal tissue extracts, blood plasma, and the like, and these compounds or salts thereof are compounds or their salts regulating the activity (for example, scavenger receptor activity) of the protein of the present invention.

As the salts of the compounds, the same salts as those of the protein of the present invention can be used.

The compound or its salt that regulates (preferably inhibits) the activity of the protein A of the present invention, the compound or its salt that regulates (preferably inhibits) the expression of the gene encoding the protein A of the present invention, the compound or its salt that regulates (preferably promotes) the activity of the protein B of the present invention, and the compound or its salt that regulates (preferably promotes) the expression of the gene encoding the protein B of the present invention are low toxic and can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

Where the compound or its salts obtained by using the screening method or screening kit of the present invention are used as the prophylactic/therapeutic agents described above, these compounds can be converted into pharmaceutical preparations in a conventional manner.

For example, the composition for oral administration includes solid or liquid preparations, specifically tablets (including dragees and film-coated tablets), pills, granules, powdery preparations, capsules (including soft capsules), syrup, emulsions, suspensions, etc. Such a composition is manufactured by publicly known methods and contains a carrier, a diluent or excipient conventionally used in the field of pharmaceutical preparations. Examples of the carrier or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous and intramuscular injections, drip infusions, intraarticular injection, etc. These injectable preparations may be prepared by methods publicly known. For example, the injectable preparations may be prepared by dissolving, suspending or emulsifying the antibody or its salt described above in a sterile aqueous medium or an oily medium conventionally used for injections. As the aqueous medium for injections, there are for example physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed e.g., sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 5 to 500 mg per dosage unit form; it is preferred that the aforesaid antibody is contained in about 5 to about 100 mg especially in the form of injection, and in 10 to 250 mg for the other forms.

Each composition described above may further contain other active components unless formulation causes any adverse interaction with the compound described above.

Since the pharmaceutical preparations thus obtained are safe and low toxic, they can be administered to human or warm-blooded animal (e.g., mouse, rat, rabbit, sheep, swine, bovine, equine, fowl, feline, canine, simian, chimpanzee, etc.) orally or parenterally.

The dose of the compound or its salts may vary depending upon its action, target disease, subject to be administered, route of administration, etc. For example, when the compound or its salt that inhibits the activity of the protein A of the present invention is orally administered for the purpose of treating pulmonary emphysema, the compound or its salt is generally administered to an adult (as 60 kg body weight) in a daily dose of about 0.1 to about 100 mg, preferably about 1.0 to about 50 mg and more preferably about 1.0 to about 20 mg. In parenteral administration, a single dose of the said compound or its salt may vary depending upon subject to be administered, target disease, etc. When the compound or its salt that inhibits the activity of the protein A of the present invention is administered to an adult (as 60 kg body weight) in the form of an injectable preparation for the purpose of treating pulmonary emphysema, for example, it is advantageous to administer the compound or its salt by way of intravenous injection in a daily dose of about 0.01 to about 30 mg, preferably about 0.1 to about 20 mg, and more preferably about 0.1 to about 10 mg. For other animal species, the corresponding dose as converted per 60 kg weight can be administered.

(2) Quantification for the Protein of the Present Invention, its Partial Peptide or Salts Thereof The antibody against the protein of the present invention (hereinafter sometimes merely referred to as the antibody of the present invention) is capable of specifically recognizing the protein of the present invention, and thus can be used for quantification of the protein of the present invention in a test sample fluid, in particular, for quantification by sandwich immunoassay; etc.

That is, the present invention provides:

(i) a method of quantifying the protein of the present invention in a test sample fluid, which comprises competitively reacting the antibody of the present invention, a test sample fluid and a labeled form of the protein of the present invention, and measuring the ratio of the labeled form of the protein of the present invention bound to said antibody; and, (ii) a method of quantifying the protein of the present invention in a test sample fluid, which comprises reacting a test sample fluid simultaneously or continuously with the antibody of the present invention immobilized on a carrier and another labeled antibody of the present invention, and then measuring the activity of the labeling agent on the insoluble carrier.

In the quantification method (ii) described above, it is preferred that one antibody is capable of recognizing the N-terminal region of the protein of the present invention, while another antibody is capable of reacting with the C-terminal region of the protein of the present invention.

The monoclonal antibody against the protein of the present invention (hereinafter sometimes referred to as the monoclonal antibody of the present invention) can be used to quantify the protein of the present invention. In addition, the protein can be detected by means of a tissue staining as well. For these purposes, the antibody molecule per se may be used or $F(ab')_2$, Fab' or Fab fractions of the antibody molecule may also be used.

The method of quantifying the protein of the present invention using the antibody of the present invention is not particularly limited. Any quantification method can be used, so long as the amount of antibody, antigen or antibody-antigen complex corresponding to the amount of antigen (e.g., the amount of the protein) in a test sample fluid can be detected by chemical or physical means and the amount of the antigen can be calculated from a standard curve prepared from standard solutions containing known amounts of the antigen. For such an assay method, for example, nephrometry, the competitive method, the immunometric method, the sandwich method, etc. are suitably used and in terms of sensitivity and specificity, it is particularly preferred to use the sandwich method described hereinafter.

Examples of the labeling agent used in the assay method using the labeling substance are radioisotopes, enzymes, fluorescent substances, luminescent substances, lanthanide, and the like. As the radioisotopes, there are used, e.g., [$^{125}$I], [$^{131}$I], [$^{3}$H], [$^{14}$C], etc. The enzymes described above are preferably enzymes, which are stable and have a high specific activity, and include, e.g., β-galactosidase, β-glucosidase, an alkaline phosphatase, a peroxidase, malate dehydrogenase, etc. As the fluorescent substances, there are used, e.g., fluorescamine, fluorescein isothiocyanate, etc. As the luminescent substances described above there are used, e.g., luminol, a luminol derivative, luciferin, lucigenin, etc. Furthermore, the biotin-avidin system may be used as well for binding of an antibody or antigen to a labeling agent.

For immobilization of the antigen or antibody, physical adsorption may be used. Chemical binding techniques conventionally used for insolubilization or immobilization of proteins, enzymes, etc. may also be used. For carriers, there are used, e.g., insoluble polysaccharides such as agarose, dextran, cellulose, etc.; synthetic resin such as polystyrene, polyacrylamide, silicon, etc., and glass or the like.

In the sandwich method, the immobilized monoclonal antibody of the present invention is reacted with a test fluid (primary reaction), then with a labeled form of another monoclonal antibody of the present invention (secondary reaction), and the activity of the label on the immobilizing carrier is measured, whereby the amount of the protein of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the protein of the present invention by the sandwich method of the present invention, antibodies that bind to different sites of the protein of the present invention are preferably used as the monoclonal antibodies of the present invention used for the primary and secondary reactions. That is, in the antibodies used for the primary and secondary reactions are, for example, when the antibody used in the secondary reaction recognizes the C-terminal region of the protein of the present invention, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, the competitive method, the immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody against the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody against the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying each of these immunological methods to the quantification method of the present invention, any particular conditions or procedures are not required. Quantification system for the protein of the present invention or its salts is constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the protein of the present invention can be quantified with high sensitivity, using the antibody of the present invention.

Furthermore, when an increased or decreased level of the protein of the present invention is detected by quantifying the concentration of the protein of the present invention using the antibody of the present invention, it can be diagnosed that one suffers from, for example, respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.]; or it is highly likely to suffer from these disease in the future.

In addition, the antibody of the present invention can be used to detect the protein of the present invention, which is present in a test sample such as a body fluid, a tissue, etc. The antibody can also be used to prepare an antibody column for purification of the protein of the present invention, detect the protein of the present invention in each fraction upon purification, analyze the behavior of the protein of the present invention in the cells under investigation; etc.

(3) Gene Diagnostic Agent

By using the DNA of the present invention, e.g., as a probe, the DNA can detect an abnormality (gene abnormality) of the DNA or mRNA encoding the protein of the present invention or its partial peptide in human or warm-blooded animal (e.g., rat, mouse, guinea pig, rabbit, fowl, ovine, swine, bovine, equine, feline, canine, simian, chimpanzee, etc.). Therefore, the DNA of the present invention is useful as a gene diagnostic agent for detecting damages to the DNA or mRNA, its mutation, or decreased expression, increased expression, over expression, etc. of the DNA or mRNA, and so on.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When over expression or decreased expression is detected by, e.g., Northern hybridization or DNA mutation is detected by the PCR-SSCP assay, it can be diagnosed that it is highly likely to suffer from, for example, respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

(4) Pharmaceutical Preparation Comprising the Antisense Polynucleotide

The antisense polynucleotide of the present invention that binds complementarily to the polynucleotide (for example, DNA) encoding the protein A of the present invention to inhibit expression of the DNA is low-toxic and can suppress the functions and activity of the protein A or DNA encoding the protein in the body, and can thus be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably a prophylactic/therapeutic agent for chronic obstructive pulmonary disease etc.

Where the antisense polynucleotide described above is used as the aforesaid prophylactic/therapeutic agent, it can be prepared into pharmaceutical preparations by publicly known methods, which are provided for administration.

For example, when the antisense polynucleotide described above is used, the antisense polynucleotide alone is administered directly, or the antisense polynucleotide is inserted into an appropriate vector such as retrovirus vector, adenovirus vector, adenovirus-associated virus vector, etc., followed by treating in a conventional manner. The antisense polynucleotide may then be administered orally or parenterally to human or mammal (e.g., rat, rabbit, ovine, swine, bovine, feline, canine, simian, etc.) in a conventional manner. The antisense polynucleotide may also be administered as it stands, or may be prepared in pharmaceutical preparations together with a physiologically acceptable carrier to assist its uptake, which are then administered by gene gun or through a catheter such as a catheter with a hydrogel. Alternatively, the antisense polynucleotide may be prepared into an aerosol, which is topically administered into the trachea as an inhaler.

Further for the purposes of improving pharmacokinetics, extending a half-life and improving intracellular uptake efficiency, the antisense polynucleotide described above is prepared into pharmaceutical preparations (injectable preparations) alone or together with a carrier such as liposome, etc. and the preparations may be administered intravenously, subcutaneously, in airway or at the pulmonary regions, etc.

A dose of the antisense polynucleotide may vary depending on target disease, subject to be administered, route for administration, etc. For example, where the antisense polynucleotide of the present invention is administered for the purpose of treating pulmonary emphysema, the antisense polynucleotide is generally administered to an adult (60 kg body weight) in a daily dose of about 0.1 to 100 mg.

Similar to the antisense polynucleotide, the double-stranded RNA (for example, siRNA (small (short) interfering RNA) or shRNA (small (short) hairpin RNA to the polynucleotide encoding the protein A of the present invention) comprising a part of RNA encoding the protein A of the present invention, and the ribozyme comprising a part of RNA encoding the protein A of the present invention, can inhibit the expression of the gene encoding the protein, and can suppress the functions of the protein A or DNA encoding the protein in the body, and can thus be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably a prophylactic/therapeutic agent for chronic obstructive pulmonary disease etc.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the protein of the present invention. A part of the RNA encoding the protein of the present invention includes a portion proximal to a cleavage site on the RNA of the present invention, which may be cleaved by a publicly known ribozyme (RNA fragment). Where the double-stranded RNA or the ribozyme described above can be used for example as a prophylactic/therapeutic agent, it can be prepared into pharmaceutical preparations similar to the antisense polynucleotide, which are provided for administration.

(5) Pharmaceutical Preparation Comprising the Antibody of the Present Invention

The antibody of the present invention can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably a prophylactic/therapeutic agent for chronic obstructive pulmonary disease etc.

The antibody of the present invention can be administered directly or as a pharmaceutical composition of appropriate dosage form. The pharmaceutical composition used for the administration comprises the antibody described above or its salt, pharmaceutically acceptable carriers, dilutes or excipients. Such a composition is provided as a dosage form appropriate for oral or parenteral administration.

For example, the composition for oral administration includes solid or liquid preparations, specifically tablets (including dragees and film-coated tablets), pills, granules, powdery preparations, capsules (including soft capsules), syrup, emulsions, suspensions, etc. Such a composition is manufactured by publicly known methods and contains a carrier, a diluent or excipient conventionally used in the field of pharmaceutical preparations. Examples of the carrier or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous, intramuscular injections, drip infusions, etc.

These injectable preparations may be prepared by methods publicly known. For example, the injectable preparations may be prepared by dissolving, suspending or emulsifying the antibody or its salt described above in a sterile aqueous medium or an oily medium conventionally used for injections. As the aqueous medium for injections, there are for example physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed e.g. sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 5 to 500 mg per dosage unit form; it is preferred that the aforesaid antibody is contained in about 5 to about 100 mg especially in the form of injection, and in 10 to 250 mg for the other forms.

Each composition described above may further contain other active components unless formulation causes any adverse interaction with the compound described above.

The prophylactic/therapeutic agent comprising the antibody of the present invention for the diseases described above is low toxic and can be administered to human or mammals (e.g., rats, rabbits, ovine, swine, bovine, feline, canine, simian, etc.) orally or parenterally (e.g., intravenously) in the form of liquid preparation as it is or as a pharmaceutical composition of appropriate dosage form. The dose may vary depending upon subject to be administered, target disease, conditions, route of administration, etc. For example, when the agent is used for the purpose of treating, e.g., breast cancer in an adult, it is advantageous to administer the antibody of the present invention normally in a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the agent can be administered in a dose corresponding to the dose given above. When the condition is especially severe, the dose may be increased according to the condition.

The antibody of the present invention is also useful for example as a diagnostic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

(6) Prophylactic/Therapeutic Agent for Diseases in which the Protein of the Present Invention is Involved The protein B of the present invention is decreasingly expressed in the lung as chronic obstructive pulmonary disease proceeds. When the protein B of the present invention or the polynucleotide encoding the same is abnormal or deficient, it is highly likely to suffer from respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.]. Accordingly, the protein B of the present invention or the polynucleotide encoding the same can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

For example, when there is a patient showing a decrease or deficiency in the protein B of the present invention or the polynucleotide encoding the same in the living body, (A) the polynucleotide is administered into the patient to express the protein B of the invention in the living body, (B) the polynucleotide is inserted into cells to express the protein B of the invention and the cells are transplanted to the patient, or (C) the protein B of the invention is administered into the patient, whereby the role of the protein B of the invention can be exhibited sufficiently or normally in the patient.

Where the polynucleotide (for example, DNA) described above is used as the prophylactic/therapeutic agents described above, the DNA itself is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA, or prepared into medicines together with physiologically acceptable carriers such as adjuvants to assist its uptake, which are administered by gene gun or through a catheter such as a hydrogel catheter.

Where the protein B of the present invention is used as the aforesaid prophylactic/therapeutic agents, the protein is advantageously used on a purified level of at least 90%, preferably at least 95%, more preferably at least 98% and most preferably at least 99%.

The protein B of the present invention can be used orally, for example, in the form of tablets which may be sugar coated if necessary and desired, capsules, elixirs, microcapsules etc., or parenterally (preferably subcutaneously) in the form of injectable preparations such as a sterile solution and a suspension in water or with other pharmaceutically acceptable liquid. For example, these preparations can be manufactured by mixing the protein B of the present invention with a physiologically acceptable known carrier, a flavoring agent, an excipient, a vehicle, an antiseptic agent, a stabilizer, a binder, etc. in a unit dosage form required in a generally accepted manner that is applied to making medicines. The active ingredient in the preparation is controlled in such a dose that an appropriate dose is obtained within the specified range given.

A vector into which the polypeptide (for example, DNA) was inserted can be prepared into a pharmaceutical preparation in a conventional manner and used usually parenterally.

Since the pharmaceutical preparation thus obtained is safe and low toxic, it can be administered to human or mammal (e.g., rat, mouse, guinea pig, rabbit, bird, ovine, swine, bovine, equine, feline, canine, simian, etc.).

The dose of the protein B of the present invention may vary depending upon target disease, subject to be administered, route of administration, etc. For example, when the protein B of the present invention is parenterally administered for the purpose of treating pulmonary emphysema, it can be administered to the adult patient (as 60 kg body weight) generally in a dose of about 0.1 to 100 mg, preferably about 1.0 to 50 mg and more preferably about 1.0 to 20 mg. For other animal species, the corresponding dose as converted per 60 kg weight can be administered.

(7) With Respect to "Prophylactic/Therapeutic Agent for Respiratory Diseases Comprising the Compound or its Salt that has an Action of Regulating the Cholesterol Hydroxylation Activity"

The "compound having the action of regulating the cholesterol hydroxylation activity may be any compounds having the action of regulating the cholesterol hydroxylation activity (for example, peptides, proteins, antibodies, non-peptide compounds, synthetic compounds, fermentation products, cell extracts, plant extracts, animal tissue extracts, blood plasma, etc.), and can be used for example as a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

The prophylactic/therapeutic agent can be produced in the same manner as described above.

(8) DNA Transgenic Animal

The present invention provides a non-human mammal bearing DNA encoding the protein of the present invention, which is exogenous (hereinafter abbreviated as the exogenous DNA of the present invention) or its variant DNA (sometimes simply referred to as the exogenous variant DNA of the present invention).

That is, the present invention provides:

(1) A non-human mammal bearing the exogenous DNA of the present invention or its variant DNA;

(2) The mammal according to (1), wherein the non-human mammal is a rodent;

(3) The mammal according to (2), wherein the rodent is mouse or rat; and, (4) A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and to utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, ovine, goat, rabbits, canine, feline, guinea pigs, hamsters, mice, rats, etc. Above all, preferred are rodents, especially mice (e.g., C57Bl/6 strain, DBA2 strain, etc. for a pure line and for a cross line B6C3F1 strain, BDF1 strain B6D2F1 strain, BALB/c strain, ICR strain, etc.), rats (Wistar, SD, etc.) or the like, since they are relatively short in ontogeny and life cycle from a standpoint of creating model animals for human disease.

"Mammals" in a recombinant vector that can be expressed in the mammals include the aforesaid non-human mammals, human, etc.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the protein of the present invention which is abnormal and exemplified by the DNA, etc. that expresses a protein for suppressing the function of the protein of the present invention which is normal.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, canine, feline, guinea pigs, hamsters, rats, mice, etc.) bearing the DNA of the present invention highly homologous to the human DNA.

As expression vectors for the protein of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, canine, feline, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle αx actin, preproencephalin A, vasopressin, etc. Among them, cytomegalovirus promoters, human protein elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of enhancing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from human or various mammals (e.g., rabbits, canine, feline, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal protein obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygotic animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the protein of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the protein of the present invention and the pathological mechanism of the disease associated with the protein of the present invention and to investigate how to treat these diseases.

The mammal in which the normal exogenous DNA of the present invention has been transfected has a symptom of increase or decrease in the protein of the present invention in a free form and can thus be applied for example to a test for screening of a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention is overexpressed, and may eventually develop the function inactive type inadaptability to the protein of the present invention by inhibiting the function of endogenous normal DNA. Therefore, the animal can be utilized as a pathologic model animal for such a disease. For example, using the abnormal DNA transgenic animal of the present invention, it is possible to elucidate the pathological mechanism of the function inactive type inadaptability to the protein of the present invention and investigate how to treat this disease.

As a specific example of the availability, the transgenic animal overexpressing the abnormal DNA of the present invention is expected to serve as an experimental model to elucidate the mechanism of the functional inhibition (dominant negative effect) of a normal protein by the abnormal protein of the present invention in the function inactive type inadaptability of the protein of the present invention.

The mammal in which the abnormal exogenous DNA of the present invention has been transfected has a symptom of increase or decrease in the protein of the present invention in a free form and can thus be applied for example to a test for screening of a prophylactic/therapeutic agent for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

Other potential applications of two kinds of the DNA transgenic animals of the present invention described above further include:

(1) Use as a cell source for tissue culture;

(2) Elucidation of the relation to a peptide that is specifically expressed or activated by the protein of the present invention, by direct analysis of DNA or RNA in tissues of the DNA transgenic animal of the present invention or by analysis of the peptide tissues expressed by the DNA;

(3) Research on the function of cells derived from tissues that are usually cultured only with difficulty, using cells in tissues bearing the DNA cultured by a standard tissue culture technique;

(4) Screening of an agent that enhances the function of cells using the cells described in (3) above; and, (5) Isolation and purification of the variant protein of the present invention and preparation of an antibody thereto; etc.

Furthermore, clinical conditions of a disease associated wit the protein of the present invention, including the function inactive type inadaptability to the protein of the present invention can be determined by using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal can serve to identify cells capable of producing the protein of the present invention, and to study in association with apoptosis, differentiation or propagation or on the mechanism of signal transduction in these properties to inspect any abnormality therein. Accordingly, the DNA transgenic animal can provide an effective research material for the protein of the present invention and for investigation of the function and effect thereof.

To develop a therapeutic agent for the treatment of diseases associated with the protein of the present invention, including the function inactive type inadaptability to the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

(9) Knockout Animal

The present invention provides a non-human mammal embryonic stem cell bearing the DNA of the present invention inactivated and a non-human mammal deficient in expressing the DNA of the present invention.

Thus, the present invention provides:

(1) A non-human mammal embryonic stem cell in which the DNA of the present invention is inactivated;

(2) The embryonic stem cell according to (1), wherein the DNA is inactivated by introducing a reporter gene (e.g., β-galactosidase gene derived from *Escherichia coli*);

(3) The embryonic stem cell according to (1), which is resistant to neomycin;

(4) The embryonic stem cell according to (1), wherein the non-human mammal is a rodent;

(5) The embryonic stem cell according to (4), wherein the rodent is mouse;

(6) A non-human mammal deficient in expressing the DNA of the present invention, wherein the DNA is inactivated;

(7) The non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) The non-human mammal according to (6), which is a rodent;

(9) The non-human mammal according to (8), wherein the rodent is mouse; and,

(10) A method of screening a compound that promotes or inhibits (preferably inhibits) the promoter activity to the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal, those described above are used.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the BDF1 mouse (F1 between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF1 mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In addition thereto, embryos are preferably collected at the 8-cell stage, cultured until the blastocyte stage and then used thereby to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about 106 cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for cytological study of the protein of the present invention in vitro.

The non-human mammal deficient in expression of the DNA of the present invention can be identified from a normal animal by measuring the mRNA level in the subject animal by a publicly known method, and indirectly comparing the degrees of expression.

As the non-human mammal, those as given above are used.

With respect to the non-human mammal deficient in expression of the DNA of the present invention, the DNA of the present invention can be knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between those deficient in heterozygous expression of the protein of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the protein of the present invention, such an animal can be a disease model suspected of inactivated biological activities of the protein of the present invention and thus, offers an effective study to investigate the causes for and therapy for these diseases.

(9a) Method of Screening the Compound having Therapeutic/Prophylactic Effects on Diseases Caused by Deficiency, Damages, etc. of the DNA of the Present Invention The non-human mammal deficient in expression of the DNA of the present invention can be employed for screening the compound having therapeutic/prophylactic effects on diseases caused by deficiency, damages, etc. of the DNA of the present invention.

That is, the present invention provides a method of screening a compound or its salt having an effect of treating/preventing diseases caused by the deficiency or damage of the DNA of he present invention, for example respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], which comprises administering a test compound to a non-human mammal deficient in expression of the DNA of the present invention and observing/determining changes in the animal.

As the non-human mammal deficient in expression of the DNA of the present invention, which can be employed for the screening method, the same examples as described above apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately chosen depending on the administration route, property of the test compound, etc.

For example, when a compound having a prophylactic/therapeutic effect on respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.] is screened, a test compound is administered to the non-human mammal deficient in expression of the DNA according to the present invention, and the tissue is observed with time for a difference in emphysema of the lung from that of a group not given the test compound.

In the screening method, when a test compound is administered to a test animal and the disease conditions of the test animal are improved by at least about 10%, preferably at least about 30% and more preferably at least about 50%, the test compound can be selected as the compound having therapeutic/prophylactic effects on the diseases described above.

The compound obtained using the above screening method is a compound selected from the test compounds described above and exhibits therapeutic/prophylactic effects on diseases caused by deficiencies, damages, etc. of the protein of the present invention. Therefore, the compound can be employed as a safe and low toxic prophylactic/therapeutic agents for these diseases. Furthermore, compounds derived from the compound obtained by the screening described above may also be used as well.

The compound obtained by the screening method above may form salts, and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical comprising the compound obtained by the above screening method or salts thereof can be manufactured in a manner similar to the method for preparing the pharmaceutical comprising the protein of the present invention described hereinabove.

Since the pharmaceutical preparation thus obtained is safe and low toxic, it can be administered to human or mammal (e.g., rat, mouse, guinea pig, rabbit, ovine, swine, bovine, equine, feline, canine, simian, etc.).

The dose of the compound or its salt may vary depending upon target disease, subject to be administered, route of administration, etc. For example, when the compound is orally administered, the compound is administered to the adult patient with pulmonary emphysema (as 60 kg body weight) generally in a dose of about 0.1 to 100 mg, preferably about 1.0 to 50 mg and more preferably about 1.0 to 20 mg. In parenteral administration, a single dose of the compound may vary depending upon subject to be administered, target disease, etc. When the compound is administered to the adult patient with breast cancer (as 60 kg body weight) in the form of an injectable preparation, it is advantageous to administer the compound in a single dose of about 0.01 to about 30 mg, preferably about 0.1 to about 20 mg and more preferably about 0.1 to about 10 mg a day. For other animal species, the corresponding dose as converted per 60 kg weight can be administered.

(9b) Method of Screening a Compound that Promotes or Inhibits the Activity of a Promoter to the DNA of the Present Invention The present invention provides a method of screening a compound or its salts that promote or inhibit the activity of a promoter to the DNA of the present invention, which comprises administering a test compound to a non-human mammal deficient in expression of the DNA of the present invention and detecting the expression of a reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The test compounds are those as given above.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are selected from the test compounds described above and that promote or inhibit the promoter activity to the DNA of the present invention.

The compound obtained by the screening method above may form salts, and may be used in the form of salts with physiologically acceptable acids (e.g., inorganic acids, etc.) or bases (e.g., alkali metals, etc.) or the like, especially in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succiniic acid, tartaric acid, citric acid, malic acid, oxalic acid, benzoic acid, methanesulfonic acid, benzenesulfonic acid, etc.) and the like.

The compound or its salt promoting or inhibiting the promoter activity to the DNA of the present invention can regulate the expression of the protein of the present invention and can regulate the functions of the said protein, and can thus be used for example as a prophylactic/therapeutic agent for diseases in respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.], preferably as a prophylactic/therapeutic agent for chronic obstructive pulmonary disease etc.

In addition, compounds derived from the compound obtained by the screening described above may also be used as well.

A pharmaceutical comprising the compound obtained by the above screening method or a salt thereof can be manufactured in a manner similar to the method for preparing the pharmaceutical comprising the protein of the present invention described above.

Since the pharmaceutical preparation thus obtained is safe and low toxic, it can be administered to human or mammal (e.g., rat, mouse, guinea pig, rabbit, ovine, swine, bovine, equine, feline, canine, simian, etc.).

A dose of the compound or its salt may vary depending on target disease, subject to be administered, route for administration, etc.; when the compound that inhibits the promoter activity to the DNA encoding the protein A of the present invention is orally administered, the compound is administered to the adult patient with pulmonary emphysema (as 60 kg body weight) normally in a daily dose of about 0.1 to 100 mg, preferably about 1.0 to 50 mg and more preferably about 1.0 to 20 mg. In parenteral administration, a single dose of the compound may vary depending on subject to be administered, target disease, etc. but when the compound of inhibiting the promoter activity to the DNA of the present invention is administered to the adult patient with pulmonary emphysema (as 60 kg body weight) in the form of injectable preparation, it is advantageous to administer the compound intravenously to the patient in a daily dose of about 0.01 to about 30 mg, preferably about 0.1 to about 20 mg and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the promoter activity to the DNA of the present invention and, can greatly contribute to elucidation of causes for various diseases suspected of deficiency in expression of the DNA of the present invention and for the development of prophylactic/therapeutic agents for these diseases.

In addition, a so-called transgenic animal (gene transferred animal) can be prepared by using a DNA containing the promoter region of the protein of the present invention, ligating genes encoding various proteins at the downstream and injecting the same into oocyte of an animal. It is thus possible to synthesize the protein therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the protein itself of the present invention.

In the specification, where bases, amino acids, etc. are expressed in abbreviations, they are denoted by abbreviations in accordance with the IUPAC-IUB Commission on Biochemical Nomenclature or by conventional abbreviations in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Sec: selenocysteine Substituents, protecting groups and reagents generally used in this specification are presented as the codes below.

Me: methyl group

Et: ethyl group

Bu: butyl group

Ph: phenyl group

TC: thiazolidine-4(R)-carboxamido group

Tos: p-toluenesulfonyl

CHO: formyl

Bzl: benzyl

Cl2-Bzl: 2,6-dichlorobenzyl

Bom: benzyloxymethyl

Z: benzyloxycarbonyl

Cl—Z: 2-chlorobenzyloxycarbonyl

Br—Z: 2-bromobenzyl oxycarbonyl

Boc: t-butoxycarbonyl

DNP: dinitrophenol

Trt: trityl

Bum: t-butoxymethyl

Fmoc: N-9-fluorenyl methoxycarbonyl

HOBt: 1-hydroxybenztriazole

HOOBt: 3,4-dihydro-3-hydroxy-4-oxo-1,2,3-benzotriazine

HONB: 1-hydroxy-5-norbornene-2,3-dicarboxyimide

DCC: N,N'-dicyclohexylcarbodiimide

The sequence identification numbers in the sequence listing of the specification indicates the following sequence.

[SEQ ID NO: 1]

This shows the base sequence of CH25H.

[SEQ ID NO: 2]

This shows the amino acid sequence of a protein translated from the base sequence represented by SEQ ID NO: 1.

[SEQ ID NO: 3]

This shows the base sequence of PLAB.

[SEQ ID NO: 4]

This shows the amino acid sequence of a protein translated from the base sequence represented by SEQ ID NO: 3.

[SEQ ID NO: 5]

This shows the base sequence of CSF3.

[SEQ ID NO: 6]

This shows the amino acid sequence of a protein translated from the base sequence represented by SEQ ID NO: 5.

[SEQ ID NO: 7]

This shows the base sequence of RHO6.

[SEQ ID NO: 8]

This shows the amino acid sequence of a protein translated from the base sequence represented by SEQ ID NO: 7.

[SEQ ID NO: 9]

This shows the base sequence of SFN.

[SEQ ID NO: 10]

This shows the amino acid sequence of a protein translated from the base sequence represented by SEQ ID NO: 9.

[SEQ ID NO: 11]

This shows the base sequence of SSB1.

[SEQ ID NO: 12]

This shows the amino acid sequence of a protein translated from the base sequence represented by SEQ ID NO: 11.

[SEQ ID NO: 13]

This shows the base sequence of TNFAIP3.

[SEQ ID NO: 14]

This shows the amino acid sequence of a protein translated from the base sequence represented by SEQ ID NO: 13.

[SEQ ID NO: 15]

This shows the base sequence of TNFAIP6.

[SEQ ID NO: 16]

This shows the amino acid sequence of a protein translated from the base sequence represented by SEQ ID NO: 15.

[SEQ ID NO: 17]

This shows the base sequence of IER3.

[SEQ ID NO: 18]

This shows the amino acid sequence of a protein translated from the base sequence represented by SEQ ID NO: 17.

[SEQ ID NO: 19]

This shows the base sequence of GADD45A.

[SEQ ID NO: 20]

This shows the amino acid sequence of a protein translated from the base sequence represented by SEQ ID NO: 21.

[SEQ ID NO: 21]

This shows the base sequence of GADD45B.

[SEQ ID NO: 22]

This shows the amino acid sequence of a protein translated from the base sequence represented by SEQ ID NO: 21.

[SEQ ID NO: 23]

This shows the base sequence of 1L1RN.

[SEQ ID NO: 24]

This shows the amino acid sequence of a protein translated from the base sequence represented by SEQ ID NO: 23.

[SEQ ID NO: 25]

This shows the base sequence of SOCS2.

[SEQ ID NO: 26]

This shows the amino acid sequence of a protein translated from the base sequence represented by SEQ ID NO: 25.

[SEQ ID NO: 27]

This shows the base sequence of SOCS3.

[SEQ ID NO: 28]

This shows the amino acid sequence of a protein translated from the base sequence represented by SEQ ID NO: 27.

[SEQ ID NO: 29]

This shows the base sequence of MMP19.

[SEQ ID NO: 30]

This shows the amino acid sequence of a protein translated from the base sequence represented by SEQ ID NO: 29.

[SEQ ID NO: 31]

This shows the base sequence of DUSP2.

[SEQ ID NO: 32]

This shows the amino acid sequence of a protein translated from the base sequence represented by SEQ ID NO: 31.

[SEQ ID NO: 33]

This shows the base sequence of DUSP5.

[SEQ ID NO: 34]

This shows the amino acid sequence of a protein translated from the base sequence represented by SEQ ID NO: 33.

[SEQ ID NO: 35]

This shows the base sequence of STC1.

[SEQ ID NO: 36]

This shows the amino acid sequence of a protein translated from the base sequence represented by SEQ ID NO: 35.

[SEQ ID NO: 37]

This shows the base sequence of LDLR.

[SEQ ID NO: 38]

This shows the amino acid sequence of a protein translated from the base sequence represented by SEQ ID NO: 37.

[SEQ ID NO: 39]

This shows the base sequence of TNFRSF10B.

[SEQ ID NO: 40]

This shows the amino acid sequence of a protein translated from the base sequence represented by SEQ ID NO: 39.

[SEQ ID NO: 41]

This shows the base sequence of TNFRSF12A.

[SEQ ID NO: 42]

This shows the amino acid sequence of a protein translated from the base sequence represented by SEQ ID NO: 41.

[SEQ ID NO: 43]

This shows the base sequence of MAP3K8.

[SEQ ID NO: 44]

This shows the amino acid sequence of a protein translated from the base sequence represented by SEQ ID NO: 43.

[SEQ ID NO: 45]

This shows the base sequence of EGR1.

[SEQ ID NO: 46]

This shows the amino acid sequence of a protein translated from the base sequence represented by SEQ ID NO: 45.

[SEQ ID NO: 47]

This shows the base sequence of EGR3.

[SEQ ID NO: 48]

This shows the amino acid sequence of a protein translated from the base sequence represented by SEQ ID NO: 47.

[SEQ ID NO: 49]

This shows the base sequence of ADAMTS 1.

[SEQ ID NO: 50]

This shows the amino acid sequence of a protein translated from the base sequence represented by SEQ ID NO: 49.

[SEQ ID NO: 51]

This shows the base sequence of TFPI2.

[SEQ ID NO: 52]

This shows the amino acid sequence of a protein translated from the base sequence represented by SEQ ID NO: 51.

[SEQ ID NO: 53]

This shows the base sequence of OSM.

[SEQ ID NO: 54]

This shows the amino acid sequence of a protein translated from the base sequence represented by SEQ ID NO: 53.

[SEQ ID NO: 55]

This shows the base sequence of TNC.

[SEQ ID NO: 56]

This shows the amino acid sequence of a protein translated from the base sequence represented by SEQ ID NO: 55.

[SEQ ID NO: 57]

This shows the base sequence of EDG3.

[SEQ ID NO: 58]

This shows the amino acid sequence of a protein translated from the base sequence represented by SEQ ID NO: 57.

[SEQ ID NO: 59]

This shows the base sequence of GPR73L1.

[SEQ ID NO: 60]

This shows the amino acid sequence of a protein translated from the base sequence represented by SEQ ID NO: 59.

[SEQ ID NO: 61]

This shows the base sequence of SFRP2.

[SEQ ID NO: 62]

This shows the amino acid sequence of a protein translated from the base sequence represented by SEQ ID NO: 61.

[SEQ ID NO: 63]

This shows the base sequence of HIMAP2.

[SEQ ID NO: 64]

This shows the amino acid sequence of a protein translated from the base sequence represented by SEQ ID NO: 63.

[SEQ ID NO: 65]

This shows the base sequence of SSTR1.

[SEQ ID NO: 66]

This shows the amino acid sequence of a protein translated from the base sequence represented by SEQ ID NO: 65.

[SEQ ID NO: 67]

This shows the base sequence of primer 1 used in detection of the expression level of CH25H gene.

[SEQ ID NO: 68]

This shows the base sequence of primer 2 used in detection of the expression level of CH25H gene.

[SEQ ID NO: 69]

This shows the base sequence of primer 3 used in EXAMPLE 5.

[SEQ ID NO: 70]

This shows the base sequence of primer 4 used in EXAMPLE 5.

[SEQ ID NO: 71]

This shows the base sequence of primer 5 used in EXAMPLE 5.

[SEQ ID NO: 72]

This shows the base sequence of primer 6 used in EXAMPLE 5.

[SEQ ID NO: 73]

This shows the amino acid sequence of the antigenic peptide used in EXAMPLE 5.

EXAMPLES

Hereinafter the present invention will be described more specifically by referring to EXAMPLES but is not deemed to be limited thereto.

Example 1

(1) Acquisition of Excised Lung Samples from Lung Cancer Patients with a Complication of COPD From lung cancer patients required to undergo lung excision, lung samples removed in a lung excision operation were provided as materials for study. For acquisition of the lung samples, we obtained an approval of Ethical Committee in Tohoku University and an informed consent from the patients.

In diagnosis of COPD, we measured patients' vital capacity (VC (L)), % lung capacity (% VC), forced vital capacity (FVC (L)), % forced vital capacity (% FVC), forced expiratory volume in 1 second (FEV1 (L)), % forced expiratory volume in 1 second (% FEV1), one-second forced expiratory volume rate (%) (FEV1/FVC (%)), total lung capacity (TLC (L)), % total lung capacity (% TLC), functional residual capacity (FRC (L)), % functional residual capacity (% FRC), residual capacity (RC (L)), % residual volume (% RV), residual ratio (RV/TLC (%)), Diffusing capacity of the lung for carbon monoxide (DLCO), % Diffusing capacity of the lung for carbon monoxide (% DLCO), alveolar ventilation (DLCO/VA), arterial blood oxygen partial pressure ($PaO_2$), arterial blood carbon dioxide partial pressure ($PaCO_2$), bicarbonate ion ($HCO_3$), and functional residual ratio (FRC/TLC (%)), and a patient showing $FEV_1/FVC < 70\%$ and % $FEV_1$ [□] ≧80% was diagnosed as a light case (stage I) COPD, a patient showing $FEV_1/FVC < 70\%$ and 50% <% $FEV_1$ <80% was diagnosed as a moderate case (stage IIA) COPD, and a patient showing $FEV_1/FVC < 70\%$ and 30% <% $FEV_1$ <50% was diagnosed as a moderate case (stage IIB) COPD.

A patient with lung cancer showing $FEV_1/FVC \geqq 70\%$ and free from symptoms such as chronic cough and phlegm was diagnosed as non-COPD.

Further, smoking history was investigated, and a patient without smoking history was classified into non-smoker, a patient with smoking history in the past was classified into ex-smoker, and a patient who smokes even at present was classified into smoker.

The patients with lung cancer were classified into a non-COPD and no-smoker group (NN group, 12 cases), a non-COPD and ex-smoker group (NE group, 6 cases), a non-COPD and smoker group (NS group, 5 cases), a stage I COPD group (CE1 group, 7 cases), a stage IIA COPD group (CE2A group, 6 cases) and a stage IIB COPD group (CE2B group, 2 cases).

(2) Searching for Genes Whose Expression Fluctuated in Lung Tissues of COPD Patients To reveal genes whose expression fluctuated specifically in lung tissues of COPD patients, lung tissue samples after the operation of removing the lungs from the lung cancer patients with a complication of COPD were frozen in liquid nitrogen, then milled with a frozen-tissue milling device, and immersed in Isogen (Nippon Gene) in a 10-fold excess amount relative to the wet lungs, to prepare total RNAs according to its attached protocol. Among all samples from which total RNAs were prepared, total RNAs from the NN group (5 cases), NE group (3 cases), NS group (2 cases), CE1 group (3 cases), and CE2A group (2 cases) were used as materials, and the 15 samples in total were used in gene expression analysis with an oligonucleotide microarray (Human Genome U133A, U133B; AFFYMETRIX™). The experimental method was in accordance with an experimental guide (Expression analysis technical manual) from AFFYMETRIX™.

The expression level of each gene was expressed as expression level assuming that the central value of expression levels of all genes in each oligonucleotide microarray was 1, and the mean among the groups was determined and compared as the gene expression value in each group.

The fluctuation of gene expression (COPD/non) in COPD was calculated according to the following equation, and the results are shown in Tables 1, 2 and 3.

$$COPD/non = \frac{\dfrac{(CE1\text{ group (3 cases) gene expression value} + CE2A\text{ group (2 cases) gene expression value})}{5}}{\dfrac{(NN\text{ group (5 cases) gene expression value} + NE\text{ group (3 cases) gene expression value} + NS\text{ group (2 cases) gene expression value})}{10}}$$

TABLE 1

| Symbol of gene | Name of gene | NN | NE | NS | CE1 | CE2A | COPD/non |
|---|---|---|---|---|---|---|---|
| CH25H | cholesterol 25-hydroxylase | 0.58 | 0.67 | 1.15 | 1.71 | 3.16 | 3.2 |
| PLAB | prostate differentiation factor(=GDF15) | 1.27 | 1.05 | 1.92 | 5.19 | 6.90 | 4.4 |
| CSF3 | colony stimulating factor 3 (granulocyte) | 0.12 | 0.02 | 0.54 | 4.22 | 1.46 | 17.9 |
| RHO6 | GTP-binding protein(=Rho6, Socius) | 0.54 | 0.22 | 1.10 | 6.09 | 2.90 | 8.6 |
| SFN | stratifin | 0.47 | 0.61 | 0.97 | 5.57 | 2.82 | 7.3 |
| SSB1 | SPRY domain-containing SOCS box protein SSB-1 | 0.43 | 0.36 | 0.46 | 2.02 | 1.71 | 4.6 |
| TNFAIP3 | tumor necrosis factor, alpha-induced protein 3 | 0.91 | 0.98 | 2.36 | 5.08 | 5.80 | 4.4 |
| TNFAIP6 | tumor necrosis factor, alpha-induced protein 6 | 0.19 | 0.29 | 0.73 | 1.02 | 1.76 | 4.0 |
| IER3 | immediate early response 3 | 4.00 | 6.59 | 11.53 | 27.43 | 26.59 | 4.3 |
| GADD45A | growth arrest and DNA-damage-inducible, alpha | 0.80 | 0.96 | 1.54 | 3.54 | 3.99 | 3.7 |
| GADD45B | growth arrest and DNA-damage-inducible, beta | 2.61 | 3.02 | 5.62 | 13.79 | 7.83 | 3.4 |
| IL1RN | interleukin 1 receptor antagonist | 0.90 | 1.00 | 1.61 | 5.05 | 1.91 | 3.5 |
| SOCS2 | suppressor of cytokine signaling 2 | 0.88 | 0.70 | 1.45 | 3.42 | 2.33 | 3.2 |
| SOCS3 | suppressor of cytokine signaling 3 | 0.54 | 0.67 | 1.64 | 2.94 | 2.37 | 3.4 |
| MMP19 | matrix metalloproteinase 19 | 0.81 | 0.86 | 0.69 | 3.32 | 1.82 | 3.4 |

TABLE 2

| | | | | | | | |
|---|---|---|---|---|---|---|---|
| DUSP2 | dual specificity phosphatase 2 | 0.16 | 0.37 | 0.90 | 1.51 | 0.81 | 3.3 |
| DUSP5 | dual specificity phosphatase 5 | 1.04 | 1.08 | 3.91 | 4.73 | 3.40 | 2.6 |
| STC1 | stanniocalcin 1 | 0.19 | 0.26 | 0.30 | 0.82 | 0.66 | 3.2 |
| LDLR | low density lipoprotein receptor (familial hypercholesterolemia) | 3.88 | 2.83 | 7.28 | 15.77 | 8.80 | 3.1 |
| TNFRSF10B | tumor necrosis factor receptor superfamily, member 10b | 0.74 | 0.79 | 1.30 | 2.39 | 1.71 | 2.4 |
| TNFRSF12A | tumor necrosis factor receptor superfamily, member 12A | 1.75 | 1.56 | 2.14 | 5.39 | 4.89 | 2.9 |
| MAP3K8 | mitogen-activated protein kinase kinase kinase 8 | 0.21 | 0.20 | 0.29 | 0.56 | 0.64 | 2.6 |
| EGR1 | early growth response 1 | 2.96 | 2.66 | 4.52 | 6.34 | 6.24 | 2.0 |
| EGR3 | early growth response 3 | 0.39 | 0.81 | 1.15 | 1.42 | 2.36 | 2.7 |
| ADAMTS1 | a disintegrin-like and metalloprotease (reprolysin type) with thrombospondin type 1 motif, 1 | 1.21 | 1.60 | 4.40 | 3.92 | 3.26 | 1.9 |
| TFPI2 | tissue factor pathway inhibitor 2 | 0.34 | 1.81 | 0.65 | 0.93 | 2.22 | 1.7 |
| OSM | oncostatin M | 0.33 | 0.43 | 0.97 | 1.65 | 1.04 | 2.89 |
| TNC | ESTs | 0.25 | 0.31 | 0.65 | 0.73 | 1.02 | 2.43 |
| EDG3 | endothelial differentiation, sphingolipid G-protein-coupled receptor, 3 | 0.20 | 0.22 | 0.50 | 0.40 | 0.82 | 2.15 |
| GPR73L1 | G protein-coupled receptor 73-like 1 | 0.20 | 0.30 | 0.41 | 0.51 | 0.60 | 2.01 |
| SFRP2 | secreted frizzled-related protein 2 | 1.43 | 9.16 | 13.52 | 6.87 | 16.04 | 1.71 |

TABLE 3

| Symbol of gene | Name of gene | NN | NE | NS | CE1 | CE2A | COPD/non |
|---|---|---|---|---|---|---|---|
| HIMAP2 | DKFZP586D0824 protein | 0.95 | 0.93 | 0.85 | 0.40 | 0.39 | 0.43 |
| SSTR1 | somatostatin receptor 1 | 0.73 | 0.61 | 0.47 | 0.17 | 0.33 | 0.36 |

As a result, CH25H (NH_003956) (SEQ ID NO: 1), PLAB (AF003934) (SEQ ID NO: 3), CSF3 (NM_000759) (SEQ ID NO: 5), RH06 (NM_014470) (SEQ ID NO: 7), SFN (BC000329) (SEQ ID NO: 9), SSB1 (NM_25106) (SEQ ID NO: 11), TNFAIP3 (NM_006290) (SEQ ID NO: 13), TNFAIP6 (NM_007115) (SEQ ID: 15), IER3 (NM_003897) (SEQ ID NO: 17), GADD45A (NM_001924) (SEQ ID NO: 19), GADD45B (AF087853) (SEQ ID NO: 21), IL1RN (NM_173841) (SEQ ID NO: 23), SOCS2 (NM_003877) (SEQ ID NO: 25), SOCS3 (NM_003955) (SEQ ID NO: 27), MMP19 (U38321) (SEQ ID NO: 29), DUSP2 (NM_004418) (SEQ ID NO: 31), DUSP5 (U16996) (SEQ ID NO: 33), STC1 (U46768) (SEQ ID NO: 35), LDLR (NM_000527) (SEQ ID NO: 37), TNFRSF10B (AF016266) (SEQ ID NO: 39), TNFRSF12A (NM_016639) (SEQ ID NO: 41), MAP3K8 (NM_005204) (SEQ ID NO: 43), EGR1 (NM_001964) (SEQ ID NO: 45), EGR3 (NM_004430) (SEQ ID NO: 47), ADAMTS1 (NM_006988) (SEQ ID NO: 49), TFPI2 (L27624) (SEQ ID NO: 51), OSM (NM_020530) (SEQ ID NO: 53), TNC (NM_002160) (SEQ ID NO: 55), EDG3 (NM_005226) (SEQ ID NO: 57), GPR73L1 (NM_144773) (SEQ ID NO: 59) and SFRP2 (AY359001) (SEQ ID NO: 61) were detected as genes whose expression was increased as the morbid state of COPD proceeded (Tables 1 and 2).

HIMAP2 (NM_015660) (SEQ ID NO: 63) and SSTR1 (NM_001049) (SEQ ID NO: 65) were detected as genes whose expression was decreased as the morbid state of COPD proceeded (Table 3).

Example 2

Analysis of Correlation Between Expression Fluctuation and Respiratory Functions To determine whether the expression of the genes whose expression was observed to fluctuate in EXAMPLE 1 was related to the morbid state of COPD, the correlation between the expression level of each gene and respiratory functions (% forced expiratory volume in 1 second, % CO lung diffusing capacity) was analyzed.

It was found that the expression of CH25H (SEQ ID NO: 1), PLAB (SEQ ID NO: 3), CSF3 (SEQ ID NO: 5), RHO6 (SEQ ID NO: 7), SFN (SEQ ID NO: 9), SSB1 (SEQ ID NO: 11), TNFAIP3 (SEQ ID NO: 13), TNFAIP6 (SEQ ID: 15), IER3 (SEQ ID NO: 17), GADD45A (SEQ ID NO: 19), GADD45B (SEQ ID NO: 21), IL1RN (SEQ ID NO: 23), SOCS2 (SEQ ID NO: 25), SOCS3 (SEQ ID NO: 27), MMP19 (SEQ ID NO: 29), DUSP2 (SEQ ID NO: 31), DUSP5 (SEQ ID NO: 33), STC1 (SEQ ID NO: 35), LDLR (SEQ ID NO: 37), TNFRSF10B (SEQ ID NO: 39), TNFRSF12A (SEQ ID NO: 41), MAP3K8 (SEQ ID NO: 43), EGR1 (SEQ ID NO: 45), EGR3 (SEQ ID NO: 47), ADAMTS1 (SEQ ID NO: 49), TFPI2 (SEQ ID NO: 51), OSM (SEQ ID NO: 53), TNC (SEQ ID NO: 55), EDG3 (SEQ ID NO: 57), GPR73L1 (SEQ ID NO: 59), SFRP2 (SEQ ID NO: 61), HIMAP2 (SEQ ID NO: 63) and SSTR1 (SEQ ID NO: 65) was correlated with the respiratory functions (% forced expiratory volume in 1 second, % CO lung diffusing capacity).

Example 3

(1) Confirmation of Fluctuation in Expression of CH25H Gene by Quantitative RT-PCR Method The fluctuation in expression of CH25H (SEQ ID NO: 1) was examined by the quantitative RT-PCR method using the whole lung excised samples [NN group (12 cases), NE group (6 cases), NS group (5 cases), CE1 group (7 cases), CE2A group (6 cases)].

Figure 2:
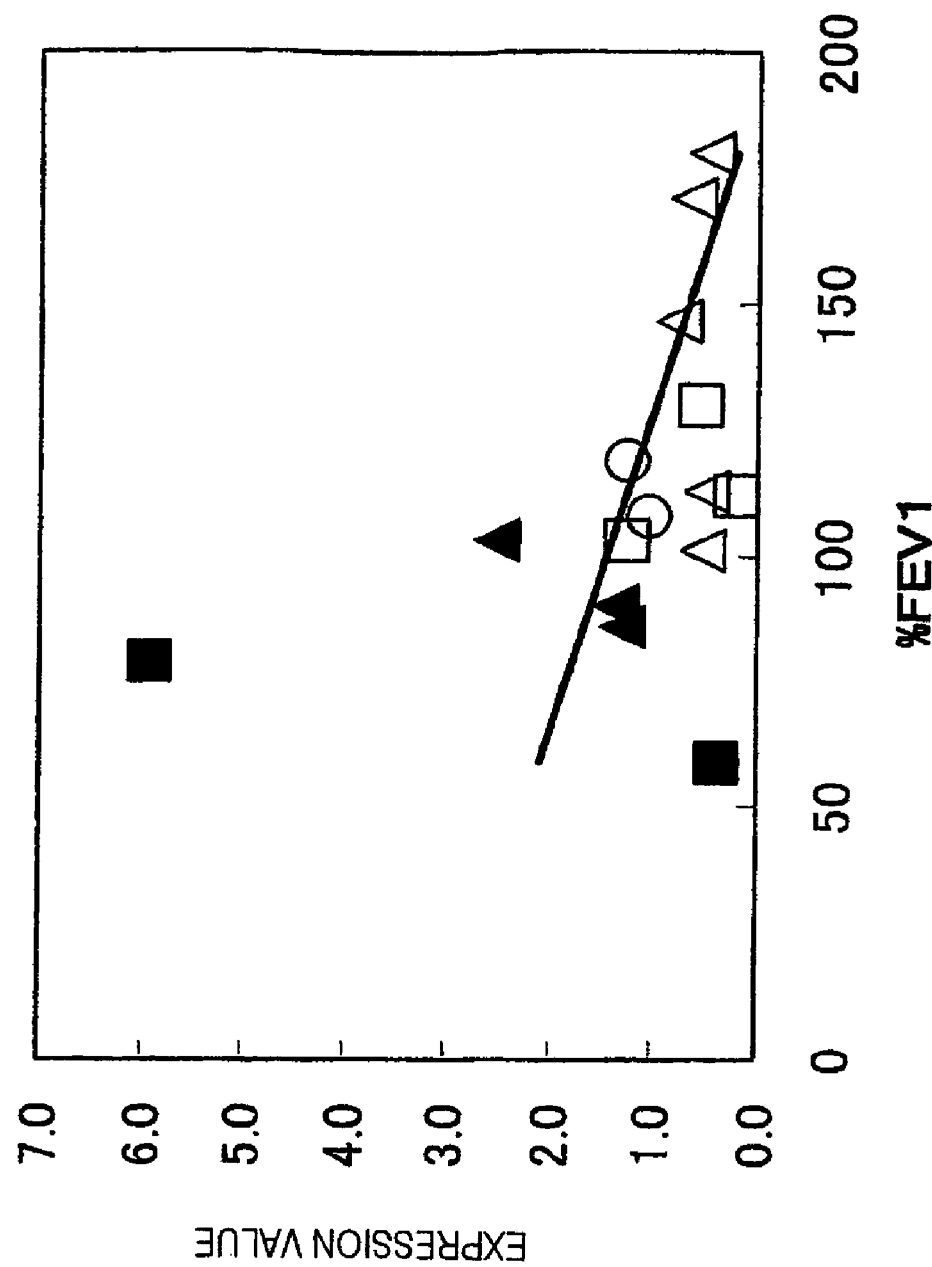
FIG. 2 is a graph showing the correlation between the expression level of CH25H gene and forced expiratory volume in 1 second (% FEV 1). In the graph, Δ shows the NN group, □ shows the NE group, ○ shows the NS group, ▲ shows CE1 group, and ■ shows the CE2A group. The expression level of CH25H gene is shown in the ordinate and volume in 1 second (% FEV1) in the abscissa. r (correlation factor)=0.36. p (statistically significant difference)=1.9.
Figure 3:
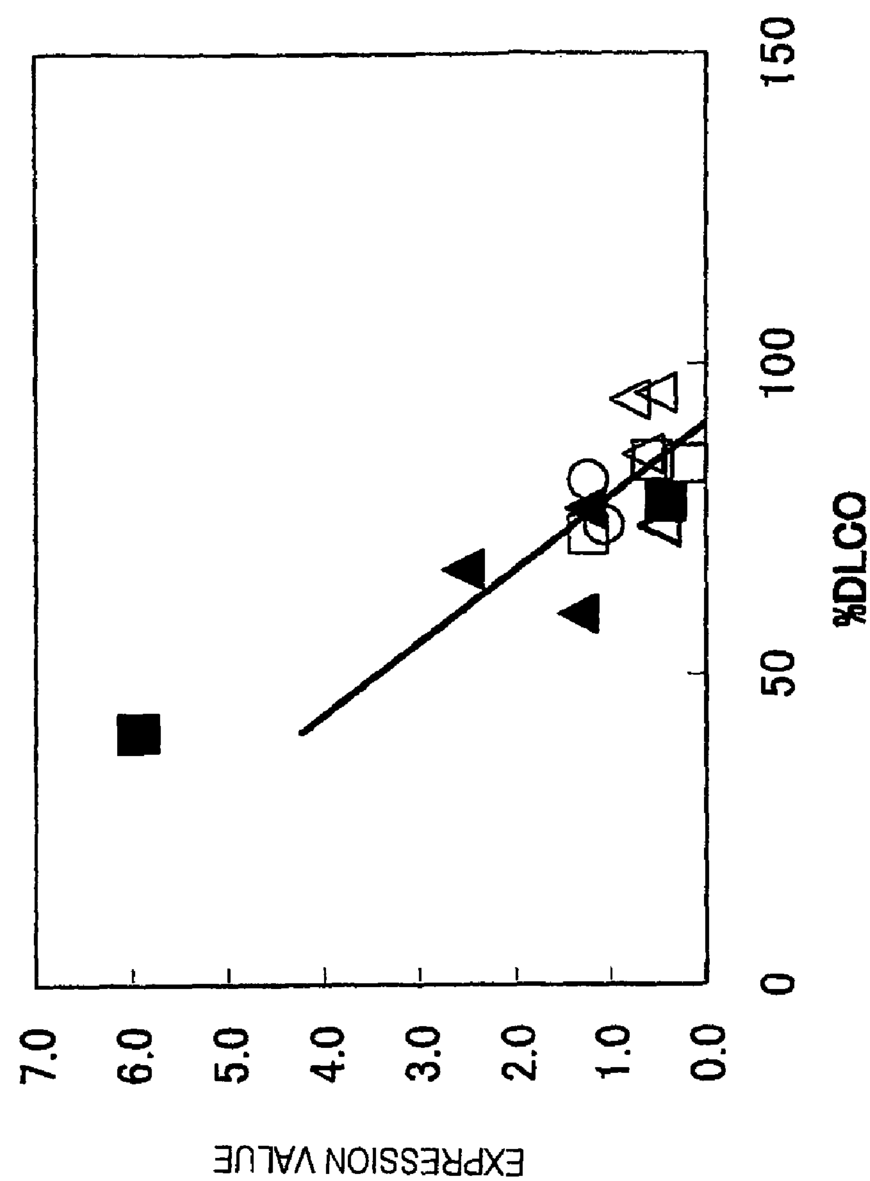
FIG. 3 is a graph showing the correlation between the expression level of CH25H gene and % Diffusing capacity of the lung for carbon monoxide (% DLCO). In the graph, Δ shows the NN group, □ shows the NE group, ○ shows the NS group, ▲ shows CE1 group, and ■ shows the CE2A group. The expression level of CH25H gene is shown in the ordinate and % Diffusing capacity of the lung for carbon monoxide % DLCO in the abscissa. r (correlation factor)=−0.81. p (statistically significant difference)=0.0002.

Using 500 ng total RNA prepared in EXAMPLE 1 as the starting material, cDNA was synthesized by reverse transcription reaction in 50 µl reaction solution with TaqMan Gold RT-PCR Kit (Applied Biosystems). The reaction solution was diluted 2.5-fold with distilled water, and 2 µl of the dilution was used in real-time quantitative PCR method using ABI PRISM 7900 sequence detection system (Applied Biosystems) and QuantiTect SYBR Green PCR Kit (QIAGEN) to determine the Ct value of each gene. The primers used in the quantitative PCR were designed using Primer Express program (Applied Biosystems) [primer 1 (SEQ ID NO: 67), primer 2 (SEQ ID NO: 68)]. The Ct value of GAPDH gene as house-keeping gene was determined in an analogous manner using TaqMan GAPDH control reagents (Applied Biosystems), and by the ΔCT method, the expression level of CH25H gene per GAPDH gene was determined, and expression per individual among the groups was compared (FIG. 1). Further, the correlation between the gene expression levels of the total samples [NN group (12 cases), NE group (6 cases), NS group (5 cases), CE1 group (7 cases), CE2A group (6 cases)] and the respiratory functions (% forced expiratory volume in 1 second, % CO lung diffusing capacity) was analyzed (FIGS. 2 and 3).

It was thereby confirmed that the expression of CH25H gene (SEQ ID NO: 1) was increased in the lungs of the COPD patients.

CH25H is a kind of cholesterol hydroxylase. Accordingly, how the expression of each of CYP3A4, CYP7A1, CYP46 and CYP27A1, that is, cholesterol hydroxylases other than CH25H, was changed in the COPD patients was examined by extracting and comparing the expression values of the respective genes from the GeneChip data shown in EXAMPLE 1. As a result, the expression of each of CYP3A4, CYP7A1, CYP46 and CYP27A1 did not fluctuate in the COPD patients. It was thus found that the cholesterol hydroxylase whose expression fluctuated as the morbid state of COPD proceeded was only CH25H.

(2) Distribution of CH25H Gene in Tissues

The distribution of CH25H, CYP3A4, CYP7A1, CYP46 and CYP27A1 in tissues was examined by using 2 µl Human MTC Panel I, Human MTC Panel II, Human Immune System MTC Panel, Human Blood Fractions MTC Panel (all of which are manufactured by Clontech), and the gene expression levels therein were measured according to the quantitative PCR shown in EXAMPLE 1. As each probe, the corresponding probe was selected from Assays on demand gene expression product (Applied Biosystems) and used.

As a result, CH25H had been expressed specifically in the lung. Except for CH25H, only CYP27A1 had been expressed at high level in the lung.

From the foregoing, it is estimated that CH25H is a sole cholesterol hydroxylase participating in the morbid state of COPD.

Example 4

Analysis of Fluctuation in CH25H Gene Expression in COPD Model Mouse

To examine the involvement of CH25H in the morbid state of COPD, the analysis of functions of CH25H was conducted by using a cigarette smoke-exposed mouse reflecting the morbid state of COPD (Toxicological Science vol. 51, pp. 289-299, 1999).

First, a fluctuation in expression of mouse CH25H gene in a pulmonary/bronchial lavage fluid of the mouse exposed to cigarette smoke was examined.

The mouse exposed to cigarette smoke was created by exposing a C57BL/6 mouse (7-week-old, male) to cigarette smoke under the following conditions. As the cigarette smoke, 3% diluted smoke of Kentucky reference cigarette 2R4F from which a filter had been cut off was used, and the mouse was exposed daily to 150 puffs/15 min→interval/15 min→150 puffs/15 min→interval/15 min→150 puffs/15 min→interval/15 min→150 puffs/15 min (40 cigarettes). After exposure for 2 or 3 days, the lung was excised, and according to the method shown in EXAMPLE 1, total RNA was prepared. Subsequently, the expression levels of mouse CH25H gene and mouse CYP27A1 gene were measured according to the real-time quantitative PCR method shown in EXAMPLE 1. A tracheal canula was introduced into the mouse under anesthesia with pentobarbital after exposure to cigarette smoke for 3 days, and 0.5 ml PBS was injected 3 times into the lung and recovered the fluid therefrom. A fluctuation in the expression of mouse CH25H and mouse CYP27A1 in inflammatory cells in the bronchoalveolar lavage fluid was also analyzed. As each probe, the corresponding probe was selected from Assays on demand gene expression product (Applied Biosystems) and used. The expression level of each gene was calculated as relative expression value to rodent GAPDH by the comparative Ct value method.

Figure 4:
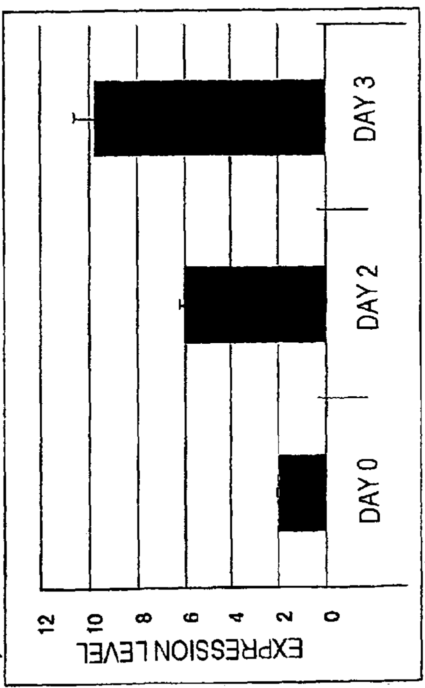
FIG. 4(A) is a graph showing the expression levels of CH25H gene and CYP27A1 gene in the lung of a mouse exposed to cigarette smoke. In the graph, the expression level of each gene is shown in the ordinate and the duration of exposure to cigarette smoke in the abscissa.
FIG. 4(B) is a graph showing the expression levels of CH25H gene and CYP27A1 gene in cells in a bronchoalveolar lavage fluid from a mouse exposed to cigarette smoke. In the graph, the expression level of each gene is shown in the ordinate and the duration of exposure to cigarette smoke in the abscissa.
Figure 4:
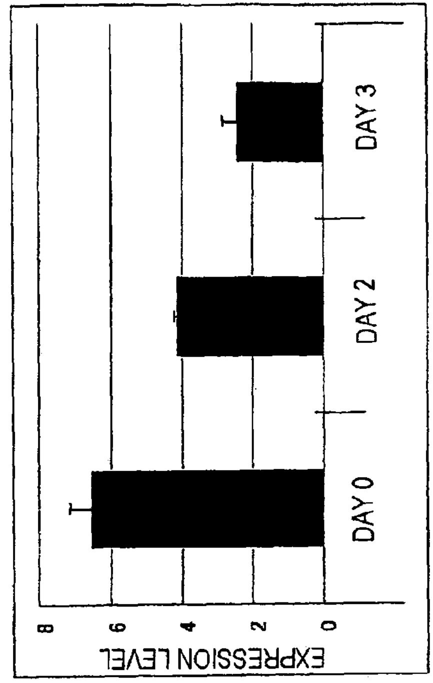
Figure 4:
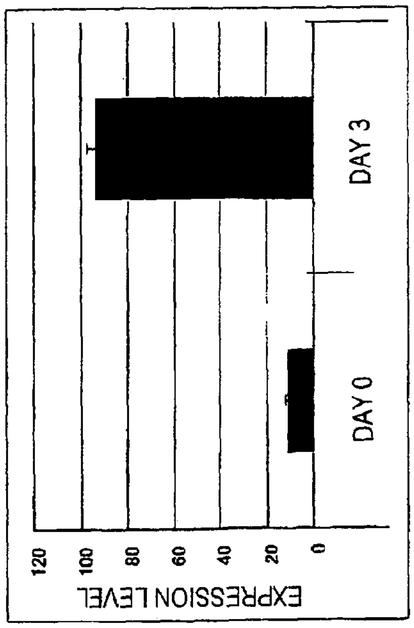
Figure 4:
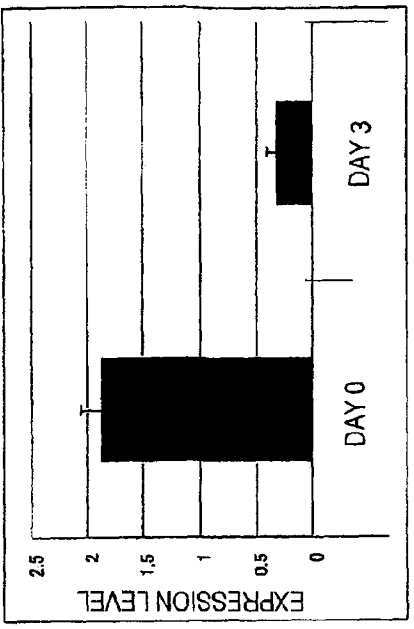

As a result, the expression of the mouse CH25H gene was increased in the pulmonary/bronchoalveolar lavage fluid by exposure to cigarette smoke (FIGS. 4A, B). On the other hand, the gene expression of CYP27A1 which is another cholesterol hydroxylase known to be expressed in the lung was reduced by exposure to cigarette smoke (FIGS. 4A, B).

From these results, it was found that the expression of CH25H is increased in the cigarette smoke-exposed model reflecting the morbid state of COPD.

Example 5

Fluctuation in the Amount of 25-Hydroxycholesterol (25-HC) in Lung Tissue in COPD Model Mouse To examine the involvement of CH25H in the morbid state of COPD, the cigarette smoke-exposed mouse reflecting the morbid state of COPD used in EXAMPLE 1 was used to examine the fluctuation in the amounts of 25-HC and cholesterol in the lung tissue.

The cigarette smoke-exposed mouse had been exposed to cigarette smoke under the same conditions as in EXAMPLE 1. The number of days on which the mouse was exposed to cigarette smoke was 1, 3 or 9, and 24 hours after the final exposure, the mouse was killed by administering an excess of pentobarbital, and the lung was excised. The lung was stored at −80° C. prior to measurement of the amounts of 25-HC and cholesterol.

Figure 5:
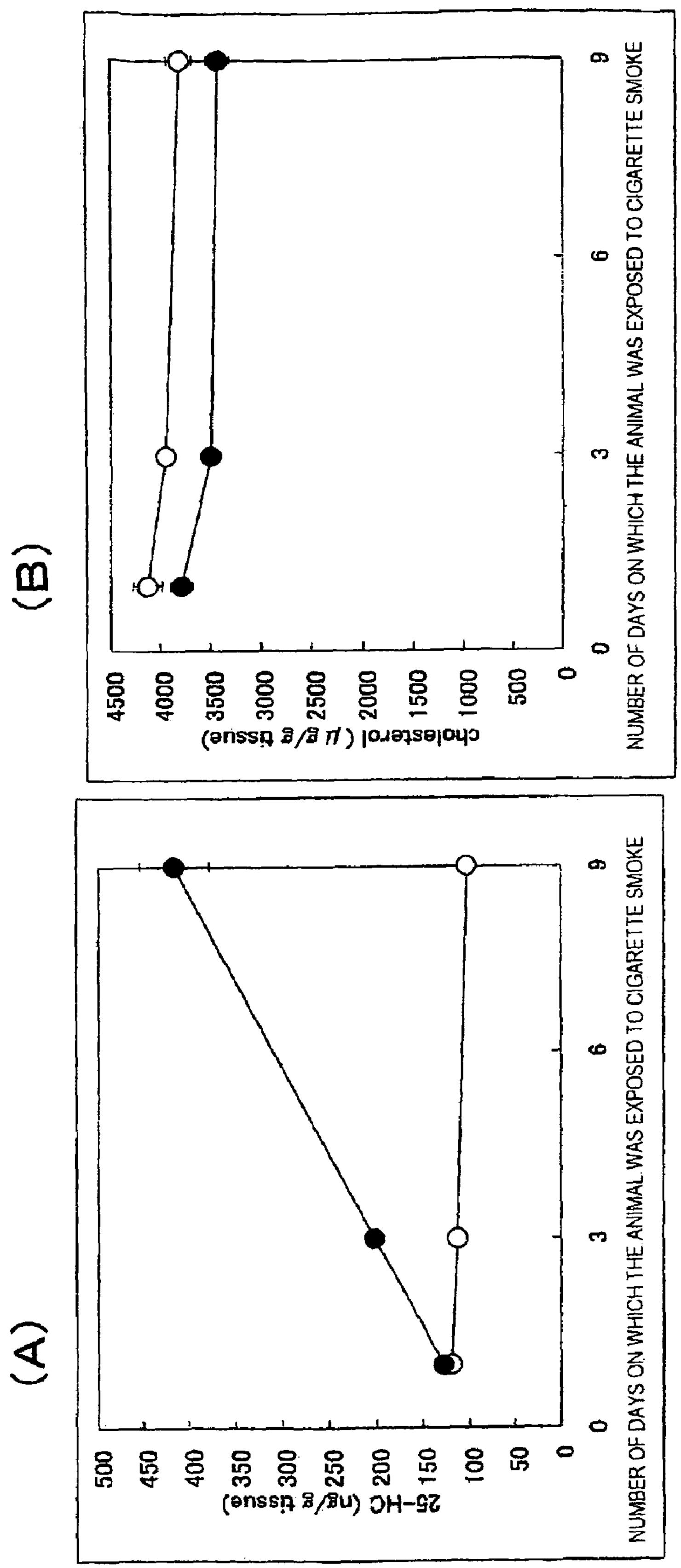
FIG. 5(A) is a graph showing a fluctuation in the amount of 25-hydroxycholesterol (25-HC) in the lung tissue of a mouse exposed to cigarette smoke. In the graph, the amount of 25-HC is shown in the ordinate, and the number of days on which the mouse was exposed to cigarette smoke is shown in the abscissa. ● shows 25-HC, and ○ shows the control.
FIG. 5(B) is a graph showing a fluctuation in the amount of cholesterol in the lung tissue of a mouse exposed to cigarette smoke. In the graph, the amount of cholesterol is shown in the ordinate, and the number of days on which the mouse was exposed to cigarette smoke is shown in the abscissa. ● shows 25-HC, and ○ shows the control.

The amounts of 25-HC and cholesterol were measured by LC/MS/MS (API 4000, Applied Biosystems/MDS Sciex) [HPLC conditions: HPLC (Shimadzu 10A), analysis column (CAPCELLPAK C18MGII, Shiseido Co., Ltd.), MS/MS conditions: MS/MS (API 4000), Ionization mode (APCI), Ion polarity mode (positive)]. The result indicated that as the number of days on which the mouse was exposed to cigarette smoke was increased, the amount of 25-HC in the lung tissue was increased (FIG. 5A). On the other hand, no fluctuation in the amount of cholesterol was observed (FIG. 5B).

Example 6

(1) Cloning of CH25H Gene and Construction of Expression Plasmid

Referring to human CH25H gene sequence (NM_003956) and mouse CH25H gene sequence (NM_009890), primers for cloning human and mouse CH25H full-length genes [primer 3 (SEQ ID NO: 69), primer 4 (SEQ ID NO: 70), primer 5 (SEQ ID NO: 71) and primer 6 (SEQ ID NO: 72)] (manufactured by Hokkaido System Science) were synthesized. Using these primers and lung Marathon cDNA library (Clontech) as the template for the human gene or spleen Marathon cDNA library (Clontech) as the template for the mouse gene, each full-length gene was amplified by using PyroBest polymerase and Ex-Taq polymerase (Takara Shuzo Co., Ltd.) according to its attached manual. Each PCR product was inserted into pCR BluntII TOPO vector (Invitrogen) according to its attached manual (pCRII BluntII TOPO-hCH25H and pCRII BluntII TOPO-mCH25H). Subsequently, BamHI-XhoI fragments containing hCH25H and mCH25H gene fragments were cut off from the resulting pCRII BluntII TOPO-hCH25H and pCRII BluntII TOPO-mCH25H, respectively, and then inserted into pcDNA3.1 (+) vector (Invitrogen), whereby human CH25H expression plasmid (pcDNA-hCH25H) and mouse CH25H expression plasmid (pcDNA-mCH25H) were constructed.

(2) Identification of CH25H Expression Site (2-1) Identification of CH25H Gene Expression Site by in situ Hybridization The mouse CH25H gene-harboring plasmid (pCRII BluntII TOPO-mCH25H) constructed in (1) above was digested with BamHI and XhoI respectively to prepare a linear DNA having T7 promoter binding site downstream from the mouse CH25H gene and a linear DNA having SP6 promoter binding site. Using DIG RNA labeling kit (Roche Diagnostics) with these DNAs as the template, mouse CH25H antisense RNA and sense RNA were prepared according to its attached protocol. For MMP-12 gene as the control, antisense RNA and sense RNA were prepared.

According to the method described in EXAMPLE 4, the lung was excised from a mouse exposed to cigarette smoke for 3 months, then fixed with 4% paraformaldehyde, cut into a 10 μm section with a cryostat, attached onto APS-coated slide glass and used as a sample. Hybridization was carried out by using in situ hybridization reagents (Nippon Gene) according to the attached protocol. Detection of the RNA probe was carried out by using the DIG detection kit (Roche Diagnostics).

As a result, the expression of CH25H was observed in cells distributed widely in the lung and agreed with the distribution of expression of MMP-12 used as the control, and thus the cells expressing CH25H were estimated to be alveolar macrophages.

(2-2) Identification of CH25H Expression Site by Immunostaining

For confirming the expression site of CH25H, the expressing cells were identified by immunostaining with CH25H antibody. A peptide (SEQ ID NO: 73, manufactured by MBL) synthesized on the basis of a method described by Lund et al. (The Journal of Biological Chemistry, vol. 273, pp. 34316-34327, 1998), together with KHL, was used to immunize rabbits. The serum after 5th immunization was purified through a peptide column to prepare anti-CH25H antibody.

According to the method described in EXAMPLE 4, the lung was excised from the mouse exposed to cigarette smoke for 3 months and cut into a 10 μm section with a cryostat to prepare a sample. After drying with air, the section was fixed with Mildform for 15 minutes, then reacted with 0.3% $H_2O_2$/MeOH for 30 minutes, and blocked for 1 hour with Block Ace (Snowbrand Co., Ltd.). Thereafter, the sample was reacted with macrophage-recognizing anti-mouse F4/80 antibody (UK-Serotec), AlexaFluor 594-labeled anti-rat IgG antibody (Molecular Probe), anti-mouse CH25H antibody, and AlexaFluor 488-labeled anti-rabbit IgG antibody (Molecular Probe) in this order each for 30 minutes. The sample was washed with PBS/0.1% Triton X-100, then subjected to nuclear staining/encapsulation with VECTASHIELD with DAPI (manufactured by VECTOR) and observed and photographed under a fluorescence microscope.

As a result, positive cells with the anti-mouse F4/80 antibody agreed completely with positive cells with the anti-mouse CH25H antibody, thus revealing that CH25H was expressed in alveolar macrophages.

Example 7

Involvement of 25-Hydroxycholesterol in Airway Inflammation (1) Influence of 25-Hydroxycholesterol on Production of Cytokines in Bronchoalveolar Lavage Fluid To examine the involvement of CH25H on the morbid state of COPD, the effect of added 25-hydroxycholesterol (25-HC), i.e. CH25H reaction product, on alveolar macrophages was examined.

According to the method described in EXAMPLE 4, a mouse was exposed to cigarette smoke for 4 days, and on the next day of the final exposure, the bronchoalveolar lavage fluid was recovered according to the method described in EXAMPLE 4, and cells containing alveolar macrophages were seeded on a 96-well plate at a density of $1\times10^6$ cells/ml. On the next day, the cells were stimulated with LPS (10 ng/ml) and 25-HC (0.3 to 3 μg/ml) and cultured for 24 hours. According to the method described in EXAMPLE 1, total RNA was then recovered from the cells according to the attached manual, and the amounts of mRNAs of CXCL2 and IL-1β, that is, inflammatory cytokines, were quantified by the real-time quantitative PCR method. As each probe, the corresponding probe was selected from Assays on demand gene expression product (Applied Biosystems) and used. The expression level of each gene was calculated as relative expression value to rodent GAPDH by the comparative Ct value method.

Figure 6:
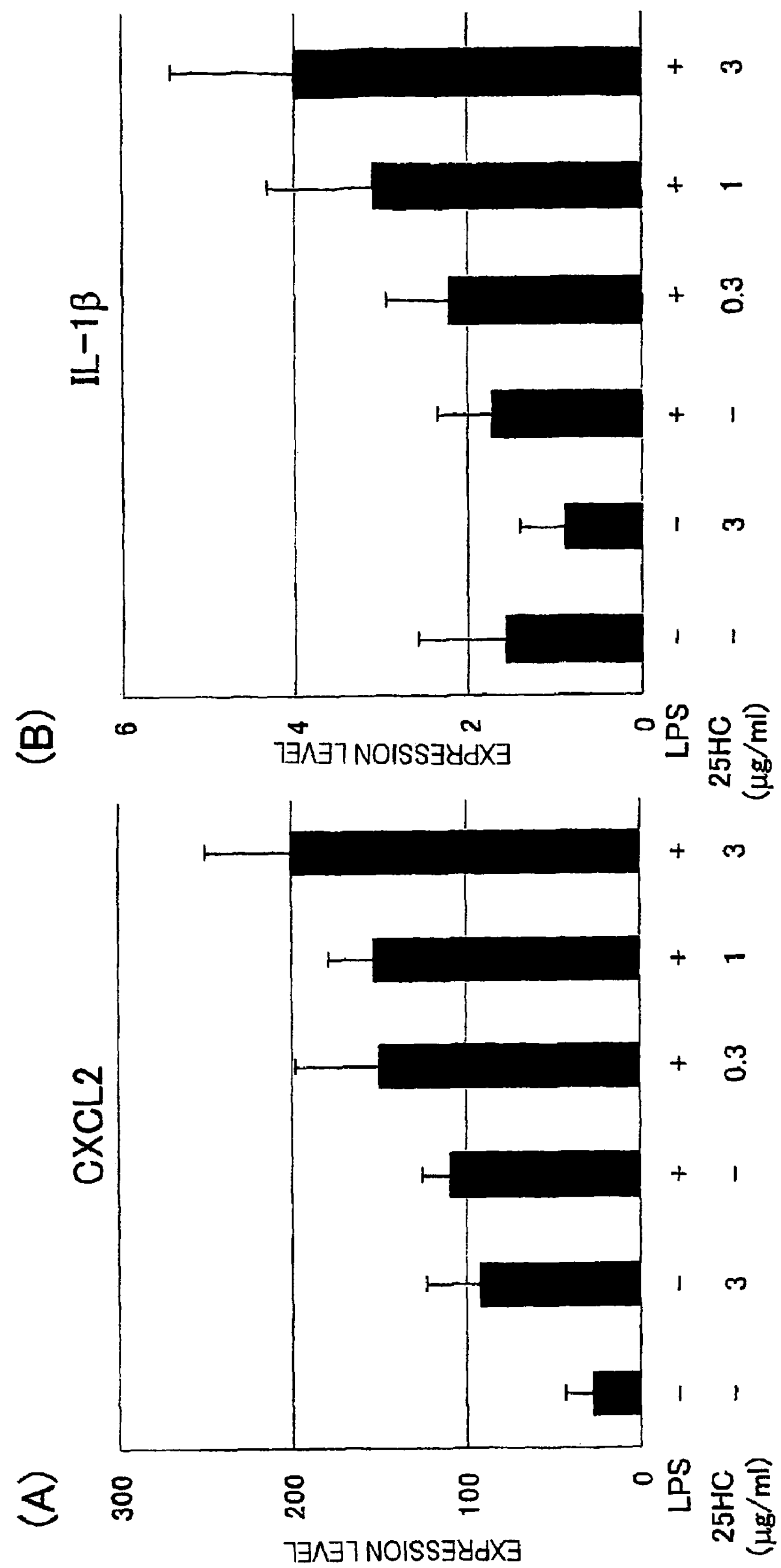
FIG. 6(A) is a graph showing the expression level of CXCL2 gene upon stimulation, with LPS and 25-HC, of cells in a bronchoalveolar lavage fluid from a cigarette smoke-exposed mouse. In the graph, the expression level of each gene is shown in the ordinate and the amounts of LPS and 25-HC in the abscissa.
FIG. 6(B) is a graph showing the expression level of IL-1β gene upon stimulation, with LPS and 25-HC, of cells in a bronchoalveolar lavage fluid from a cigarette smoke-exposed mouse. In the graph, the expression level of each gene is shown in the ordinate and the amounts of LPS and 25-HC in the abscissa.

As a result, the expression of CXCL2 and IL-1β was increased depending on the concentration of 25HC by co-stimulation with LPS and 25-HC, as compared with stimulation with LSP alone (FIG. 6).

(2) Production of Cytokines by Intratracheal Administration of 25-Hydroxycholesterol (25-HC)

To examine whether production of cytokines by 25-HC is observed in vivo as well, the effect of 25-HC administered to the lung of a mouse was examined.

25-HC or a control (physiological saline containing a solvent at the same concentration as used in dissolving 25-HC (10% aqueous ethanol)) was intratracheally administered at a dose of 50 μg/50 μl/mouse to C57BL/6 mice (6-week-old, male) under anesthesia with halothane, and 3, 6, 12, 24 and 48 hours after administration, the bronchoalveolar lavage fluid was recovered, and the amounts of KC and MIP-2, that is, inflammatory cytokines in the lavage fluid were measured by a commercial ELISA kit.

Figure 7:
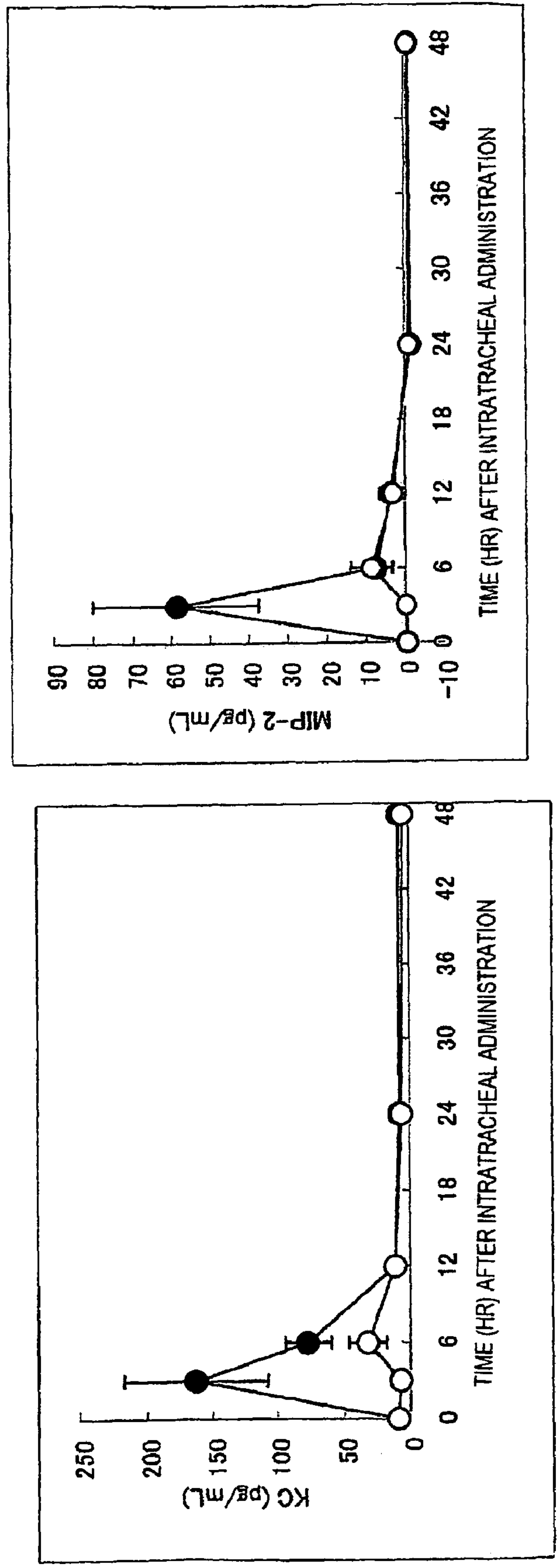
FIG. 7 shows graphs showing the amount of cytokines (KC and MIP-2) in a bronchoalveolar lavage fluid after an intratracheal administration of 25-H. In the graph on the left, the amount of KC is shown in the ordinate and the time after intratracheal administration is shown in the abscissa, while in the graph on the right, the amount of MIP-2 is shown in the ordinate and the time after intratracheal administration is shown in the abscissa. ● shows 25-HC, and ○ shows the control.

As a result, a significant increase in the amounts of KC and MIP-2 was recognized 3 hours after administration of 25-HC (FIG. 7).

(3) Neutrophil Infiltration by Intratracheal Administration of 25-Hydroxycholesterol To examine whether the airway inflammatory reaction by 25-HC is observed in vivo as well, the effect of 25-HC administered to the lung of a mouse was examined.

Figure 8:
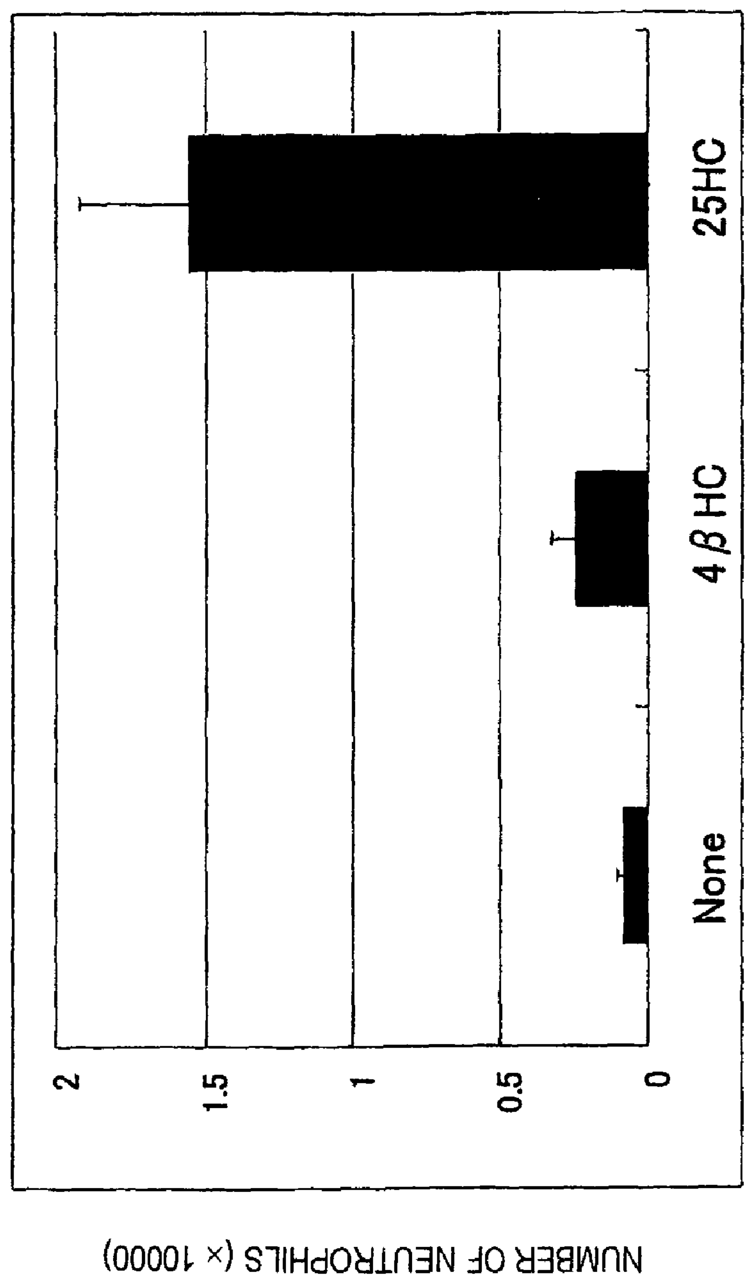
FIG. 8 is a graph showing the number of neutrophils in a bronchoalveolar lavage fluid after intratracheal administration of hydroxylated cholesterols. In the graph, the number of neutrophils is shown in the ordinate, and the intratracheally administered hydroxylated cholesterols are shown in the abscissa.

25-HC or a control (physiological saline containing a solvent at the same concentration as used in dissolving 25-HC (9.5% aqueous ethanol)), or 4β-hydroxycholesterol (4β-HC), was intratracheally administered for 4 days at a dose of 50 μg/50 μl/mouse/day to C57BL/6 mice (7-week-old, male) under anesthesia with ketamine and xylazine, and on the next day, the bronchoalveolar lavage fluid was recovered, and the number of inflammatory cells was determined. As a result, significant neutrophil infiltration was recognized in the 25-HC administration group only (FIG. 8).

From these results, CH25H produces 25-HC from cholesterol in alveolar macrophage, and its product 25-HC promotes production of inflammatory cytokines such as CXCL2 and IL-1β, thereby accelerating neutrophil infiltration in the airway and advancing the morbid state of COPD.

Example 8

Screening of Compounds having an Inhibitory Action on CH25H

COS cells were seeded onto a 6-well plate at a density of $2\times10^5$ cells/well, and on the next day, 2 μg of the above human CH25H expression plasmid (pcDNA-hCH25H) was introduced by using FuGENE6 (Roche Diagnostics) according to its attached manual. The cells were further cultured for 2 days, and after the medium was exchanged with a serum-free DEM medium containing 2-hydroxypropyl-β-cyclodextrin at a concentration of 20 mg/ml, the cells were cultured at 37° C. for 1 hour. Thereafter, the medium was exchanged with 5% lipopotein-poor serum-containing DMEM medium, and a test compound was added at a concentration of 10 μM. After 10 minutes, 2 μl $^{14}C$-cholesterol (final concentration 0.4 μM) was added, and the culture was continued. After 24 hours, cholesterols were extracted from the culture supernatant with an equal volume of $CHCl_3$:MeOH (2:1). The organic layer was evaporated to dryness, then re-dissolved in $CHCH_3$:MeOH (2:1) and applied onto Silica Gel 60 TLC plate (20 cm×20 cm, manufactured by Merck). Thereafter, the sample was developed with AcOEt/Ph-Me (4:6), and the conversion of cholesterols into 25-HC was detected by BAS2000 thereby determining CH25H enzyme activity (degree of conversion). Simultaneously, the CH25H enzyme activity (degree of conversion) of converting cholesterols into 25HC in the absence of a test compound was also determined.

From these results, the degree of inhibition of CH25H enzyme activity was calculated according to the following equation:

Degree of inhibition (%)=(1−(degree of conversion in the presence of the test compound/degree of conversion in the absence of the test compound))×100

The test compound showing a degree (%) of inhibition of 50% or more was selected as a compound having an inhibitory action on CH25H.

INDUSTRIAL APPLICABILITY

A protein comprising an amino acid sequence identical or substantially identical with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64 or SEQ ID NO: 66, and a polynucleotide encoding the protein, are useful for example as diagnostic markers etc. for respiratory diseases [for example, chronic obstructive pulmonary disease (for example, chronic bronchitis, pulmonary emphysema), diffuse panbronchiolitis, bronchial asthma, cystic fibrosis, hypersensitive pneumonia, pulmonary fibrosis etc.], chronic obstructive pulmonary disease (for example, chronic bronchitis, pulmonary emphysema), diffuse panbronchiolitis, bronchial asthma, cystic fibrosis, hypersensitive pneumonia, pulmonary fibrosis etc.] [sic].

A protein comprising an amino acid sequence identical or substantially identical with the amino acid sequence represented by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 or SEQ ID NO: 62, a polynucleotide encoding the protein, an inhibitor obtained by screening using e.g. an antibody to the protein, a neutralizing antibody inhibiting the activity of the protein, and an antisense polynucleotide to the above polynucleotide, can be used for example as prophylactic/therapeutic agents for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

A protein comprising an amino acid sequence identical or substantially identical with the amino acid sequence represented by SEQ ID NO: 64 or SEQ ID NO: 66, a polynucleotide encoding the protein, a promoter obtained by screening using e.g. an antibody to the protein, an antibody promoting the activity of the protein, the above protein, and the above polynucleotide can be used for example as prophylactic/therapeutic agents for respiratory diseases [for example, chronic obstructive pulmonary disease (chronic bronchitis, pulmonary emphysema), diffuse panbronchiolitis, bronchial asthma, cystic fibrosis, hypersensitive pneumonia, pulmonary fibrosis etc.].

The invention claimed is:

1. A method of screening for a potential prophylactic/therapeutic agent for respiratory diseases, which comprises:

(i) culturing a cell expressing a protein in the presence and absence of a test compound and measuring cholesterol hydroxylation activity of the protein, wherein the protein comprises (a) the amino acid sequence of SEQ ID NO: 2 or (b) an amino acid sequence having at least 90% identity to the amino acid sequence of SEQ ID NO: 2 and having cholesterol hydroxylation activity, or a salt thereof;

(ii) comparing the measured cholesterol hydroxylation activity of the protein in the presence of the test compound with the measured activity of the protein in the absence of the test compound;

(iii) selecting the test compound which decreases cholesterol hydroxylation activity of the protein by at least 20%;

(iv) measuring and comparing the production of inflammatory cytokines in the presence and absence of the test compound selected in step (iii); and (v) selecting the test compound which decreases the production of inflammatory cytokines as the prophylactic/therapeutic agent for respiratory diseases.

2. The screening method according to claim 1, wherein said protein comprises the amino acid sequence represented of SEQ ID NO: 2 or a salt thereof.

3. The method according to claim 1, wherein said respiratory disease is chronic obstructive pulmonary disease.

* * * * *